(12) United States Patent
Nyuli et al.

(10) Patent No.: US 9,345,573 B2
(45) Date of Patent: May 24, 2016

(54) METHODS AND APPARATUS FOR LOADING A PROSTHESIS ONTO A DELIVERY SYSTEM

(71) Applicant: Neovasc Tiara Inc., Richmond, CA (US)

(72) Inventors: Colin A. Nyuli, Vancouver (CA); Randy Matthew Lane, Langley (CA)

(73) Assignee: NEOVASC TIARA INC., Richmond, BC (CA)

( * ) Notice: Subject to any disclaimer, the term of this patent is extended or adjusted under 35 U.S.C. 154(b) by 308 days.

(21) Appl. No.: 13/904,827

(22) Filed: May 29, 2013

(65) Prior Publication Data

US 2014/0155990 A1 Jun. 5, 2014

Related U.S. Application Data

(60) Provisional application No. 61/653,273, filed on May 30, 2012.

(51) Int. Cl.
*A61F 2/24* (2006.01)
*A61F 2/95* (2013.01)

(52) U.S. Cl.
CPC .............. *A61F 2/2436* (2013.01); *A61F 2/2418* (2013.01); *A61F 2002/9522* (2013.01); *A61F 2220/005* (2013.01); *A61F 2220/0016* (2013.01); *A61F 2220/0058* (2013.01);
(Continued)

(58) Field of Classification Search
CPC ................ A61F 2/2436; A61F 2/2418; A61F 2230/0013; A61F 2230/005; A61F 220/005; A61F 220/0058; A61F 2250/006; A61F 2230/0054; A61F 2002/9522; Y10T 29/49908; Y10T 29/49913; Y10T 29/49925

USPC ............................ 29/515, 505, 508, 509, 516
See application file for complete search history.

(56) References Cited

U.S. PATENT DOCUMENTS 3,739,402 A * 6/1973 Cooley ................... A61F 2/2412
623/2.16
4,079,468 A * 3/1978 Liotta .................... A61F 2/2412
623/2.17
(Continued)

FOREIGN PATENT DOCUMENTS

AU WO 2010057262 A1 * 5/2010 ......... A61B 17/0057
CA 2263006 A1 * 8/1999 .............. A61F 2/958
(Continued)

OTHER PUBLICATIONS

Bavaria. CardiAQ Valve Technologies (CVT) discloses successful results of acute in vivo study of its novel transcatheter mitral valve implantation (TMVI) system. Enhanced Online News. Sep. 28, 2009. Accessed: Mar. 8, 2012. http://eon.businesswire.com/news/eon/20090928005120/en/CardiAQ-Valve-Technologies/Heart/heart-failure.
(Continued)

*Primary Examiner* — Moshe Wilensky
*Assistant Examiner* — Bayan Salone
(74) *Attorney, Agent, or Firm* — Wilson Sonsini Goodrich & Rosati

(57) ABSTRACT

A device for loading a prosthesis onto a delivery system includes a first housing having a central bore. One or more actuators on the first housing may be actuated radially inward to selectively compress a discrete portion of the prosthesis disposed in the central bore.

17 Claims, 60 Drawing Sheets

(52) U.S. Cl.
CPC .. *A61F 2230/005* (2013.01); *A61F 2230/0013* (2013.01); *A61F 2230/0054* (2013.01); *A61F 2250/006* (2013.01); *Y10T 29/49908* (2015.01); *Y10T 29/49913* (2015.01); *Y10T 29/49925* (2015.01)

(56) References Cited

U.S. PATENT DOCUMENTS

| | | | | |
|---|---|---|---|---|
| 4,204,283 | A * | 5/1980 | Bellhouse | A61F 2/2412 137/527 |
| 4,339,831 | A * | 7/1982 | Johnson | A61F 2/2418 137/512.15 |
| 4,340,977 | A * | 7/1982 | Brownlee | A61F 2/2412 137/846 |
| 4,470,157 | A * | 9/1984 | Love | A61F 2/2409 623/2.15 |
| 4,490,859 | A * | 1/1985 | Black | A61F 2/2412 623/2.16 |
| 4,865,600 | A * | 9/1989 | Carpentier | A61F 2/2427 623/2.11 |
| 5,415,667 | A * | 5/1995 | Frater | A61F 2/2457 623/2.11 |
| 5,669,919 | A * | 9/1997 | Sanders | A61F 2/2466 606/139 |
| 5,868,782 | A * | 2/1999 | Frantzen | A61F 2/91 128/899 |
| 5,928,281 | A * | 7/1999 | Huynh | A61F 2/2409 623/2.14 |
| 6,042,606 | A * | 3/2000 | Frantzen | A61F 2/91 606/194 |
| 6,074,417 | A * | 6/2000 | Peredo | A61F 2/2412 623/2.1 |
| 6,082,990 | A | 7/2000 | Jackson et al. | |
| 6,086,612 | A * | 7/2000 | Jansen | A61F 2/2412 623/2.17 |
| 6,113,631 | A * | 9/2000 | Jansen | A61F 2/2412 623/2.17 |
| 6,312,465 | B1 * | 11/2001 | Griffin | A61F 2/2409 623/2.18 |
| 6,358,277 | B1 * | 3/2002 | Duran | A61F 2/2412 623/2.11 |
| 6,458,153 | B1 * | 10/2002 | Bailey | A61F 2/2418 623/1.24 |
| 6,610,088 | B1 * | 8/2003 | Gabbay | A61F 2/2409 623/2.13 |
| 6,629,534 | B1 * | 10/2003 | St. Goar | A61B 17/0469 128/898 |
| 6,764,505 | B1 * | 7/2004 | Hossainy | A61F 2/91 427/2.25 |
| 6,875,231 | B2 * | 4/2005 | Anduiza | A61F 2/2418 623/1.15 |
| 6,929,660 | B1 * | 8/2005 | Ainsworth | A61F 2/91 623/1.15 |
| 7,018,406 | B2 * | 3/2006 | Seguin | A61F 2/2418 606/194 |
| 7,186,265 | B2 * | 3/2007 | Sharkawy | A61F 2/2409 623/2.38 |
| 7,201,772 | B2 * | 4/2007 | Schwammenthal | A61F 2/2418 623/1.24 |
| 7,311,730 | B2 * | 12/2007 | Gabbay | A61F 2/2409 606/153 |
| 7,377,938 | B2 * | 5/2008 | Sarac | A61F 2/2415 623/1.26 |
| 7,381,210 | B2 * | 6/2008 | Zarbatany | A61B 17/0467 128/898 |
| 7,381,219 | B2 * | 6/2008 | Salahieh | A61F 2/2418 623/2.11 |
| 7,422,603 | B2 * | 9/2008 | Lane | A61F 2/2412 623/2.14 |
| 7,442,204 | B2 * | 10/2008 | Schwammenthal | A61F 2/2418 623/1.24 |
| 7,455,689 | B2 * | 11/2008 | Johnson | A61F 2/2412 623/2.14 |
| 7,510,572 | B2 * | 3/2009 | Gabbay | A61F 2/2418 623/1.26 |
| 7,524,330 | B2 * | 4/2009 | Berreklouw | A61B 17/11 623/1.14 |
| 7,534,259 | B2 * | 5/2009 | Lashinski | A61B 17/0644 623/2.1 |
| 7,534,261 | B2 * | 5/2009 | Friedman | A61B 2/2409 623/2.17 |
| 7,621,948 | B2 * | 11/2009 | Herrmann | A61F 2/243 623/2.1 |
| 7,637,945 | B2 * | 12/2009 | Solem | A61B 17/00234 623/2.36 |
| 7,637,946 | B2 | 12/2009 | Solem et al. | |
| 7,837,727 | B2 * | 11/2010 | Goetz | A61F 2/2418 623/1.15 |
| 7,871,435 | B2 * | 1/2011 | Carpentier | A61F 2/2409 623/2.12 |
| 7,914,569 | B2 * | 3/2011 | Nguyen | A61F 2/2412 623/1.18 |
| 7,972,378 | B2 * | 7/2011 | Tabor | A61F 2/013 623/1.24 |
| 8,034,104 | B2 * | 10/2011 | Carpentier | A61F 2/2409 623/2.12 |
| 8,052,749 | B2 * | 11/2011 | Salahieh | A61F 2/2418 623/1.26 |
| 8,062,355 | B2 * | 11/2011 | Figulla | A61F 2/2418 623/1.24 |
| 8,066,755 | B2 * | 11/2011 | Zacharias | A61F 2/07 623/1.12 |
| 8,070,743 | B2 * | 12/2011 | Kagan | A61B 17/00234 604/264 |
| 8,070,802 | B2 * | 12/2011 | Lamphere | A61F 2/2418 623/1.26 |
| 8,075,609 | B2 * | 12/2011 | Penn | A61F 2/91 623/1.15 |
| 8,075,611 | B2 * | 12/2011 | Millwee | A61F 2/2412 623/1.24 |
| 8,092,520 | B2 * | 1/2012 | Quadri | A61F 2/2418 623/1.26 |
| 8,105,375 | B2 * | 1/2012 | Navia | A61F 2/2418 623/2.1 |
| 8,226,666 | B2 * | 7/2012 | Zarbatany | A61B 17/0467 606/139 |
| 8,246,677 | B2 * | 8/2012 | Ryan | A61F 2/2418 623/1.24 |
| 8,323,336 | B2 * | 12/2012 | Hill | A61F 2/2412 623/1.24 |
| 8,337,541 | B2 * | 12/2012 | Quadri | A61F 2/2418 623/1.11 |
| 8,353,954 | B2 * | 1/2013 | Cai | A61F 2/2415 623/2.14 |
| 8,403,983 | B2 * | 3/2013 | Quadri | A61F 2/2412 623/1.24 |
| 8,414,644 | B2 * | 4/2013 | Quadri | A61F 2/2418 623/2.11 |
| 8,512,398 | B2 * | 8/2013 | Alkhatib | A61F 2/013 623/2.11 |
| 8,512,403 | B2 * | 8/2013 | Navia | A61F 2/2445 623/2.36 |
| 8,579,964 | B2 * | 11/2013 | Lane | A61F 2/2418 623/2.11 |
| 8,608,797 | B2 * | 12/2013 | Gross | A61F 2/2445 606/151 |
| 8,623,079 | B2 * | 1/2014 | Savage | A61F 2/2418 623/1.26 |
| 8,628,566 | B2 * | 1/2014 | Eberhardt | A61F 2/2418 623/1.15 |
| 8,652,203 | B2 * | 2/2014 | Quadri | A61F 2/2418 623/1.12 |
| 8,795,356 | B2 * | 8/2014 | Quadri | A61F 2/2418 623/2.11 |
| 8,840,661 | B2 * | 9/2014 | Manasse | A61F 2/2418 623/2.1 |
| 8,876,894 | B2 * | 11/2014 | Tuval | A61F 2/2418 623/2.14 |
| 8,894,702 | B2 * | 11/2014 | Quadri | 623/1.24 |
| 8,911,455 | B2 * | 12/2014 | Quadri | A61F 2/2418 606/139 |
| 8,979,922 | B2 * | 3/2015 | Jayasinghe | A61F 2/2418 623/2.1 |

(56) References Cited

U.S. PATENT DOCUMENTS

| | | | |
|---|---|---|---|
| 9,023,100 B2* | 5/2015 | Quadri | A61F 2/2418 623/2.11 |
| 9,034,032 B2* | 5/2015 | McLean | A61F 2/2409 623/2.12 |
| 9,072,603 B2* | 7/2015 | Tuval | A61F 2/2418 |
| 2001/0007956 A1* | 7/2001 | Letac | A61F 2/2412 623/2.11 |
| 2002/0032481 A1* | 3/2002 | Gabbay | A61F 2/2418 623/2.11 |
| 2002/0177899 A1* | 11/2002 | Eum | A61F 2/95 623/23.7 |
| 2002/0198584 A1* | 12/2002 | Unsworth | A61F 2/90 623/1.11 |
| 2003/0105517 A1* | 6/2003 | White | A61F 2/91 623/1.17 |
| 2003/0114913 A1* | 6/2003 | Spenser | A61F 2/2412 623/1.11 |
| 2003/0135970 A1 | 7/2003 | Thornton | |
| 2003/0176914 A1* | 9/2003 | Rabkin | A61F 2/91 623/1.15 |
| 2004/0093060 A1* | 5/2004 | Seguin | A61F 2/2418 623/1.11 |
| 2004/0102842 A1* | 5/2004 | Jansen | A61F 2/2412 623/2.38 |
| 2004/0117009 A1* | 6/2004 | Cali | A61F 2/2412 623/2.12 |
| 2004/0181238 A1* | 9/2004 | Zarbatany | A61B 17/0467 606/108 |
| 2004/0193261 A1* | 9/2004 | Berreklouw | A61B 17/11 623/2.11 |
| 2004/0215325 A1* | 10/2004 | Penn | A61F 2/91 623/1.15 |
| 2004/0225353 A1* | 11/2004 | McGuckin, Jr. | A61F 2/2412 623/2.11 |
| 2004/0236411 A1* | 11/2004 | Sarac | A61F 2/2415 623/1.26 |
| 2004/0243230 A1* | 12/2004 | Navia | A61F 2/2445 623/2.36 |
| 2005/0075727 A1* | 4/2005 | Wheatley | A61F 2/2457 623/2.17 |
| 2005/0107872 A1* | 5/2005 | Mensah | A61L 27/16 623/2.14 |
| 2005/0137686 A1* | 6/2005 | Salahieh | A61F 2/2418 623/2.11 |
| 2005/0137690 A1* | 6/2005 | Salahieh | A61F 2/2418 623/2.11 |
| 2005/0159811 A1* | 7/2005 | Lane | A61F 2/2412 623/2.14 |
| 2005/0182486 A1* | 8/2005 | Gabbay | A61F 2/2409 623/2.11 |
| 2006/0020247 A1* | 1/2006 | Kagan | A61B 17/00234 604/264 |
| 2006/0020327 A1* | 1/2006 | Lashinski | A61B 17/0644 623/1.25 |
| 2006/0058872 A1* | 3/2006 | Salahieh | A61F 2/2418 623/2.18 |
| 2006/0095115 A1* | 5/2006 | Bladillah | A61F 2/2418 623/1.16 |
| 2006/0149360 A1* | 7/2006 | Schwammenthal | A61F 2/2418 623/1.24 |
| 2006/0195183 A1* | 8/2006 | Navia | A61F 2/2409 623/2.18 |
| 2006/0241745 A1 | 10/2006 | Solem | |
| 2006/0259135 A1 | 11/2006 | Navia et al. | |
| 2006/0259136 A1* | 11/2006 | Nguyen | A61F 2/2412 623/2.18 |
| 2006/0293698 A1* | 12/2006 | Douk | A61B 17/08 606/142 |
| 2006/0293745 A1* | 12/2006 | Carpentier | A61F 2/2409 623/2.19 |
| 2007/0016286 A1* | 1/2007 | Herrmann | A61F 2/243 623/2.11 |
| 2007/0043435 A1* | 2/2007 | Seguin | A61F 2/2418 623/2.11 |
| 2007/0050020 A1* | 3/2007 | Spence | A61F 2/2412 623/2.11 |
| 2007/0050021 A1* | 3/2007 | Johnson | A61F 2/2412 623/2.14 |
| 2007/0142906 A1* | 6/2007 | Figulla | A61F 2/2418 623/2.11 |
| 2007/0255394 A1* | 11/2007 | Ryan | A61F 2/2412 623/1.24 |
| 2007/0293940 A1* | 12/2007 | Schaeffer | A61F 2/07 623/1.16 |
| 2008/0022504 A1* | 1/2008 | Melsheimer | A61F 2/95 29/525 |
| 2008/0053577 A1* | 3/2008 | Syed | C22C 1/023 148/556 |
| 2008/0071361 A1* | 3/2008 | Tuval | A61F 2/2418 623/2.1 |
| 2008/0082164 A1* | 4/2008 | Friedman | A61F 2/2409 623/2.11 |
| 2008/0097571 A1* | 4/2008 | Denison | A61F 2/91 623/1.11 |
| 2008/0127707 A1* | 6/2008 | Kokish | A61F 2/95 72/402 |
| 2008/0147179 A1* | 6/2008 | Cai | A61F 2/2415 623/2.4 |
| 2008/0177381 A1* | 7/2008 | Navia | A61F 2/2418 623/2.11 |
| 2008/0183273 A1* | 7/2008 | Mesana | A61F 2/2418 623/1.11 |
| 2008/0221672 A1* | 9/2008 | Lamphere | A61F 2/2418 623/2.12 |
| 2008/0228201 A1* | 9/2008 | Zarbatany | A61B 17/0467 606/139 |
| 2008/0228254 A1* | 9/2008 | Ryan | A61F 2/2418 623/1.2 |
| 2008/0243245 A1* | 10/2008 | Thambar | A61F 2/2418 623/2.11 |
| 2009/0005863 A1* | 1/2009 | Goetz | A61F 2/2418 623/2.18 |
| 2009/0012602 A1* | 1/2009 | Quadri | A61F 2/07 623/1.35 |
| 2009/0082844 A1* | 3/2009 | Zacharias | A61F 2/07 623/1.13 |
| 2009/0138079 A1* | 5/2009 | Tuval | A61F 2/2418 623/2.11 |
| 2009/0171456 A1* | 7/2009 | Kveen | A61F 2/2418 623/2.11 |
| 2009/0188964 A1* | 7/2009 | Orlov | A61B 17/115 227/175.3 |
| 2009/0216314 A1* | 8/2009 | Quadri | A61F 2/2418 623/1.17 |
| 2009/0276040 A1* | 11/2009 | Rowe | A61B 17/0401 623/2.18 |
| 2009/0281618 A1* | 11/2009 | Hill | A61F 2/2418 623/1.26 |
| 2009/0287296 A1* | 11/2009 | Manasse | A61F 2/2418 623/1.18 |
| 2009/0287299 A1* | 11/2009 | Tabor | A61F 2/013 623/1.26 |
| 2009/0292350 A1* | 11/2009 | Eberhardt | A61F 2/2418 623/1.16 |
| 2009/0306768 A1* | 12/2009 | Quadri | A61F 2/2418 623/1.26 |
| 2009/0318871 A1* | 12/2009 | Zarbatany | A61B 17/0467 604/174 |
| 2010/0036479 A1* | 2/2010 | Hill | A61F 2/2418 623/1.15 |
| 2010/0082094 A1* | 4/2010 | Quadri | A61F 2/2412 623/1.26 |
| 2010/0191326 A1* | 7/2010 | Alkhatib | A61F 2/013 623/2.11 |
| 2010/0217382 A1* | 8/2010 | Chau | A61F 2/2418 623/1.26 |
| 2010/0249894 A1* | 9/2010 | Oba | A61F 2/2418 623/1.11 |
| 2010/0286768 A1* | 11/2010 | Alkhatib | A61F 2/2436 623/2.11 |
| 2010/0298931 A1* | 11/2010 | Quadri | A61F 2/2418 623/2.11 |

(56) References Cited

U.S. PATENT DOCUMENTS

| | | | |
|---|---|---|---|
| 2010/0305685 A1* | 12/2010 | Millwee | A61F 2/2412 623/1.26 |
| 2011/0004296 A1* | 1/2011 | Lutter | A61B 17/0401 623/1.26 |
| 2011/0015731 A1* | 1/2011 | Carpentier | A61F 2/2409 623/2.17 |
| 2011/0114230 A1* | 5/2011 | Syed | C22C 14/00 148/563 |
| 2011/0208297 A1* | 8/2011 | Tuval | A61F 2/2418 623/2.17 |
| 2011/0208298 A1* | 8/2011 | Tuval | A61F 2/2418 623/2.17 |
| 2011/0224678 A1* | 9/2011 | Gabbay | A61B 17/3468 606/108 |
| 2011/0264196 A1* | 10/2011 | Savage | A61F 2/2418 623/1.26 |
| 2011/0319989 A1* | 12/2011 | Lane | A61F 2/2418 623/2.11 |
| 2012/0041550 A1* | 2/2012 | Salahieh | A61F 2/2418 623/2.36 |
| 2012/0078353 A1* | 3/2012 | Quadri | A61F 2/2418 623/2.11 |
| 2012/0101572 A1* | 4/2012 | Kovalsky | A61F 2/2418 623/2.19 |
| 2012/0179239 A1 | 7/2012 | Quadri | |
| 2012/0215303 A1* | 8/2012 | Quadri | A61F 2/2418 623/2.18 |
| 2012/0271398 A1* | 10/2012 | Essinger | A61F 2/2412 623/1.11 |
| 2012/0303116 A1* | 11/2012 | Gorman, III | A61F 2/2418 623/2.11 |
| 2013/0053950 A1* | 2/2013 | Rowe | A61B 17/0401 623/2.19 |
| 2013/0110227 A1* | 5/2013 | Quadri | A61F 2/2418 623/2.11 |
| 2013/0131788 A1* | 5/2013 | Quadri | A61F 2/2412 623/2.4 |
| 2013/0131793 A1* | 5/2013 | Quadri | A61F 2/2412 623/2.38 |
| 2013/0138203 A1* | 5/2013 | Quadri | A61F 2/2418 623/1.16 |
| 2013/0138207 A1* | 5/2013 | Quadri | A61F 2/2418 623/2.18 |
| 2013/0144378 A1* | 6/2013 | Quadri | A61F 2/2418 623/2.1 |
| 2013/0144380 A1* | 6/2013 | Quadri | A61F 2/2418 623/2.11 |
| 2013/0144381 A1* | 6/2013 | Quadri | A61F 2/2418 623/2.11 |
| 2013/0184813 A1* | 7/2013 | Quadri | A61F 2/2412 623/2.18 |
| 2013/0211508 A1* | 8/2013 | Lane | A61F 2/2403 623/2.11 |
| 2013/0304200 A1* | 11/2013 | McLean | A61F 2/2418 623/2.18 |
| 2013/0310928 A1* | 11/2013 | Morriss | A61F 2/2418 623/2.12 |
| 2014/0039611 A1* | 2/2014 | Lane | A61F 2/2418 623/2.11 |
| 2014/0052237 A1* | 2/2014 | Lane | A61F 2/2412 623/2.11 |
| 2014/0155990 A1* | 6/2014 | Nyuli | A61F 2/2418 623/2.11 |
| 2014/0172085 A1* | 6/2014 | Quadri | A61F 2/2418 623/2.38 |
| 2014/0172086 A1* | 6/2014 | Quadri | A61F 2/2418 623/2.38 |
| 2014/0222136 A1* | 8/2014 | Geist | A61F 2/2466 623/2.11 |
| 2014/0257467 A1* | 9/2014 | Lane | A61F 2/2412 623/2.11 |
| 2014/0277390 A1* | 9/2014 | Ratz | A61F 2/2418 623/1.26 |
| 2014/0277422 A1* | 9/2014 | Ratz | A61F 2/2418 623/2.37 |
| 2014/0277427 A1* | 9/2014 | Ratz | A61F 2/2409 623/2.38 |
| 2015/0216655 A1* | 8/2015 | Lane | A61F 2/2418 623/2.37 |

FOREIGN PATENT DOCUMENTS

| | | | | |
|---|---|---|---|---|
| CA | WO 2011137531 A1 * | 11/2011 | | A61F 2/2418 |
| CA | WO 2011137531 A9 * | 1/2012 | | A61F 2/2418 |
| CH | WO 2009053497 A1 * | 4/2009 | | A61F 2/2418 |
| DE | 102006052564 B3 * | 12/2007 | | A61F 2/2418 |
| DE | 102006052564 B3 | 12/2007 | | |
| FR | WO 2012035279 A1 * | 3/2012 | | A61F 2/2418 |
| GB | 1264471 A | 2/1972 | | |
| GB | 1264471 A * | 2/1972 | | A61F 2/2418 |
| GB | 1315844 A * | 5/1973 | | A61F 2/2412 |
| GB | 1315844 A | 5/1973 | | |
| WO | WO 98/19633 A1 | 5/1998 | | |
| WO | WO 02/11646 A1 | 2/2002 | | |
| WO | WO 2006/097931 A2 | 9/2006 | | |
| WO | WO-2007058857 A2 | 5/2007 | | |
| WO | WO 2007/122459 A2 | 11/2007 | | |
| WO | WO 2008/013915 A2 | 1/2008 | | |
| WO | WO 2008005535 A2 * | 1/2008 | | A61F 2/91 |
| WO | WO-2008005535 A2 | 1/2008 | | |
| WO | WO 2008/103722 A2 | 8/2008 | | |
| WO | WO 2008013915 A9 * | 8/2008 | | A61F 2/2418 |
| WO | WO 2009/033469 A1 | 3/2009 | | |
| WO | WO 2009033469 A1 * | 3/2009 | | A61B 17/0401 |
| WO | WO-2009033469 A1 | 3/2009 | | |
| WO | WO-2009053497 A1 | 4/2009 | | |
| WO | WO 2009/134701 A2 | 11/2009 | | |
| WO | WO 2010/004546 A1 | 1/2010 | | |
| WO | WO 2010/037141 A1 | 4/2010 | | |
| WO | WO-2010057262 A1 | 5/2010 | | |
| WO | WO 2010/130789 A1 | 11/2010 | | |
| WO | WO 2011/137531 A1 | 11/2011 | | |
| WO | WO-2012035279 A1 | 3/2012 | | |

OTHER PUBLICATIONS

Bavaria. CardiAQ Valve Technologies. TCT Company Overview. Transcatheter Cardiovascular Therapeutics Conference. San Francisco, CA. Sep. 21-25, 2009.

CardiAQ Valve Technologies. Percutaneous mitral valve replacement. START-UP. Jun. 2009; 14(6):48-49.

Carpentier-Edwards. Why compromise in the mitral position? Edwards Lifesciences. 2004.

Fitzgerald. Tomorrow's technology: percutaneous mitral valve replacement, chordal shortening and beyond. Transcatheter Valve Therapies (TVT) Conference. Seattle, WA. Jun. 7, 2010.

Mack. Advantages and limitations of surgical mitral valve replacement; lessons for the transcatheter approach. Jun. 7, 2010. Texas Cardiovascular Innovative Ventures (TCIV) Conference. Dallas, TX. Dec. 8, 2010.

Medical Devices Today. CardiAQ Valve Technologies. START-UP-Jul. 17, 2009. Accessed: Mar. 8, 2012. http:/www.medicaldevicestoday.com/2009/07/medical-device-start-up-cardiaq-valve-technologies-percutaneous-mitral-valve-replacement.html.

Ostrovsky. Transcatheter mitral valve implantation technology from CardiAQ. Posted Jan. 15, 2010. Accessed Jun. 27, 2012 from http://medgadget.com/2010/01/transcatheter_mitral_valve_implantation_technology_from_cardiaq.html.

Ratz. CardiAQ Valve Technologies. Innovations in heartvalve therapy. In3 San Francisco. Jun. 18, 2008. PowerPoint presentation in 19 slides.

Ruiz. Overview of novel transcatheter valve technologies. Glimpse into the future. New transcatheter mitral valve treatment. Euro PCR. Paris, France. May 27, 2010.

International search report and written opinion dated Sep. 4, 2013 for PCT/CA2013/000530.

Al-Attar. Next generation surgical aortic biological prostheses: sutureless valves. European Society of Cardiology. Dec. 21, 2011; 10(14):1-3.

(56) References Cited

OTHER PUBLICATIONS

Banai, et al. Tiara: a novel catheter-based mitrel valve bioprosthesis: initial experiments and short-term pre-clinical results. J Am Coll Cardiol. Oct. 9, 2012;60(15):1430-1. doi: 10.1016/j.jacc.2012.05.047. Epub Sep. 12, 2012.
Berreklouw, et al. Sutureless mitral valve replacement with bioprostheses and Nitinol attachment rings: feasibility in acute pig experiments. J Thorac Cardiovasc Surg. Aug. 2011;142(2):390-5.e1. doi: 10.1016/j.jtcvs.2010.12.018. Epub Feb. 4, 2011.
Boudjemline, et al. Steps toward the percutaneous replacement of artrioventicular vavles an experimental study. J Am Coll Cardiol. Jul. 19, 2005;46(2):360-5.
Brinkman, et al. Transcatheter cardiac valve interventions. Surg Clin North Am. Aug. 2009;89(4):951-66, x. doi: 10.1016/j.suc.2009.06.004.
CardiAQ Valve Technologies to pursue first-in-man studies of its transcatheter mitral valve system. Cardiac Interventions Today. Jan. 12, 2010.
Chiam, et al. Percutaneous transcatheter aortic valve implantation: assessing results, judging outcomes, and planning trials: the interventionalist perspective. JACC Cardiovasc Interv. Aug. 2008;1(4):341-50. doi: 10.1016/j.jcin.2008.03.018.
Condado, et al. Percutaneous treatment of heart valves. Rev Esp Cardiol. Dec. 2006;59(12):1225-31.
CoreValve USA. An advanced TAVR design. Medtronic.com. Accessed Jan. 27, 2015.
De Backer, et al. Percutaneous transcatheter mitrel valve replacement: an overview of devices in preclinical and early clinical evaluation. Circ Cardiovasc Interv. Jun. 2014;7(3):400-9. doi: 10.1161/CIRCINTERVENTIONS.114.001607.
Edwards Lifesciences 2005 annual report. Accessed Jan. 27, 2015.
Fanning, et al. Transcatheter aortic valve implantation (TAVI): valve design and evolution. Int J Cardiol. Oct. 3, 2013;168(3):1822-31. doi:10.1016/j.ijcard.2013.07.117. Epub Aug. 20, 2013.
Gillespie, et al. Sutureless mitral valve replacement: initial steps toward a percutaneous procedure. Ann Thorac Surg. Aug. 2013;96(2):670-4. doi: 10.1016/j.athoracsur.2013.02.065.
Grube, et al. Percutaneous implantation of the CoreValve self-expanding valve prosthesis in high-risk patients with aortic valve disease: the Siegburg first-in-man study. Circulation. Oct. 10, 2006;114(15):1616-24. Epub Oct. 2, 2006.
Harmon, et al. Effect of acute myocardial infarction on the angle between the mitral and aortic valve plane. Am J Cardiol. Aug. 1, 1999;84(3):342-4, A8.
Herrman. Trancatheter mitral valve implantation. Cardiac Interventions Today. Aug./Sep. 2009; 81-85.
Ionasec, et al. Personalized modeling and assessment of the aortic-mitral coupling from 4D TEE and CT. Med Image Comput Comput Assist Interv. 2009;12(Pt 2):767-75.
Karimi, et al. Percutaneous Valve Therapies. SIS 2007 Year book. Chapter 11. 11 pages.
Kumar, et al. Design considerations and quantitative assessment for the development of percutaneous mitral valve sent. Med Eng Phys. Jul. 2014;36(7):882-8. doi: 10.1016/j.medengphy.2014.03.010. Epub Apr. 16, 2014.
Lauten; et al., "Experimental evaluation of the JenaClip transcatheter aortic valve.", Sep. 1, 2009, 74(3), 514-9.
Leon, et al. Transcatheter aortic valve replacement in patients with critical aortic stenosis: rationale, device descriptions, early clinical experiences, and perspectives. Semin Thorac Cardiovasc Surg. 2006 Summer;18(2):165-74.
Lozonschi, et al. Transapical mitral valved stent implantation. Ann Thorac Surg. Sep. 2008;86(3):745-8. doi: 10.116/j.athoracsur.2008.05.039.
Lutter, et al. Off-pump transapical mitrel valve replacement. Eur J Cardiothorac Surg. Jul. 2009;36(1):124-8; discussion 128. doi.10.1016/j.ejcts.2009.02.037. Epub Apr. 25, 2009.

Lutter, et al. Transapical mitral valve implantation: the Lutter valve. Heart Lung Vessel. 2013;5(4):201-6.
Ma, et al. Double-crowned valved stents for off-pump mitral valve replacement. Eur J Cardiothorac Surg. Aug. 2005;28(2):194-8; discussion 198-9.
Masiano, et al. Mitral transcatheter technologies. Rambam Maimonides Med J. Jul. 25, 2013;4(3):e0015. doi:10.5041/RMMJ.10115. Print Jul. 2013.
Navia, et al. Sutureless implantation a expandable mitrel stent-valve prosthesis in acute animal mode. TCT728. JACC. Nov. 8, 2011. vol. 58, No. 20 Suppl B. B194.
Orton. Mitralseal: hybrid trancatheter mitrel valve replacement. Colorado State University. 2011; 311-312. https://www.acvs.org/files/proceedings/2011/data/papers/102.pdf.
Piazza, et al. Anatomy of the aortic valvar complex and its implications for transcatheter implantation of the aortic valve. Circ Cardiovasc Interv. Aug. 2008;1(1):74-81. doi: 10.1161/CIRCINTERVENTIONS.108.780858.
Pluth, et al. Aortic and mitral valve replacement with cloth-covered Braunwald-Cutter prosthesis. A three-year follow-up. Ann Thorac Surg. Sep. 1975;20(3):239-48.
Preston-Maher, et al. A Technical Review of Minimally Invasive Mitral Valve Replacements. Cardiovasc Eng Technol. 2015;6(2):174-184. Epub Nov. 25, 2014.
Quadri, et al. CVT is developing a non-surgical apporach to replacing mitral valves that may be the alternative to open-chest surgery. CardiAQ Valve Technologies. May 8, 2009.
Ribiero, et al. Balloon-expandable prostheses for transcatheter aortic valve replacement. Prog Cardiovasc Dis. May-Jun. 2014;56(6):583-95. doi: 10.1016/j.pcad.2014.02.001. Epub Mar. 1, 2014.
Seidel, et al. A Mitral valve prosthesis and a study of thrombosis on heart valves in dogs. J Surg Res. May 1962;2:168-75.
Shuto, et al. Percutaneous transvenous Melody valve-in-ring procedure for mitral valve replacement. J Am Coll Cardiol. Dec. 6, 2011;58(24):2475-80. doi: 10.1016/j.jacc.2011.09.021.
Sondergaard, et al. First-in-human CardiAQ transcatheter mitral valve implantation via transcapical approach. TCT-811. JACC. Sep. 13, 2014. vol. 64, No. 11 Suppl B. B237.
Spencer, et al. Surgical treatment of valvular heart disease. Part V. Prosthetic replacement of the mitral valve. American Heart Journal. Oct. 1968; 76(4):576-580.
Spillner, et al. New sutureless 'atrial mitral-valve prosthesis' for minimally invasive mitral valve therapy. Textile Research Journal. 2010:1-7.
TAVR. Engager system. Precise Valve positioning. Accessed Jan. 28, 2015.
The JenaValve—the prosthesis. JenaValve Technology. Accessed Jan. 28, 2015.
Timek, et al. Aorto-mitral annular dynamics. Ann Thorac Surg. Dec. 2003;76(6):1944-50.
Tsang, et al. Changes in aortic-mitral coupling with severe aortic stenosis. JACC. Mar. 9, 2010; vol. 55. Issue 1A.
Veronesi, et al. A study of functional anatomy of aortic-mitral valve coupling using 3D matrix transesophageal echocardiography. Circ Cardiovasc Imaging. Jan. 2009;2(1):24-31. doi: 10.1161/CIRCIMAGING.108.785907. Epub Dec. 2, 2008.
Vu, et al. Novel sutureless mitrel valve implantation method involving a bayonet insertion and release mechanism: a proof of concept study in pigs. J Thorac Cardiovasc Surg. Apr. 2012;143(4):985-8. doi: 10.1016/j.jtcvs.2012.01.037. Epub. Feb. 11, 2012.
Walther, et al. Transapical approach for sutureless stent-fixed aortic valve implantation: experimental results. Eur J Cadiothorac Surg. May 2006;29(5):703-8. Epub Apr. 5, 2006.
Webb, et al. Transcatheter aortic valve implantation: the evolution of prostheses, delivery systems and approaches. Arch Cardiovasc Dis. Mar. 2012;105(3):153-9. doi: 10.1016/j.acvd.2012.02.001. Epub Mar. 16, 2012.
European search report and opinion dated Sep. 14, 2015 for EP Application No. 13796278.3.

* cited by examiner

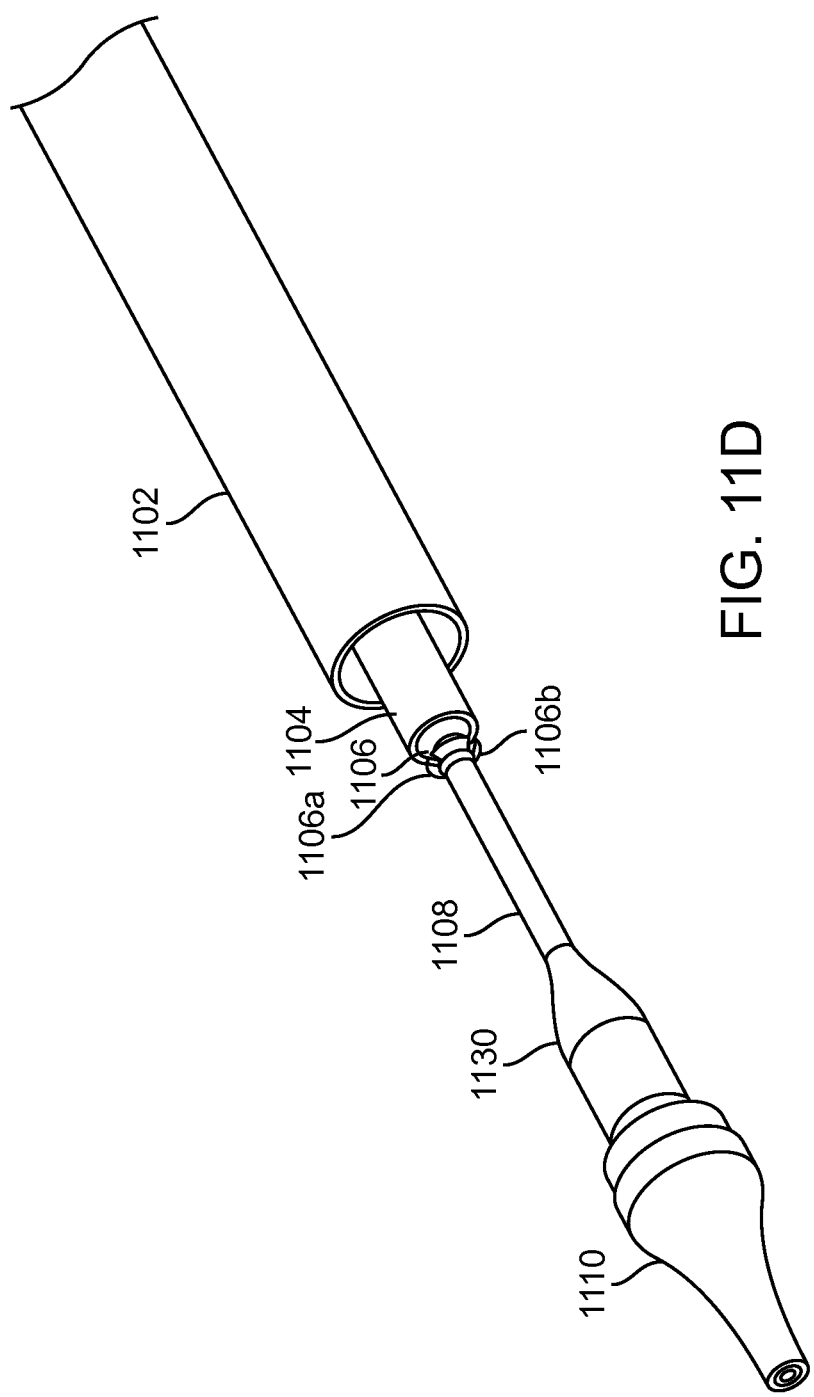

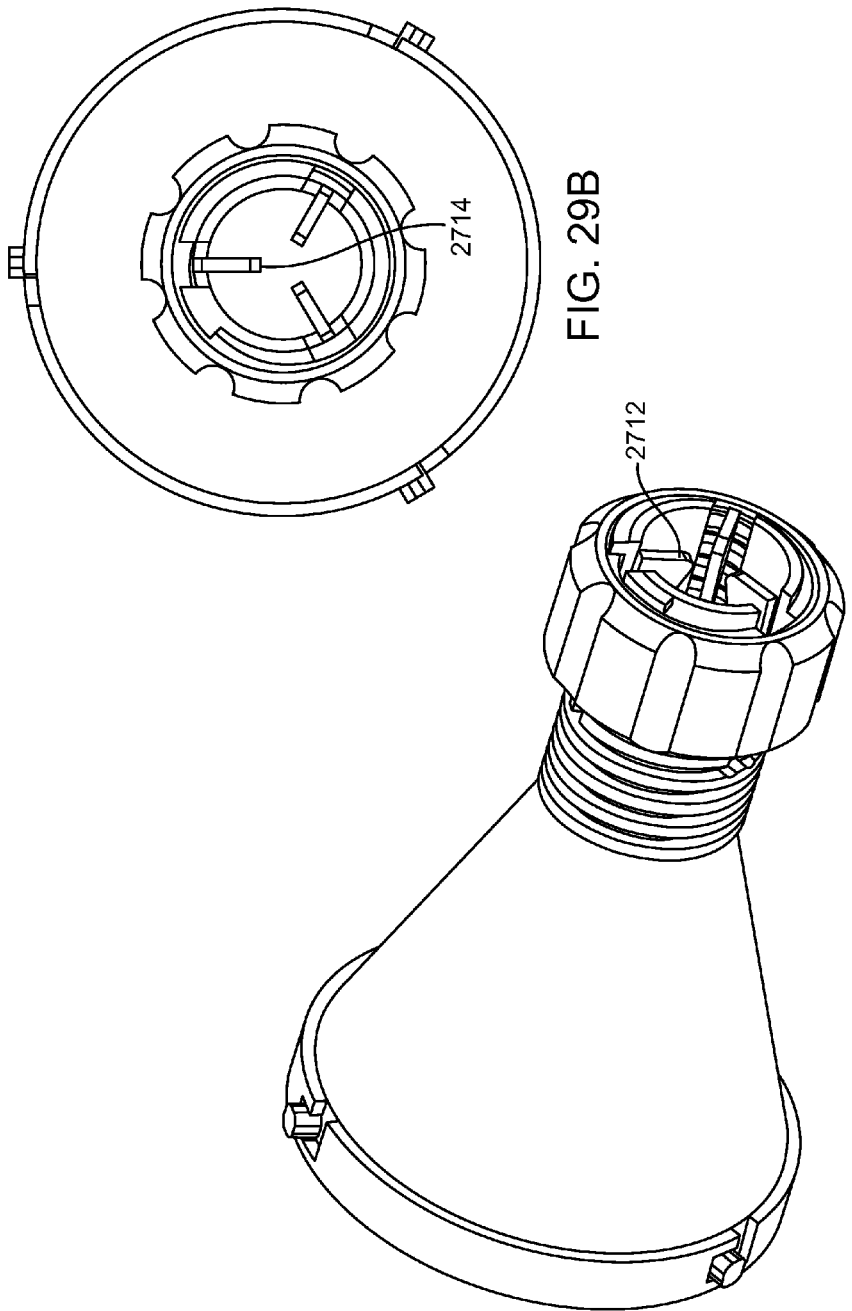

METHODS AND APPARATUS FOR LOADING A PROSTHESIS ONTO A DELIVERY SYSTEM

CROSS-REFERENCE

The present application is a non-provisional of, and claims the benefit of U.S. Provisional Patent Application No. 61/653,273 filed on May 30, 2012; the entire contents of which are incorporated herein by reference.

BACKGROUND OF THE INVENTION

1. Field of the Invention

The present invention generally relates to medical devices and methods, and more particularly relates to devices and methods for loading a prosthesis onto a delivery system. The prosthesis may be any device but in preferred embodiments is used to treat valve insufficiency, such as mitral insufficiency, also referred to as mitral regurgitation. The delivery system may be any system used to deliver the prosthesis either by traditional surgical implantation methods, or by less invasive percutaneous catheter or minimally invasive transapical methods.

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (also referred to as regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or reshaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

While these devices and methods are promising treatments for valvar insufficiency, they can be difficult to deliver, and difficult to load onto the delivery system. Therefore, it would be desirable to provide improved devices and methods for coupling the prosthesis with the delivery system. At least some of these objectives will be met by the devices and methods disclosed below.

2. Description of the Background Art

By way of example, PCT international patent number PCT/US2008/0544 0 (published as PCT international publication no. WO2008/103722), the disclosure of which is hereby incorporated by reference, describes a transcatheter mitral valve prosthesis that comprises a resilient ring, a plurality of leaflet membranes mounted with respect to the ring so as to permit blood flow therethrough in one direction, and a plurality of tissue-engaging positioning elements movably mounted with respect to the ring and dimensioned to grip the anatomical structure of the heart valve annulus, heart valve leaflets, and/or heart wall. Each of the positioning elements defines respective proximal, intermediate, and distal tissue engaging regions cooperatively configured and dimensioned to simultaneously engage separate corresponding areas of the tissue of an anatomical structure, and may include respective first, second, and third elongate tissue-piercing elements. The valve prosthesis may also include a skirt mounted with respect to the resilient ring for sealing a periphery of the valve prosthesis against a reverse flow of blood around the valve prosthesis.

PCT international patent number PCT/US2009/041754 (published as PCT international publication no. WO2009/134701), the disclosure of which is hereby incorporated by reference, describes a prosthetic mitral valve assembly that comprises an anchor or outer support frame with a flared upper end and a tapered portion to fit the contours of the native mitral valve, and a tissue-based one-way valve mounted therein. The assembly is adapted to expand radially outwardly and into contact with the native heart tissue to create a pressure fit, and further includes tension members anchoring the leaflets of the valve assembly to a suitable location on the heart to function as prosthetic chordae tendineae.

Also known are prosthetic mitral valve assemblies that utilize a claw structure for attachment of the prosthesis to the heart (see, for example, U.S. patent application publication no. US2007/0016286 to Hermann et al., the disclosure of which is hereby incorporated by reference), as are prosthetic mitral valve assemblies that rely on the application of axial rather than radial clamping forces to facilitate the self-positioning and self-anchoring of the prosthesis with respect to the native anatomical structure.

Another method which has been proposed as a treatment of mitral valve regurgitation is the surgical bow tie method, which recently has been adapted into a minimally invasive catheter based treatment where an implant is used to clip the valve leaflets together. This procedure is more fully disclosed in the scientific and patent literature, such as in U.S. Pat. No. 6,629,534 to St. Goar et al., the entire contents of which are incorporated herein by reference.

Other relevant publications include U.S. Patent Publication No. 2011/0015731 to Carpentier et al. and WO 2011137531 to Lane et al. While some of these devices and methods are promising, there still is a need for improved devices and methods that will further allow more accurate positioning of a prosthetic valve and that will also more securely anchor the valve in place. In addition to needing improved devices, there is also a need for improved delivery systems and improved tools or devices and methods for loading the devices onto their respective delivery systems. At least some of these objectives will be met by the exemplary embodiments disclosed herein.

SUMMARY OF THE INVENTION

The present invention generally relates to medical devices and methods, and more particularly relates to devices and methods for loading a prosthesis onto a delivery system. The prosthesis may be any device but in preferred embodiments is used to treat valve insufficiency, such as mitral insufficiency, also referred to as mitral regurgitation. The delivery system may be any system used to deliver the prosthesis either by traditional surgical implantation methods, or by less invasive percutaneous catheter or minimally invasive transapical methods. While the present disclosure focuses on fixtures for loading the prosthesis onto a delivery system, this is not intended to be limiting. The prosthetic valves disclosed herein may also be used to treat other body valves including other heart valves or venous valves. Exemplary heart valves include the aortic valve, the triscupsid valve, or the pulmonary valve. The loading devices disclosed herein may be used to load any prosthesis onto any delivery system.

In a first aspect of the present invention, a device for loading a prosthesis onto a delivery system comprises a first housing comprising a first inlet, a first outlet, and a first central bore extending therebetween. The first housing has one or more actuators configured to actuate radially inward or outward, and the one or more actuators are adapted to selectively compress a discrete portion of the prosthesis radially inward when the prosthesis is disposed in the first central bore and while adjacent portions of the prosthesis remain uncompressed by the one or more actuators.

The first central bore may comprise a constant diameter region or a first tapered region adapted to radially collapse the prosthesis from a first initial diameter to a smaller diameter when the prosthesis is passed therethrough. The one or more actuators may comprise three actuators circumferentially disposed around the first housing about every 120 degrees. The one or more actuators may be operably coupled together such that they are actuated simultaneously. The device may further comprise a collar that is threadably engaged with the first housing. Rotating the collar actuates the one or more actuators. The one or more actuators may comprise spring loaded actuators biased to return to a position disposed radially outward from the first central bore. The first housing may further comprise a plurality of engagement elements for engaging an adjacent housing. The device may also include a support element that is releasably engaged with the first housing. The inner support element may be configured to support an inner surface of the prosthesis.

The device may further comprise a second housing coupleable end-to-end with the first housing. The second housing may comprise a second inlet, a second outlet, and a second central bore extending therebetween. The second central bore may have a second tapered region that is adapted to radially collapse the prosthesis from a second initial diameter to a second smaller diameter as the prosthesis is advanced through the second central bore. The second central bore may further comprise a second constant diameter region in communication with the first central bore and proximal thereof The second central bore may further comprise a filleted region disposed between the second tapered region and the second constant diameter region. The second central bore may be at least partially cylindrically shaped. The second housing may comprise a plurality of engagement elements for releasably engaging the second housing with an adjacent housing, or a plurality of engagement receptacles for receiving engagement elements on an adjacent housing. The plurality of engagement elements may comprise three engagement tabs arranged circumferentially around the first housing approximately every 120 degrees. Passage of the prosthesis through the second central bore may shape the prosthesis to have a circular cross-section.

The device may further comprise a third housing coupleable end-to-end with the first or the second housing. The third housing may comprise a third inlet, a third outlet, and a third central bore extending therebetween and in communication with the first central bore or the second central bore. The third central bore may have a third tapered region adapted to radially collapse the prosthesis from a third diameter to a diameter smaller than the third diameter as the prosthesis is advanced through the third central bore. The third central bore may further comprise a third constant diameter region in communication with the third tapered region and distal thereto. The third central bore may also comprise a filleted region disposed between the third tapered region and the third constant diameter region. The third central bore may be at least partially cylindrically shaped. The third housing may comprise a plurality of engagement elements for releasably engaging an adjacent housing. The third housing may comprise a plurality of engagement receptacles for receiving engagement elements on an adjacent housing. The plurality of engagement elements may comprise three engagement tabs arranged circumferentially around the first housing approximately every 120 degrees. Passage of the prosthesis through the third central bore may shape the prosthesis to have a circular cross-section.

The prosthesis may comprise a prosthetic heart valve, and may comprise a plurality of anchoring tabs, and wherein actuation of the one or more actuators is adapted to move the plurality of anchoring tabs radially inward. The plurality of anchoring tabs may be adapted to be releasably engaged with retaining features on the delivery catheter. The plurality of anchoring tabs may comprise commissure posts on a prosthetic heart valve.

In another aspect of the present invention, a system for loading a prosthesis onto a delivery system comprises the loading device described above in addition to a prosthetic heart valve and a delivery device.

In still another aspect of the present invention, a method for loading a prosthesis onto a delivery system comprises providing a prosthetic valve having a plurality of commissure posts coupled thereto, wherein the prosthetic valve comprises an unbiased diameter, and reducing the unbiased diameter of the prosthetic valve in selected discrete regions, the selected discrete regions comprising the commissure posts. The method also includes loading the reduced diameter prosthetic valve onto a delivery device.

Reducing the unbiased diameter of the prosthetic valve may comprise actuating one or more actuators on a first housing, wherein the one or more actuators may selectively engage discrete regions of the prosthetic valve. The method may further comprise passing the prosthetic valve through a constant diameter portion of a central channel in the first housing. Actuating the one or more actuators may comprise depressing one or more pins or fingers radially inward to engage the discrete regions of the prosthetic valve. The discrete regions may move radially inward into a reduced profile. Depressing may comprise simultaneously depressing the one or more pins or fingers.

The method may further comprise reducing diameter of the prosthetic valve from the unbiased diameter to a first diameter less than the unbiased diameter. Reducing diameter of the prosthetic valve from the unbiased diameter to the first diameter may comprise passing the prosthetic valve through a tapered central channel. Passing the prosthetic valve through the tapered central channel may comprise pushing or pulling the prosthetic valve therethrough. Passing the prosthetic valve through the tapered central channel may comprise shaping the prosthetic valve to have a circular cross-section.

The method may further comprise reducing diameter of the prosthetic valve from the first diameter to a second diameter less than the first diameter. Reducing diameter from the first diameter to the second diameter may comprise passing the prosthetic valve through a second tapered central channel. Passing the prosthetic valve through the second tapered central channel may comprise pushing or pulling the prosthetic valve therethrough.

The delivery device may comprise an inner shaft and an outer shaft slidably disposed thereover, and loading the reduced diameter prosthetic valve may comprise disposing the prosthetic valve between the inner shaft and outer shafts. Loading the reduced diameter prosthetic valve may comprise releasably engaging the commissure posts with the delivery device.

The prosthetic valve may be fabricated from a nickel titanium alloy, and the method may further comprise cooling the prosthetic valve to a temperature less than or equal to the austenitic finish temperature of the prosthetic valve. Cooling the prosthetic valve may comprise cooling the prosthetic valve in chilled saline. The diameter of the prosthetic valve may be reduced from the unbiased diameter to the first diameter in a first housing, and the diameter of the prosthetic valve may be reduced from the first diameter to the second diameter in a second housing, and the method may further comprise coupling the first housing with the second housing. The first housing and the second housing may be uncoupled from one another after the diameter has been reduced to the first diameter. The method may also comprise supporting an inner surface of the prosthesis with a support element.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 11A-11D illustrate an exemplary embodiment of a delivery system used to transapically deliver a prosthetic cardiac valve.

FIGS. 29A-29B illustrate the loading system of FIG. 27 after actuation.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 1:
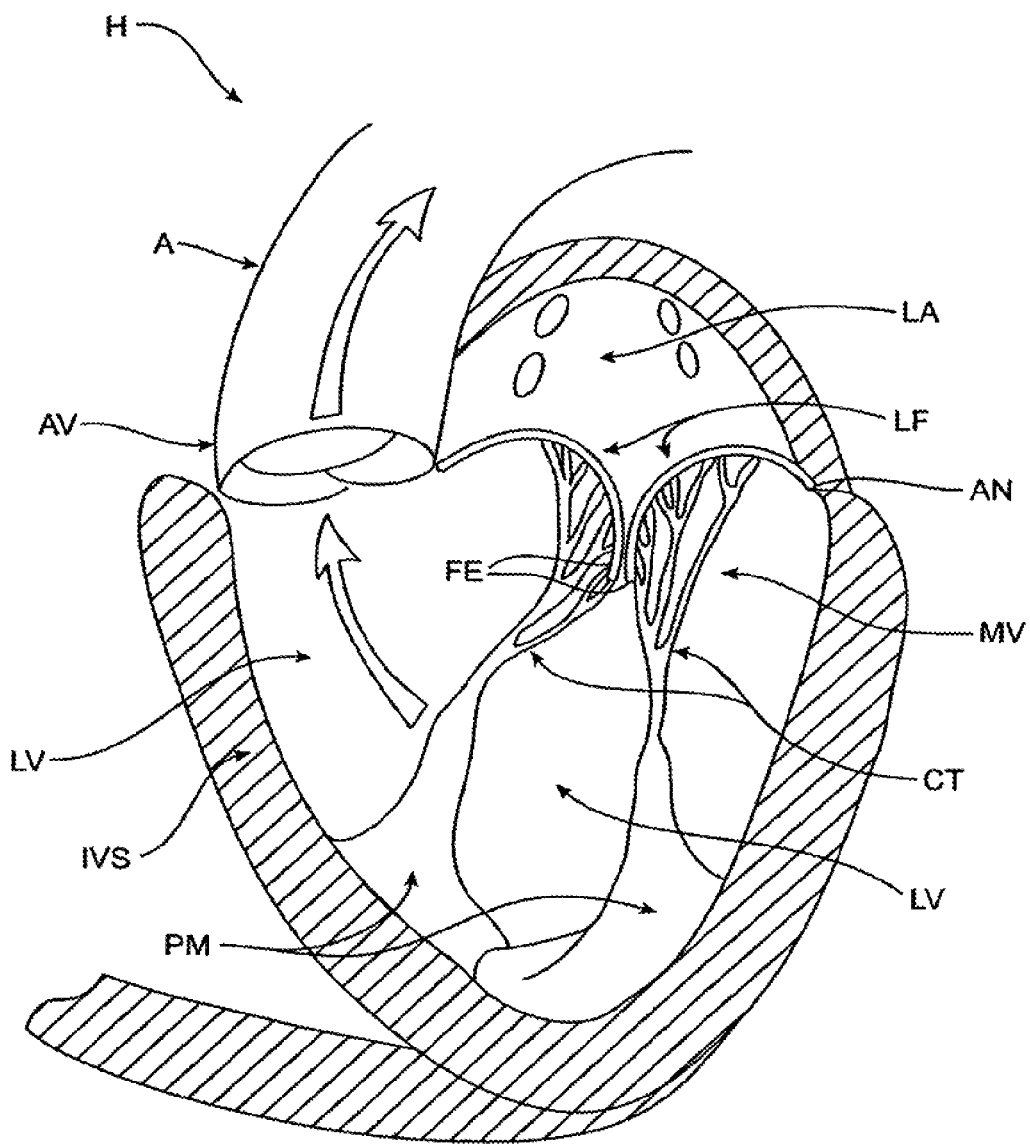
FIG. 1 is a schematic illustration of the left ventricle of a heart showing blood flow during systole with arrows.

Cardiac Anatomy. The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
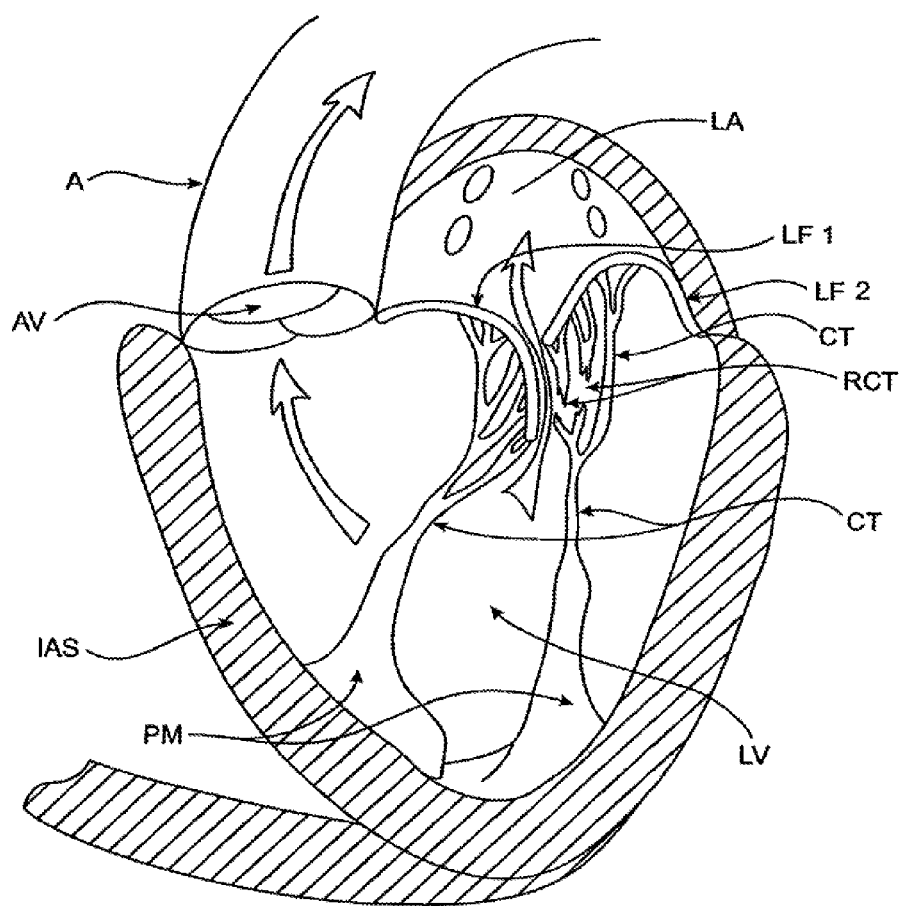
FIG. 2 is a schematic illustration of the left ventricle of a heart having prolapsed leaflets in the mitral valve.
Figure 3:
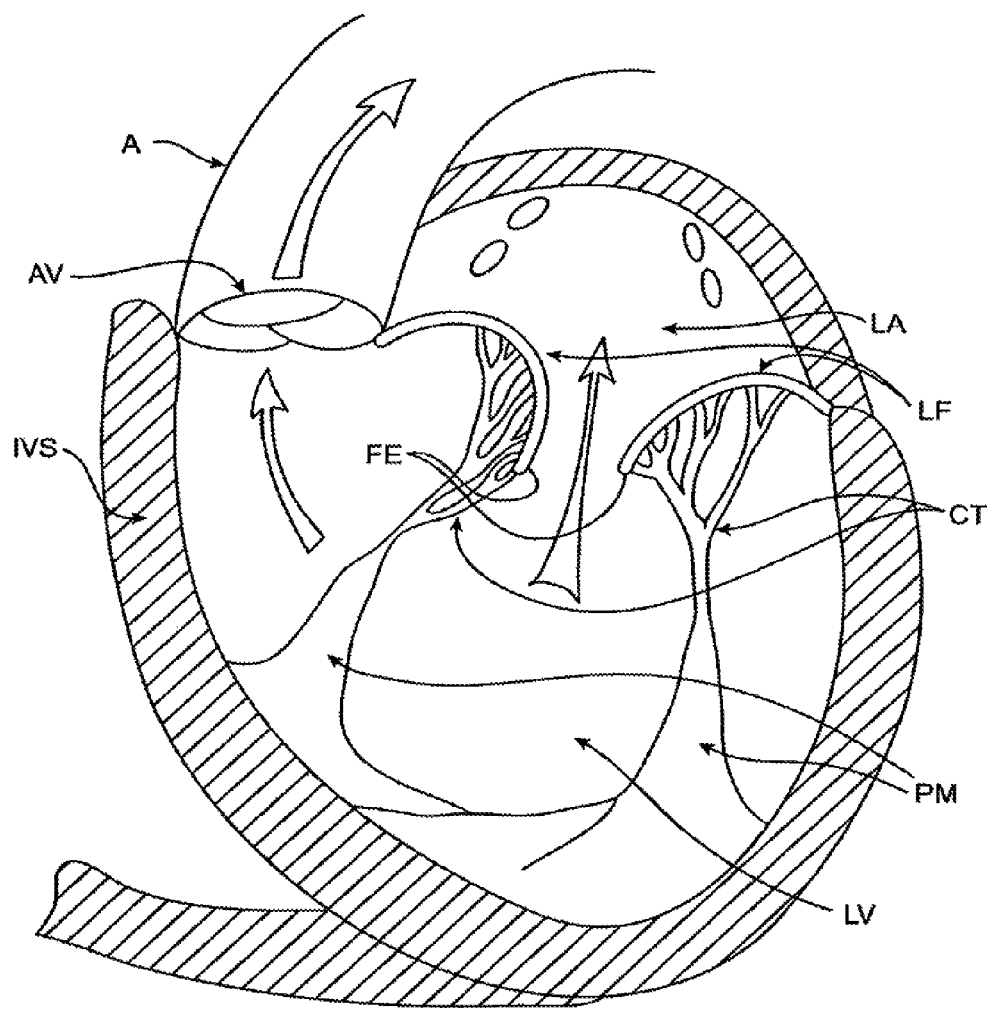
FIG. 3 is a schematic illustration of a heart in a patient suffering from cardiomyopathy where the heart is dilated and the leaflets do not meet.
Figure 4:
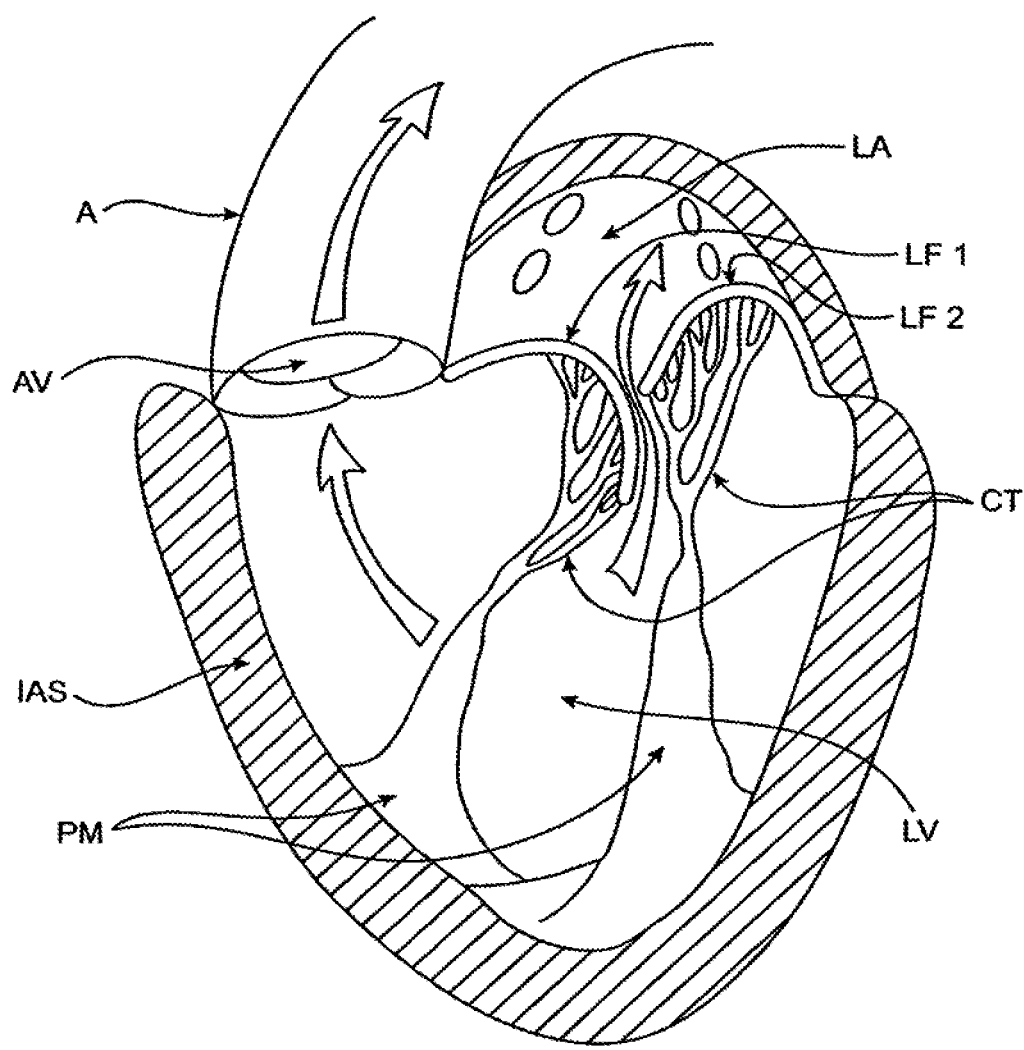
FIG. 4 illustrates mitral valve regurgitation in the left ventricle of a heart having impaired papillary muscles.

Referring now to FIGS. 2-4, a number of structural defects in the heart can cause mitral valve regurgitation. Ruptured chordae RCT, as shown in FIG. 2, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
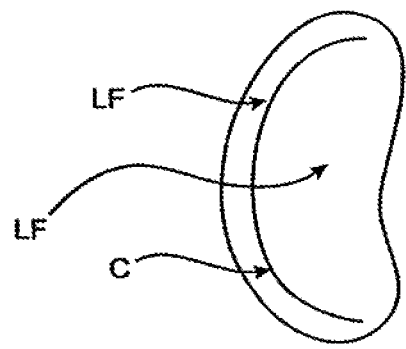
FIG. 3A shows normal closure of the valve leaflets.
Figure 3B:
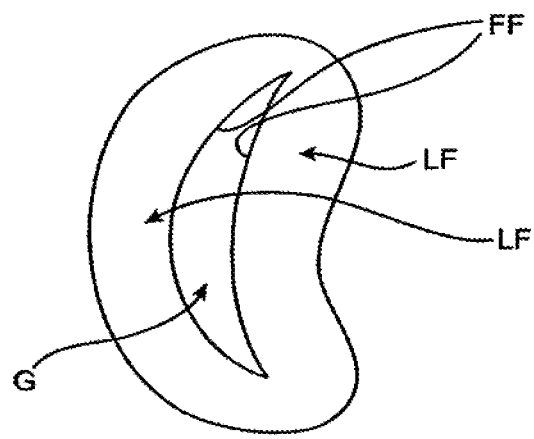
FIG. 3B shows abnormal closure of the valve leaflets.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
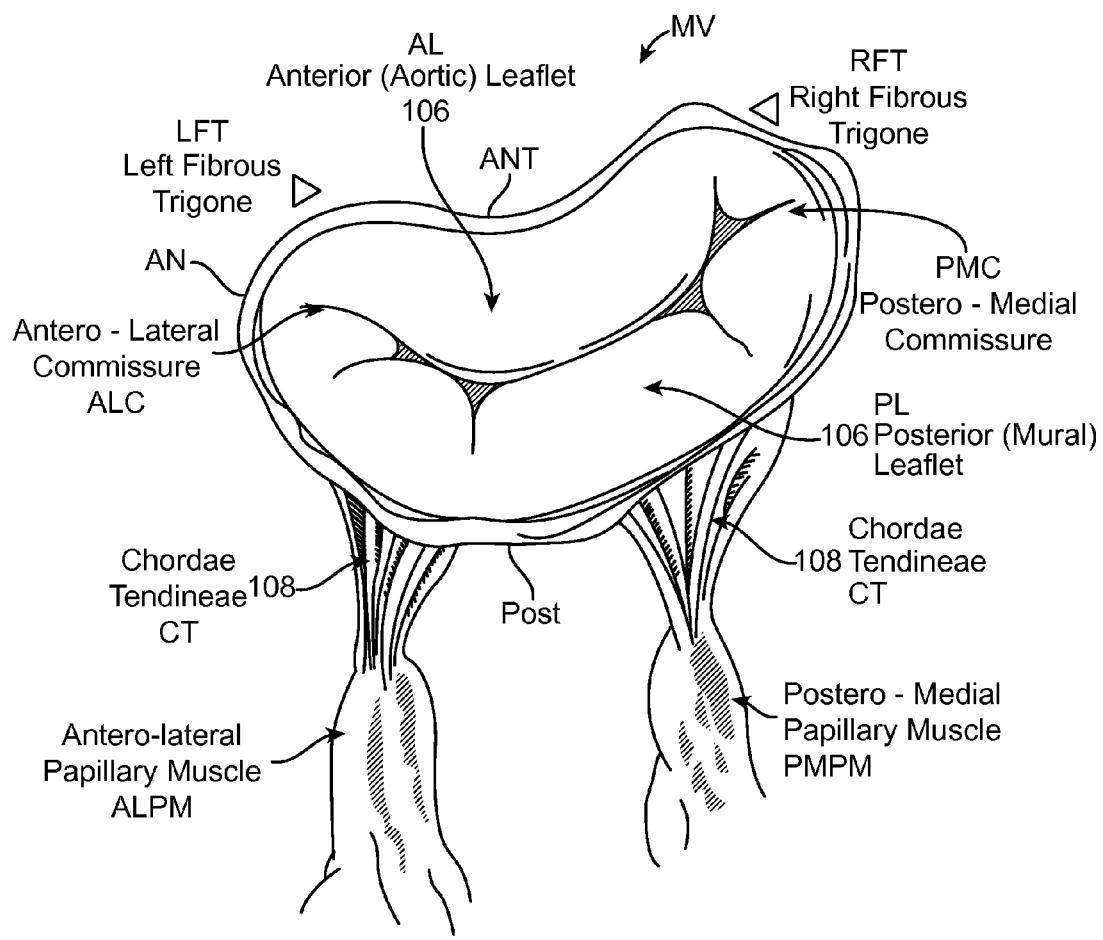
FIGS. 5A-5B illustrate anatomy of the mitral valve.
Figure 5B:
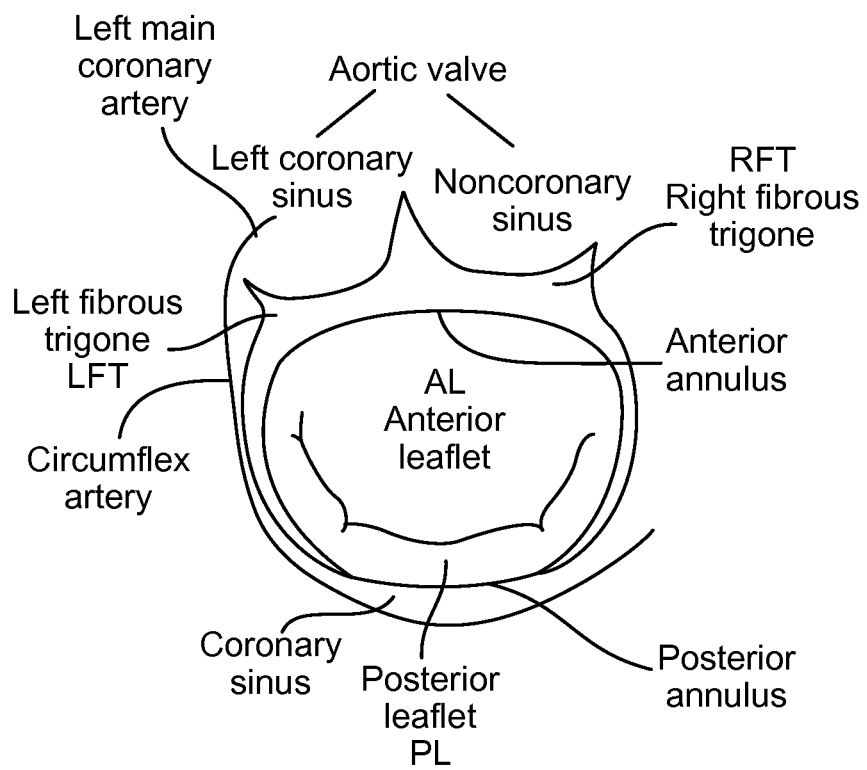

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices, delivery systems, loading fixtures, and methods for treating mitral regurgitation. While the embodiments disclosed herein are directed to an implantable prosthetic mitral valve for treating mitral regurgitation, one of skill in the art will appreciate that this is not intended to be limiting, and the devices and methods disclosed herein may also be used to treat other cardiac valves such as the tricuspid valve, aortic valve, pulmonary valve, etc, as well as other valves in the body such as venous valves.

Prosthetic Valve. Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue, or combinations thereof. The prosthetic valve once implanted, takes over for malfunctioning native valve, thereby reducing or eliminating valvar insufficiency. While some of these valves appear promising, there still is a need for improved valves. Positioning and anchoring the prosthetic valve in the native anatomy remains a challenge. The following discloses exemplary embodiments of a prosthetic valve, a delivery system for the prosthetic valve, and methods of delivering the valve that overcome some of the challenges associated with existing prosthetic valves.

Figure 6:
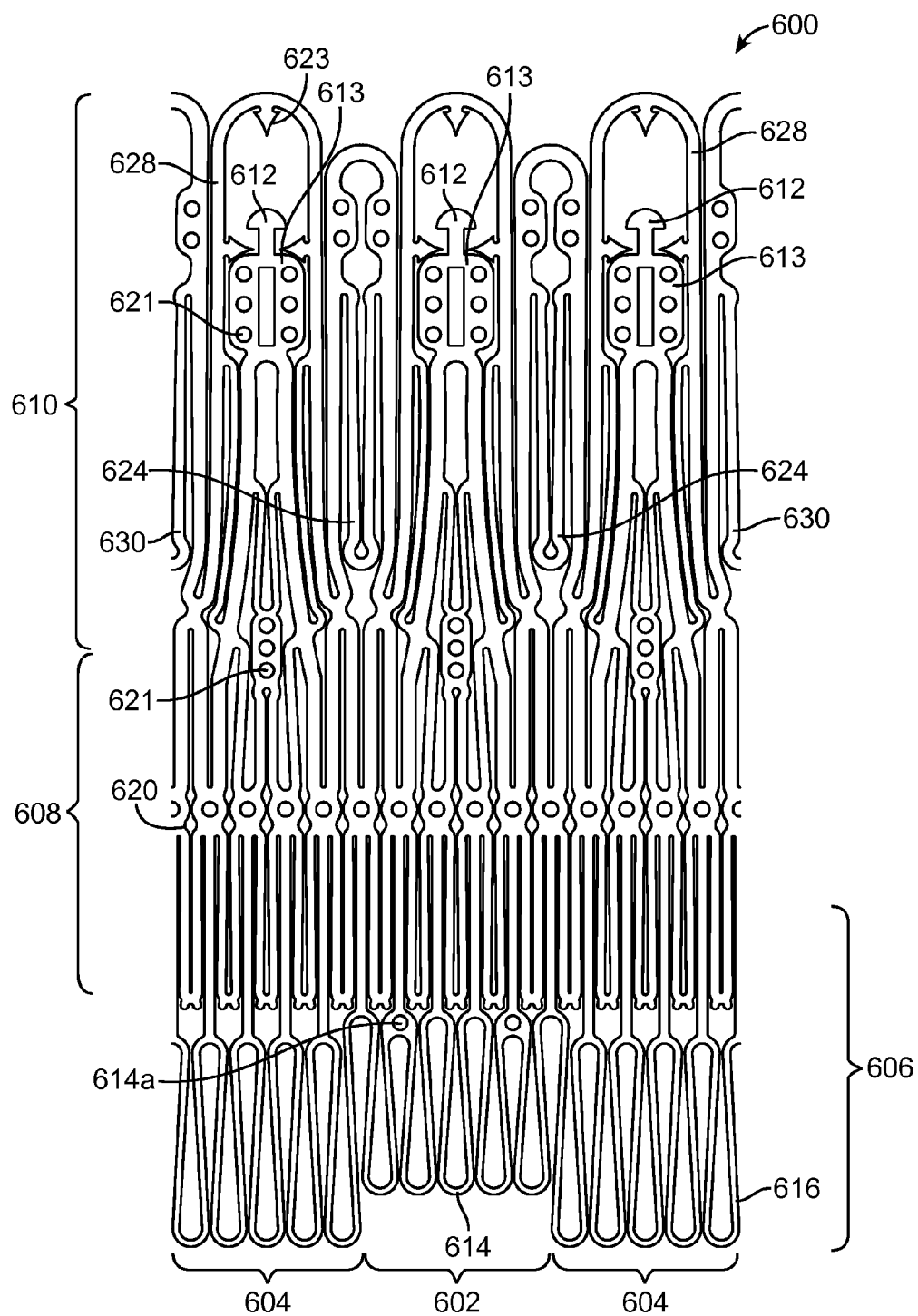
FIG. 6 illustrates an exemplary embodiment of an uncovered frame in a prosthetic cardiac valve, with the frame flattened out and unrolled.

FIG. 6 illustrates an exemplary embodiment of a prosthetic cardiac valve in the collapsed configuration. Coverings from the frame (e.g. fabric or tissue) has been removed to permit observation of the underlying frame 600. The frame has been unrolled and flattened out. The prosthetic valve frame 600 has an atrial region 606, an annular region 608, and a ventricular region 610. The frame 600 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and exapandable members may also be used to expand the frame when plastic deformation (e.g. balloon expansion) is required to open the frame.

Atrial region 606 has a skirt 616 which includes a plurality of interconnected struts that form a series of peaks and valleys. In this region, the struts are skew relative to one another and thus the resulting cell pattern has an enlarged end and the opposite end tapers to a smaller end. In preferred embodiments, the anterior portion of the atrial skirt does not have a flanged region like the posterior portion, thus the anterior portion 602 of the atrial region may have shorter struts than the posterior region 604. Thus the peaks and valleys in the anterior portion are axially offset from those in the remaining posterior portion of the atrial region. This may be advantageous as it prevents the struts in the anterior portion of the atrial skirt from protruding upwards potentially impinging against the left atrium and causing perforations. Additionally, the shortened struts and offset peaks and valleys form an alignment element 614 that can assist the physician visualize delivery of the prosthetic valve to the mitral valve and alignment of the prosthetic valve prior to expansion of the prosthetic valve. Optional radiopaque markers 614a are disposed on either side of the offset peaks and valleys and further help with visualization during implantation of the valve. The atrial region preferably self-expands to either a cylindrical shape, or it may have a D-shaped cross-section where the anterior portion 602 is substantially flat, and the posterior portion 604 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 608 with connecting struts which are preferably linear and substantially parallel to the longitudinal axis of the frame.

The annular region 608 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 610.

The ventricular region 610 also includes a plurality of interconnected struts that form peaks and valleys. Additionally, the struts in the ventricular region form the leaflet commissures 613 which are covered with fabric, pericardial tissue, or other materials to form the prosthetic valve leaflets. Holes in the commissures allow suture to be attached thereto. Struts in the ventricular region also form a ventricular skirt 628 which expands outward to engage the anterior and posterior mitral valve leaflets, and struts in the ventricular region also form the anterior tabs 624 and the posterior tab 630. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 624, 630 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward. Further retraction of the constraining sheath then allows the remainder of the posterior tab to finish its radial expansion, and finally the ventricular skirt will radially expand outward. While strut lengths and axial position of the posterior tab and the ventricular skirt are similar, internal struts connect the ventricular skirt with the commissures, and this delays expansion of the ventricular skirt slighltly, thus the posterior tab finishes expansion before the ventricular skirt. Using this sequence of deploying the prosthetic valve may allow the valve to more accurately delivered and also more securely anchored into position.

Suture holes 621 are disposed along the struts of the annular region as well as the ventricular region to allow attachment of a cover such as pericardium or a polymer such as Dacron or ePTFE. The suture holes may also be disposed along any other part of the frame. Barbs 623 are disposed along the ventricular skirt 628 to help anchor the prosthetic valve to adjacent tissue. Commissure tabs or tabs 612 are disposed on the tips of the commissures 613 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting.

The frame may be formed by EDM, laser cutting, photochemical etching, or other techniques known in the art. Hypodermic tubing or flat sheets may be used to form the frame. Once the frame has been cut and formed into a cylinder, it may be radially expanded into a desired geometry and heat treated using known processes to set the shape. Thus, the prosthetic valve may be loaded onto a delivery catheter in a collapsed configuration and constrained in the collapsed configuration with a constraining sheath. Removal of the constraining sheath will allow the anchor to self-expand into its unbiased pre-set shape. In other embodiments, an expandable member such as a balloon may be used to radially expand the anchor into its preferred expanded configuration.

Figure 7:
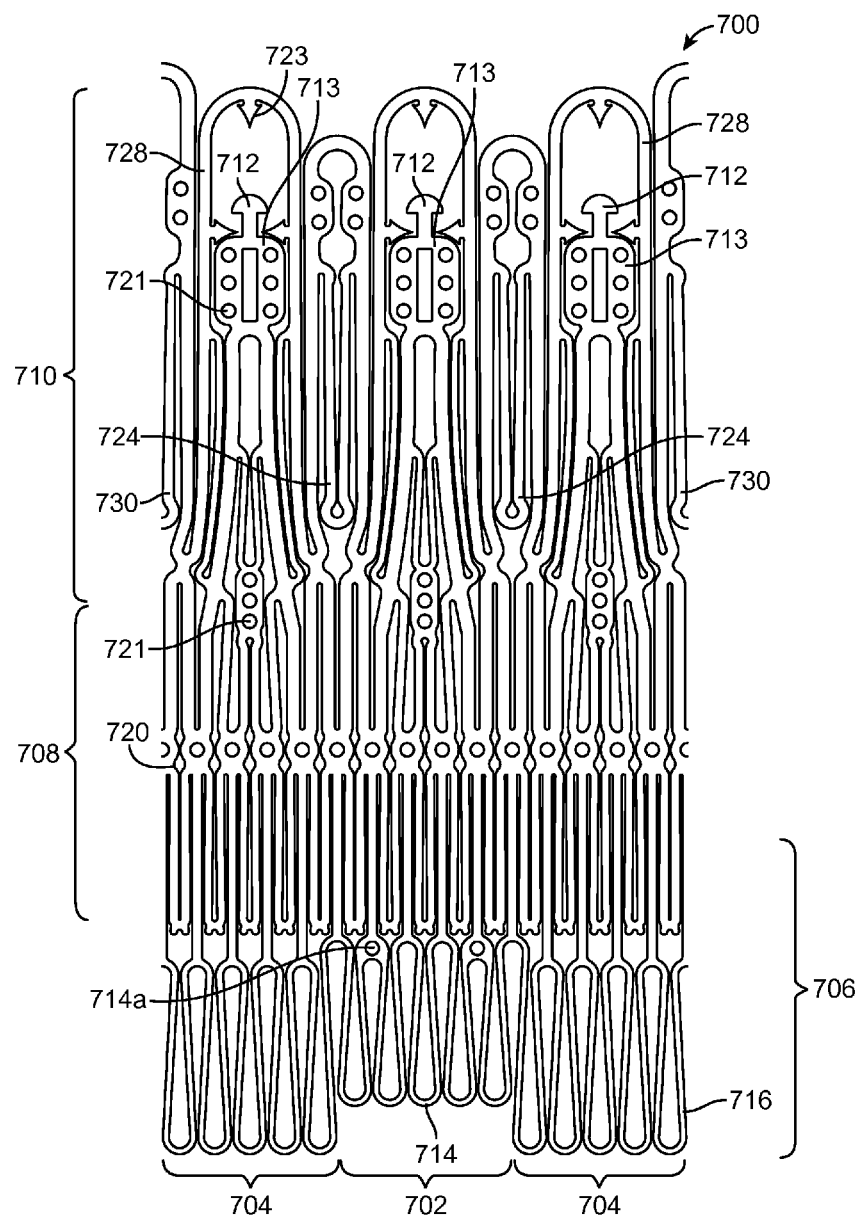
FIG. 7 illustrates another exemplary embodiment of an uncovered frame in a prosthetic cardiac valve, with the frame flattened out and unrolled.

FIG. 7 illustrates another exemplary embodiment of a prosthetic cardiac valve in the collapsed configuration, and similar to the previous embodiment with the major difference being the strut lengths in the anterior tabs, posterior tab, and ventricular skirt. Varying the strut lengths allow the sequence of expansion of the anterior and posterior tabs and ventricular skirt to be controlled. Coverings from the frame (e.g. fabric or tissue) has been removed to permit observation of the underlying frame 700. The frame has been unrolled and flattened out. The prosthetic valve frame 700 has an atrial region 706, an annular region 708, and a ventricular region 710. The frame 700 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and exapandable members may also be used to expand the frame when plastic deformation (e.g. balloon expansion) is required to open the frame.

Atrial region 706 has a skirt 716 which includes a plurality of interconnected struts that form a series of peaks and valleys. In this region, the struts are skew relative to one another and thus the resulting cell pattern has an enlarged end and the opposite end tapers to a smaller end. An anterior portion 702 of the atrial region has shorter struts than the posterior region

704. Thus the peaks and valleys in the anterior portion are axially offset from those in the remaining posterior portion of the atrial region. This allows creation of an alignment element 714 to help the physician deliver the prosthetic valve to the mitral valve and align the prosthetic valve prior to expansion of the prosthetic valve. Other aspects of the atrial region 706 are similar to those of the atrial region 606 in FIG. 6. Optional radiopaque markers 714a are disposed on either side of the offset peaks and valleys and help with visualization during implantation of the valve. The atrial region preferably self-expands to either a cylindrical shape, or it may have a D-shaped cross-section where the anterior portion 702 is substantially flat, and the posterior portion 704 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 708 with connecting struts which are preferably linear and substantially parallel to the longitudinal axis of the frame.

The annular region 708 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 710.

The ventricular region 710 also includes a plurality of interconnected struts that form peaks and valleys. Additionally, the struts in the ventricular region form the leaflet commissures 713 which are covered with fabric, pericardial tissue, or other materials to form the prosthetic valve leaflets. Holes in the commissures allow suture to be attached thereto. Struts in the ventricular region also form a ventricular skirt 728 which expands outward to engage the anterior and posterior mitral valve leaflets, and struts in the ventricular region also form the anterior tabs 724 and the posterior tab 730. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 724, 730 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the ventricular skirt to radially expand, and finally further retraction of the sheath allows the remainder of the posterior tab to finish it's radial expansion. Using this sequence of deploying the prosthetic valve may allow the valve to more accurately be delivered and also more securely anchored into position.

Suture holes 721 are disposed along the struts of the annular region as well as the ventricular region to allow attachment of a cover such as pericardium or a polymer such as Dacron or ePTFE. The suture holes may also be disposed along any other part of the frame. Barbs 723 are disposed along the ventricular skirt 728 to help anchor the prosthetic valve to adjacent tissue. Commissure tabs or tabs 712 are disposed on the tips of the commissures 713 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting. The frame may be formed similarly as described above with respect to FIG. 6.

Figure 8:
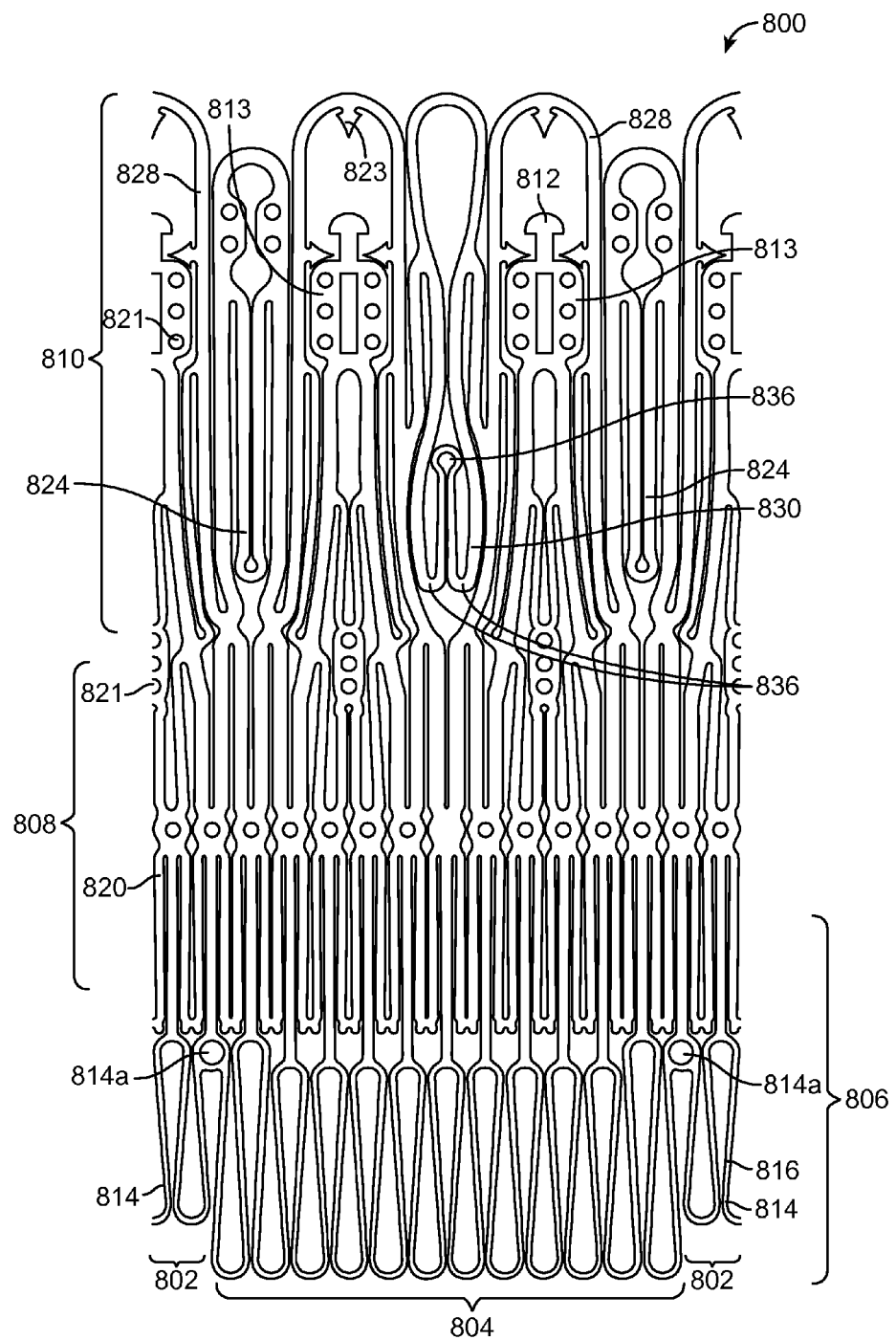
FIG. 8 illustrates still another exemplary embodiment of an uncovered frame in a prosthetic cardiac valve, with the frame flattened out and unrolled.

FIG. 8 illustrates another exemplary embodiment of a prosthetic cardiac valve in the collapsed configuration, and is similar to the previous embodiments, with the major difference being that the posterior tab is designed to expand to form an elongate horizontal section which allows engagement and anchoring of the posterior tab with the sub-annular region between the posterior leaflet and the ventricular wall. Thus, the elongate horizontal section contacts a larger region of the sub-annular region as compared with a posterior tab that only has a tapered tip formed from a single hinge between struts. This provides enhanced anchoring of the prosthetic valve. In this exemplary embodiment, the anterior tabs will completely self-expand first, followed by the posterior tab and then the ventricular skirt. However, in some situations external factors such as the delivery system, anatomy, etc. may alter the sequence of expansion, and therefore this is not intended to be limiting. Coverings from the frame (e.g. fabric or tissue) have been removed to permit observation of the underlying frame 800. The frame has been unrolled and flattened out. The prosthetic valve frame 800 has an atrial region 806, an annular region 808, and a ventricular region 810. The frame 800 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and exapandable members may also be used to expand the frame when plastic deformation (e.g. balloon expansion) is required to open the frame.

Atrial region 806 has a skirt 816 which includes a plurality of interconnected struts that form a series of peaks and valleys. In this region, the struts are skew relative to one another and thus the resulting cell pattern has an enlarged end and the opposite end tapers to a smaller end. An anterior portion 802 of the atrial region has shorter struts than the posterior region 804. Thus the peaks and valleys in the anterior portion are axially offset from those in the remaining posterior portion of the atrial region. This allows creation of an alignment element 814 to help the physician deliver the prosthetic valve to the mitral valve and align the prosthetic valve prior to expansion of the prosthetic valve. Other aspects of the atrial region 806 are similar to those of the atrial region 606 in FIG. 6. Optional radiopaque markers 814a are disposed on either side of the offset peaks and valleys and help with visualization during implantation of the valve. The atrial region preferably self-expands to either a cylindrical shape, or it may have a D-shaped cross-section where the anterior portion 802 is substantially flat, and the posterior portion 804 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 808 with connecting struts which are preferably linear and substantially parallel to the longitudinal axis of the frame.

The annular region 808 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded into engagement with the mitral valve annulus. Connector struts join the annular region with the ventricular region 810.

The ventricular region 810 also includes a plurality of interconnected struts that form peaks and valleys. Additionally, the struts in the ventricular region form the leaflet commissures 813 which are covered with fabric, pericardial tissue, or other materials to form the prosthetic valve leaflets. Holes in the commissures allow suture to be attached thereto. Struts in the ventricular region also form a ventricular skirt 828 which expands outward to engage the anterior and posterior mitral valve leaflets, and struts in the ventricular region also form the anterior tabs 824 and the posterior tab 830. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below. The posterior tab is similar to the posterior tabs described above in FIGS. 6-7, except that in this embodiment, the posterior tab comprises four interconnected struts as opposed to two interconnected struts. Thus, in this embodiment the plurality of interconnected struts form three hinged regions 836 along the tab. Upon expansion of the posterior tab, the hinged regions will also expand, thereby forming an elongate horizontal section which allows engagement and anchoring of the posterior tab with the sub-annular region between the posterior leaflet and the ventricular wall. This may help position and anchor the prosthetic valve better than posterior tabs which only have a smaller footprint or a single tapered tip for engagement with the posterior portion of the mitral valve. The posterior leaflet in this embodiment, may be substituted with any of the other posterior tabs described in this specification.

By controlling strut length or axial position of the anterior or posterior tabs along the frame, deployment of the tabs may be controlled. Thus in this exemplary embodiment, because the length of the struts in the anterior tabs and posterior tabs 824, 830 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the remainder of the posterior tab to finish self-expanding, followed by self-expansion of the ventricular skirt. Using this sequence of deploying the prosthetic valve may allow the valve to more accurately be delivered and also more securely anchored into position.

Suture holes 821 are disposed along the struts of the annular region as well as the ventricular region to allow attachment of a cover such as pericardium or a polymer such as Dacron or ePTFE. The suture holes may also be disposed along any other part of the frame. Barbs 823 are disposed along the ventricular skirt 828 to help anchor the prosthetic valve to adjacent tissue. Commissure tabs or tabs 812 are disposed on the tips of the commissures 813 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting. The frame may be formed similarly as described above with respect to those previously described above.

Figure 9A:
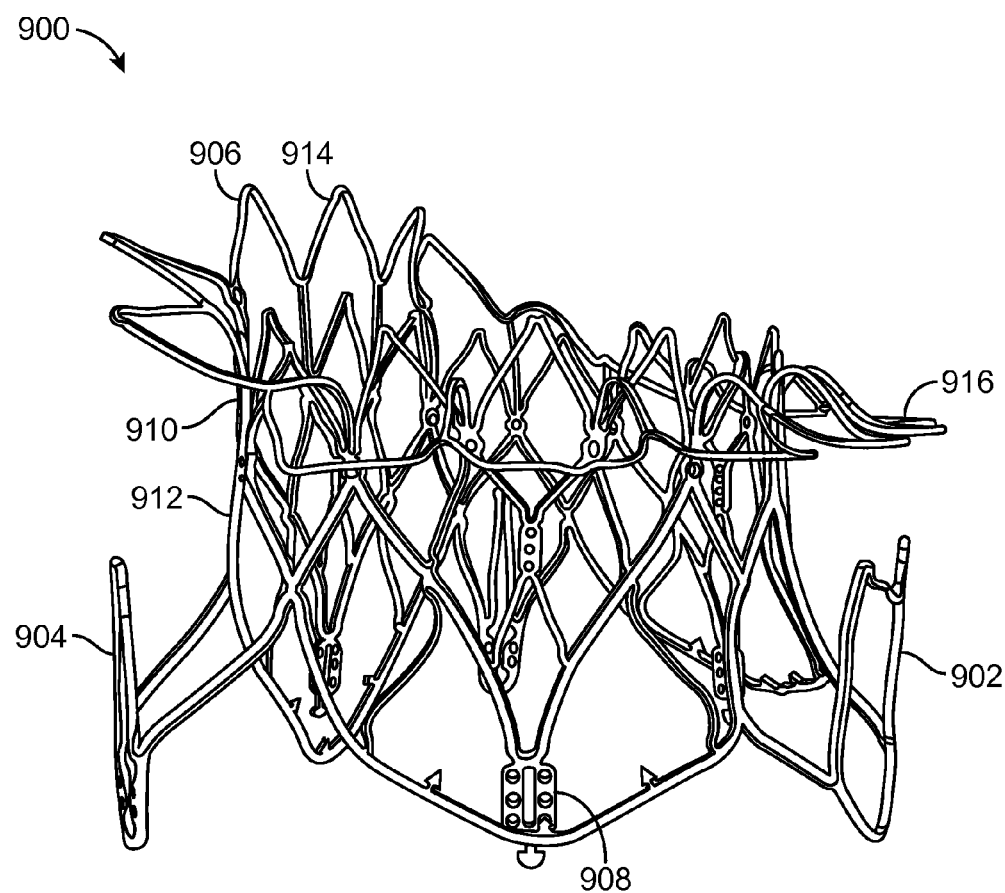
FIG. 9A illustrates a perspective view of an uncovered frame in a prosthetic cardiac valve after it has expanded.
Figure 9B:
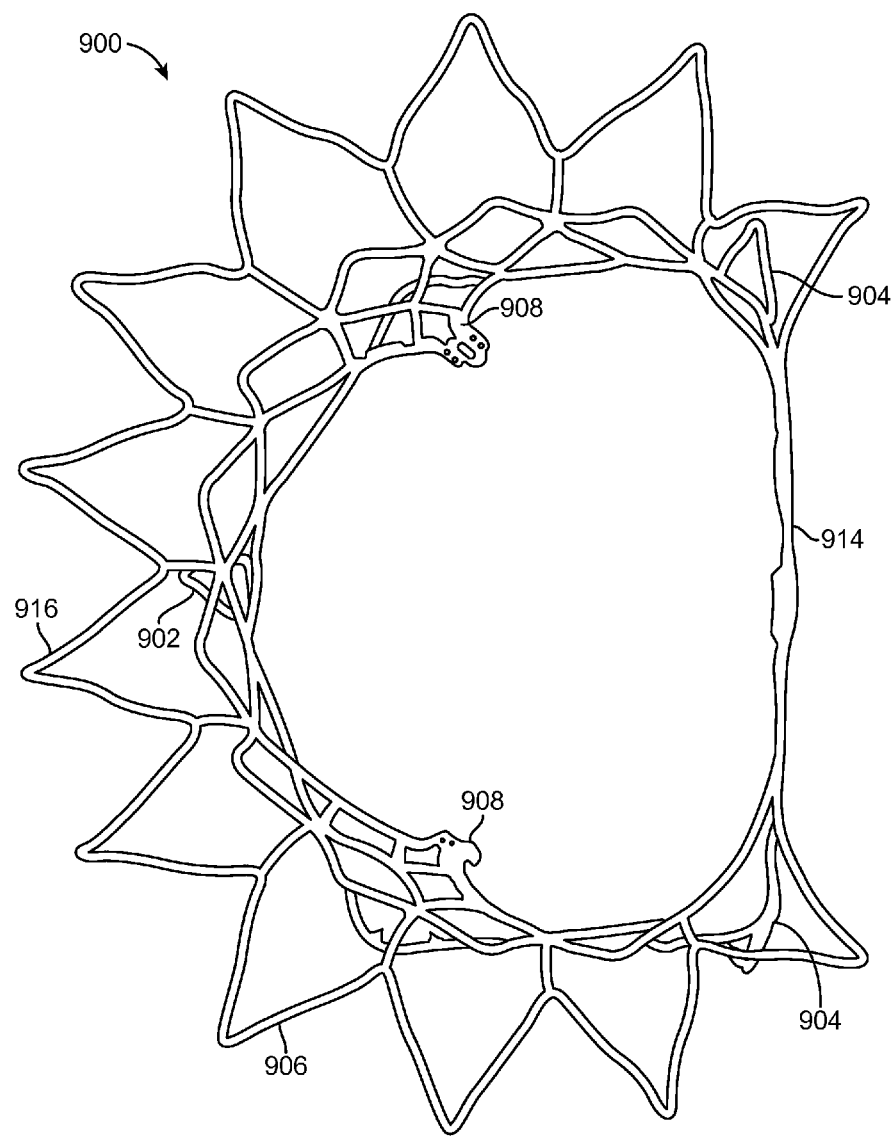
FIG. 9B illustrates a top view of the embodiment in FIG. 9A.

FIG. 9A illustrates the frame 900 of a prosthetic cardiac valve after it has expanded. Any of the frame embodiments described above may take this form as each of the above frames have similar geometry but they expand in different order. The frame includes the atrial skirt 906 with anterior portion 914 and posterior portion 916. A flanged region is formed around the posterior portion and the anterior portion remains flangeless. Additionally, the anterior portion is generally flat, while the posterior portion is cylindrically shaped, thereby forming a D-shaped cross-section which accommodates the mitral valve anatomy. FIG. 9B is a top view of the embodiment in FIG. 9A and more clearly illustrates the D-shaped cross-section.

The frame also includes the annular region 910 and ventricular skirt 912. Anterior tabs 904 (only one visible in this view) is fully expanded such that a space exists between the inner surface of the anterior tab and outer surface of the ventricular skirt. This allows the anterior leaflet and adjacent chordae to be captured therebetween. Similarly, the posterior tab 902 is also fully deployed, with a similar space between the inner surface of the posterior tab 902 and an outer surface of the ventricular skirt. This allows the posterior leaflet and adjacent chordae tendineae to be captured therebetween. The commissure posts 908 are also visible and are disposed in the inner channel formed by the frame. The commissure posts are used to form the prosthetic mitral valve leaflets. The overall shape of the expanded frame is D-shaped, with the anterior portion flat and the posterior portion cylindrically shaped.

Figure 10:
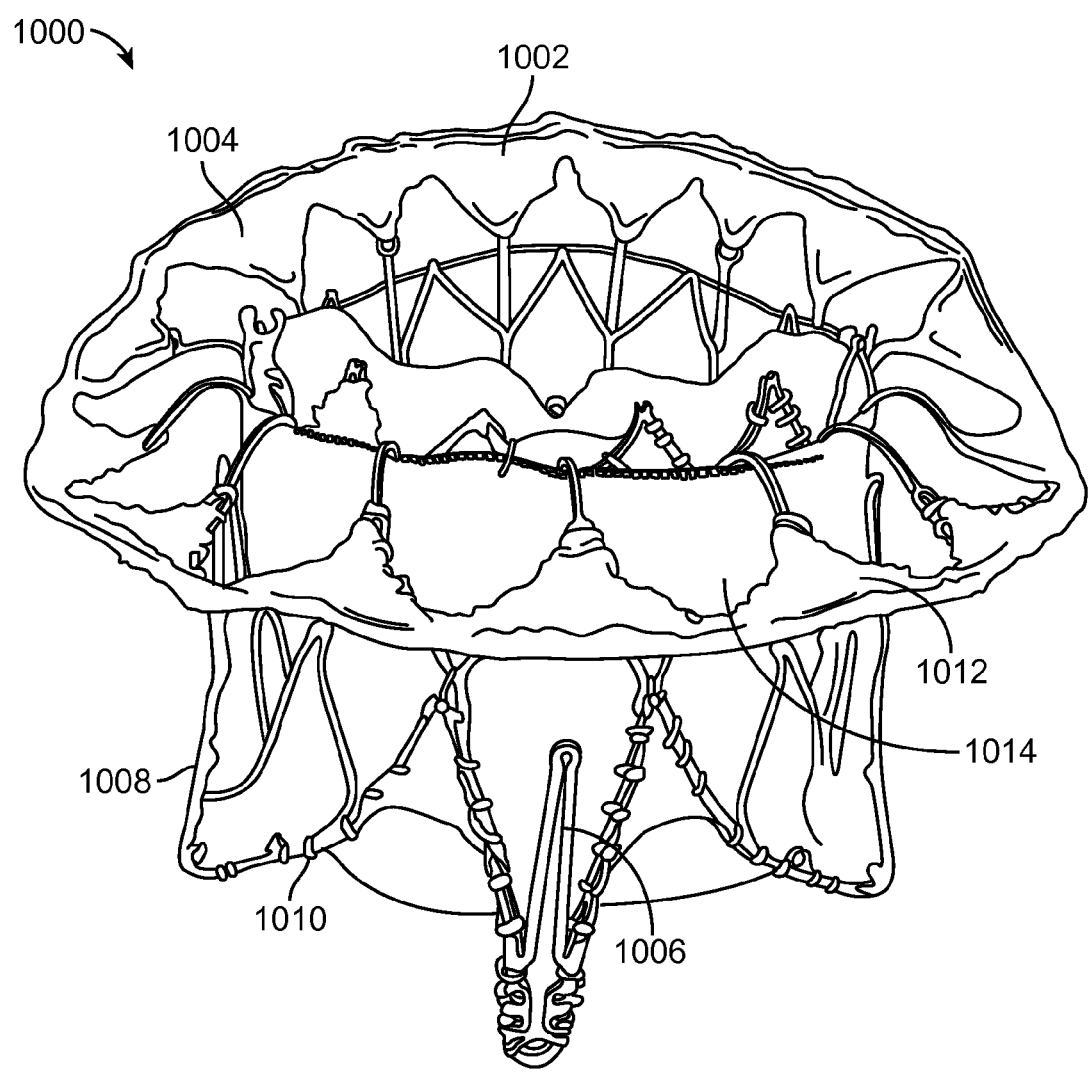
FIG. 10 illustrates the frame of FIG. 9A with the covering thereby forming a prosthetic cardiac valve.

FIG. 10 illustrates the expanded frame covered with a cover 1002 such as pericardial tissue or a polymer such as ePTFE or a fabric like Dacron attached to the frame, thereby forming the prosthetic cardiac valve 1000. The atrial skirt may be entirely covered by a material, or in preferred embodiments, the covering is only disposed between adjacent struts 1012 in adjacent cells in the flanged portion of the atrial skirt. The area 1014 between adjacent struts within the same cell remain uncovered. This allows blood flow to remain substantially uninterrupted while the prosthetic valve is being implanted. Suture 1010 may be used to attach the cover to the frame. In this view, only the posterior tab 1006 is visible on the posterior portion of the prosthetic valve along with ventricular skirt 1008 and atrial skirt 1004.

Delivery System. FIGS. 11A-11D illustrate an exemplary embodiment of a delivery system that may be used to deliver any of the prosthetic cardiac valves disclosed in this specification. While the delivery system is designed to preferably deliver the prosthetic cardiac valve transapically, one of skill in the art will appreciate that it may also be modified so that the prosthetic valve may be delivered via a catheter transluminally, such using a transseptal route. One of skill in the art will appreciate that using a transseptal route may require the relative motion of the various shafts to be modified in order to accommodate the position of the delivery system relative to the mitral valve.

Figure 11A:
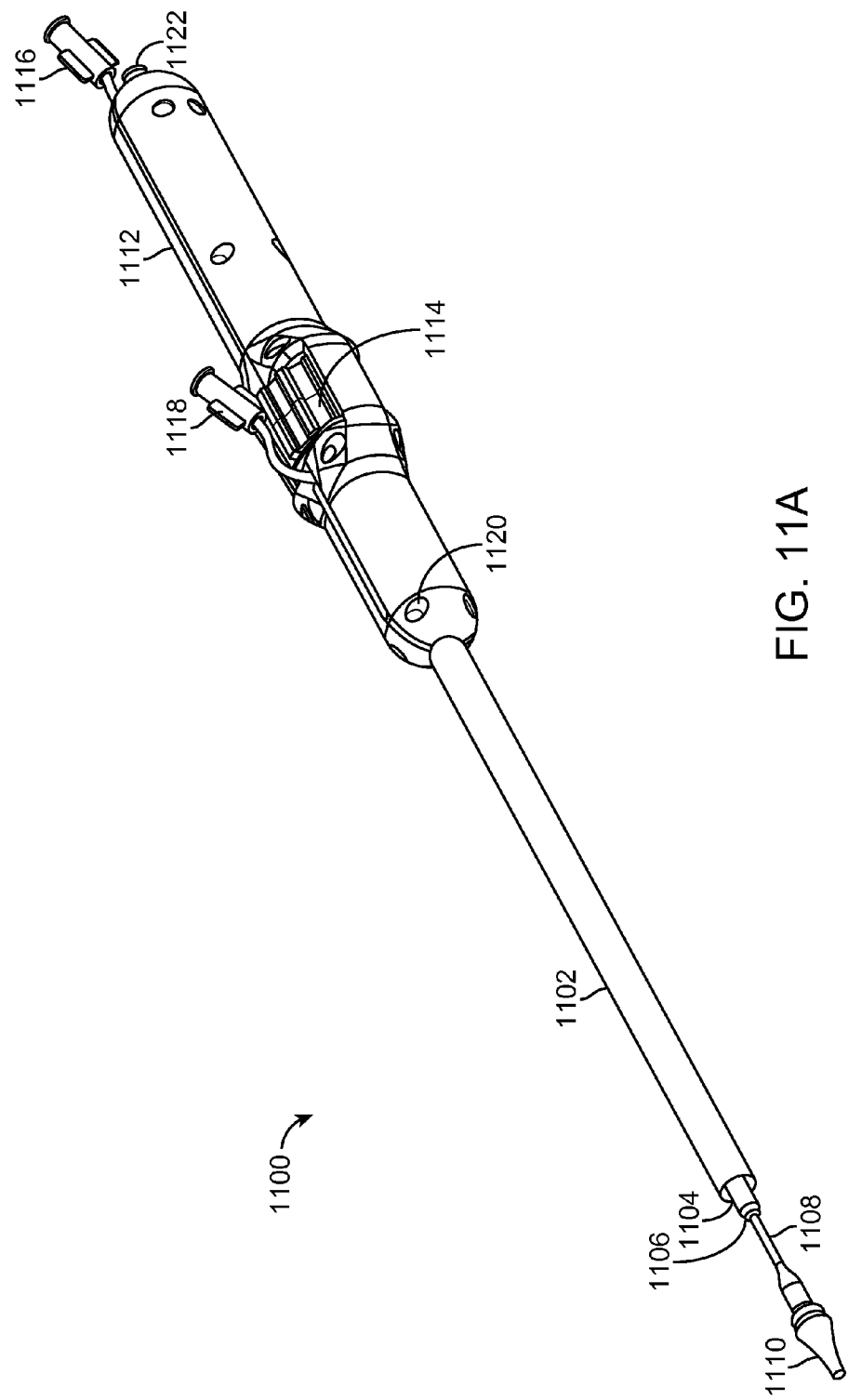
Figure 11B:
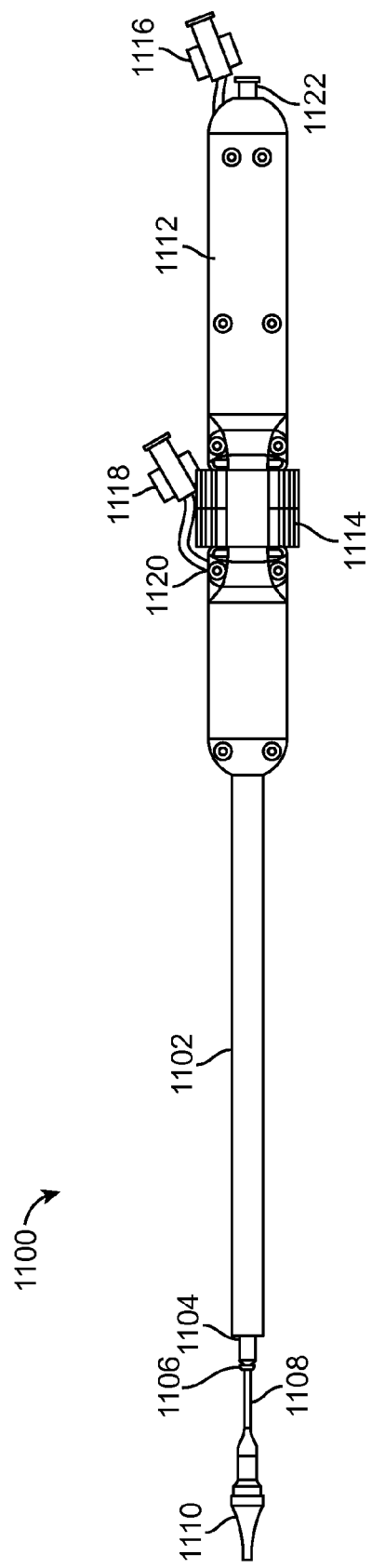

FIG. 11A illustrates a perspective view of delivery system 1100. The delivery system 1100 includes a handle 1112 near a proximal end of the delivery system and a distal tissue penetrating tip 1110. Four elongate shafts are included in the delivery system and include an outer sheath catheter shaft 1102, a bell catheter shaft 1104 which is slidably disposed in the outer sheath catheter shaft 1102, a hub catheter shaft 1106 which remains stationary relative to the other shafts, but the bell catheter shaft slides relative to the hub shaft, and finally an inner guidewire catheter shaft 1108 which is also fixed relative to the other shafts and has a lumen sized to receive a guidewire which passes therethrough and exits the distal tissue penetrating tip. An actuator mechanism 1114 is used to control movement of the various shafts as will be explained in greater detail below, and flush lines 1116, 1118 with luer connectors are used to flush the annular regions between adjacent shafts. Flush line 1118 is used to flush the annular space between the outer sheath catheter shaft 1102 and the bell catheter shaft 1104. Flush line 1116 is used to flush the annular space between the bell catheter 1104 and the hub catheter 1106. The inner guidewire catheter shaft 1108 is stationary relative to the hub catheter 1106 therefore the annular space may be sealed with an o-ring or other material. Luer connector 1122 allows flushing of the guidewire lumen and a hemostatic valve such as a Tuohy-Borst may be coupled to the luer connector to allow a guidewire to be advanced through the guidewire catheter shaft while maintaining hemostasis. Screws 1120 keep the handle housing coupled together. FIG. 11B illustrates a sideview of the delivery system 1100.

Figure 11C:
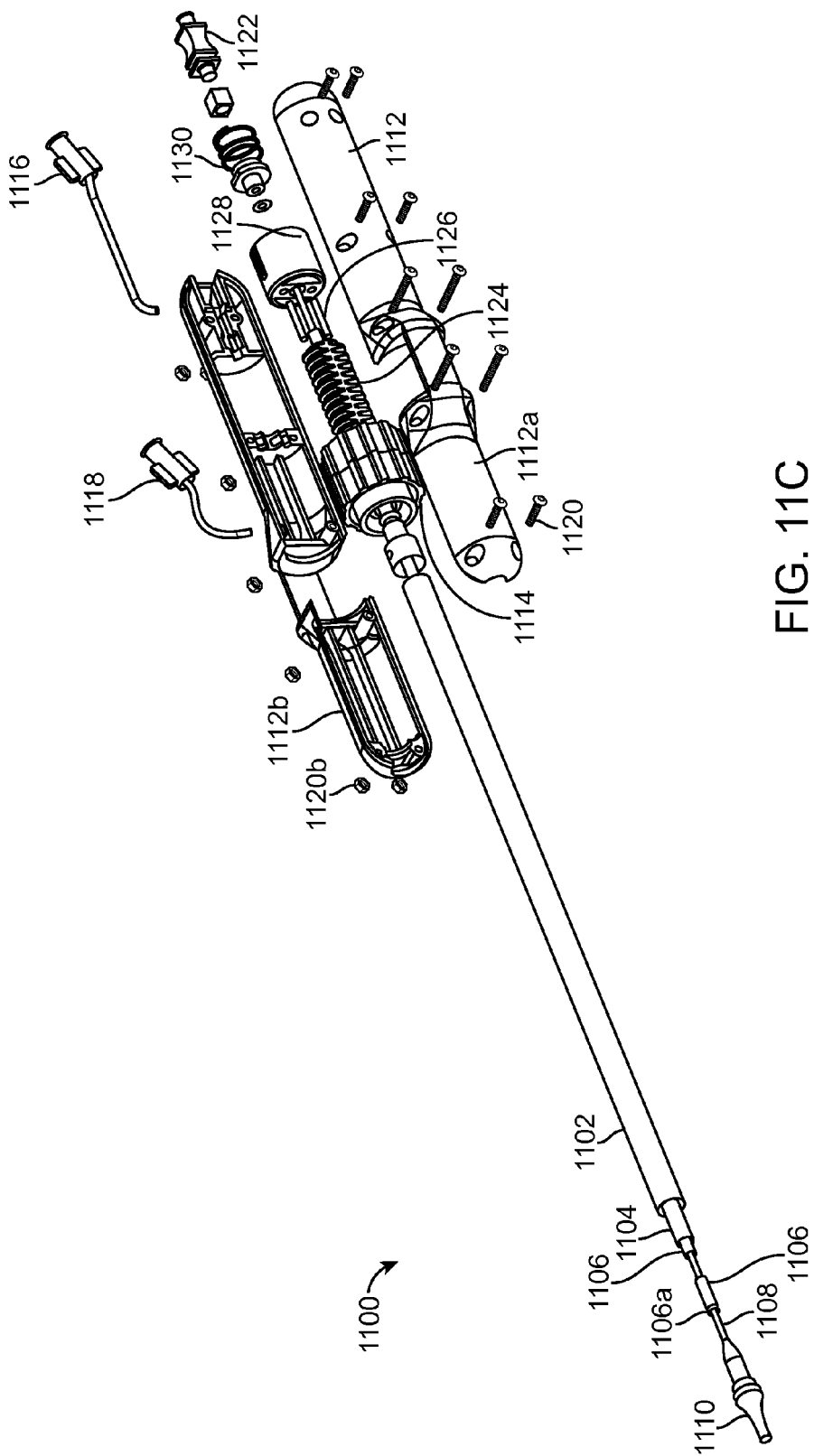

FIG. 11C is a partial exploded view of the delivery system 1100 and more clearly illustrates the components in the handle 1112 and how they interact. The handle 1112 includes a housing having two halves 1112a, 1112b which hold all the components. The handle is preferably held together with screws 1120 and nuts 1120b, although it may also be sealed using other techniques such as a press fit, snap fit, adhesive bonding, ultrasonic welding, etc. Rotation of actuator wheel 1114 is translated into linear motion of threaded insert 1124. The outer sheath catheter shaft 1102 is coupled to the threaded insert 1124, therefore rotation of actuator wheel 1114 in one direction will advance the sheath catheter shaft 1102, and rotation in the opposite direction will retract the sheath catheter shaft 1102. Further rotation of actuator wheel 1114 retracts threaded insert 1124 enough to bump into pins 1126 which are coupled to insert 1128, thereby also moving insert 1128. The bell catheter shaft 1106 is coupled to insert 1128, therefore further rotation of the actuator wheel 1114 will move the outer shaft 1102 and also move the bell catheter shaft 1106. Rotation of the actuator wheel in the opposite direction advances the sheath and threaded insert 1124 disengages from pins 1126. Spring 1130 returns insert 1128 to its unbiased position, thereby returning the bell catheter shaft to its unbiased position.

Any of the prosthetic cardiac valves disclosed herein may be carried by delivery system 1100. The atrial skirt, annuar skirt, anterior tabs, posterior tab and ventricular skirt are loaded over the bell catheter shaft and disposed under the outer sheath catheter shaft 1102. The ventricular skirt is loaded proximally so that it is closest to the handle 1112 and the atrial skirt is loaded most distally so it is closest to the tip 1110. Therefore, retraction of outer sheath catheter shaft 1102 plays a significant part in controlling deployment of the prosthetic cardiac valve. The atrial skirt therefore expands first when the outer sheath catheter is retracted. The prosthetic valve commissures may be coupled with a hub 1106a on the distal portion of hub catheter 1106 and then the bell catheter shaft is disposed thereover, thereby releasably engaging the commissures with the delivery catheter. Once other portions of the prosthetic cardiac valve have expanded, the commissures may be released.

FIG. 11D highlights the distal portion of the delivery system 1100. Outer sheath catheter shaft 1102 advances and retracts relative to bell catheter shaft 1104 which is slidably disposed in the outer sheath catheter shaft 1102. Hub catheter shaft 1106 is shown slidably disposed in bell catheter shaft 1104 and with bell catheter shaft 1104 retracted so as to expose the hub 1106a having slots 1106b that hold the prosthetic valve commissures. Inner guidewire catheter shaft 1108 is the innermost shaft and has a tapered conical section 1130 which provides a smooth transition for the prosthetic valve and prevents unwanted bending or buckling of the prosthetic cardiac valve frame. Tissue penetrating tip 1110 is adapted to penetrate tissue, especially in a cardiac transapical procedure.

Loading Fixture. The prosthetic valve may be loaded manually by a physician onto the delivery system, but this can be challenging since the valve must be properly oriented relative to the delivery system and then the commissure posts must also be engaged with the slots or receptacles on the delivery system, and captured therein. This may require multiple operators to simultaneously manipulate the prosthesis as well as the delivery system and its actuator mechanisms. Therefore, it would be advantageous to provide a fixture to facilitate loading of the prosthetic valve onto the delivery system. FIGS. 14-18B illustrate an exemplary embodiment of a loading fixture (also referred to herein as a loading device) that may be used to couple a prosthesis such as a prosthetic valve with a delivery system. The prosthesis may be any prosthesis including the prosthetic valve described in this disclosure. Similarly, the delivery system may be any delivery system, including those described herein.

Figure 14:
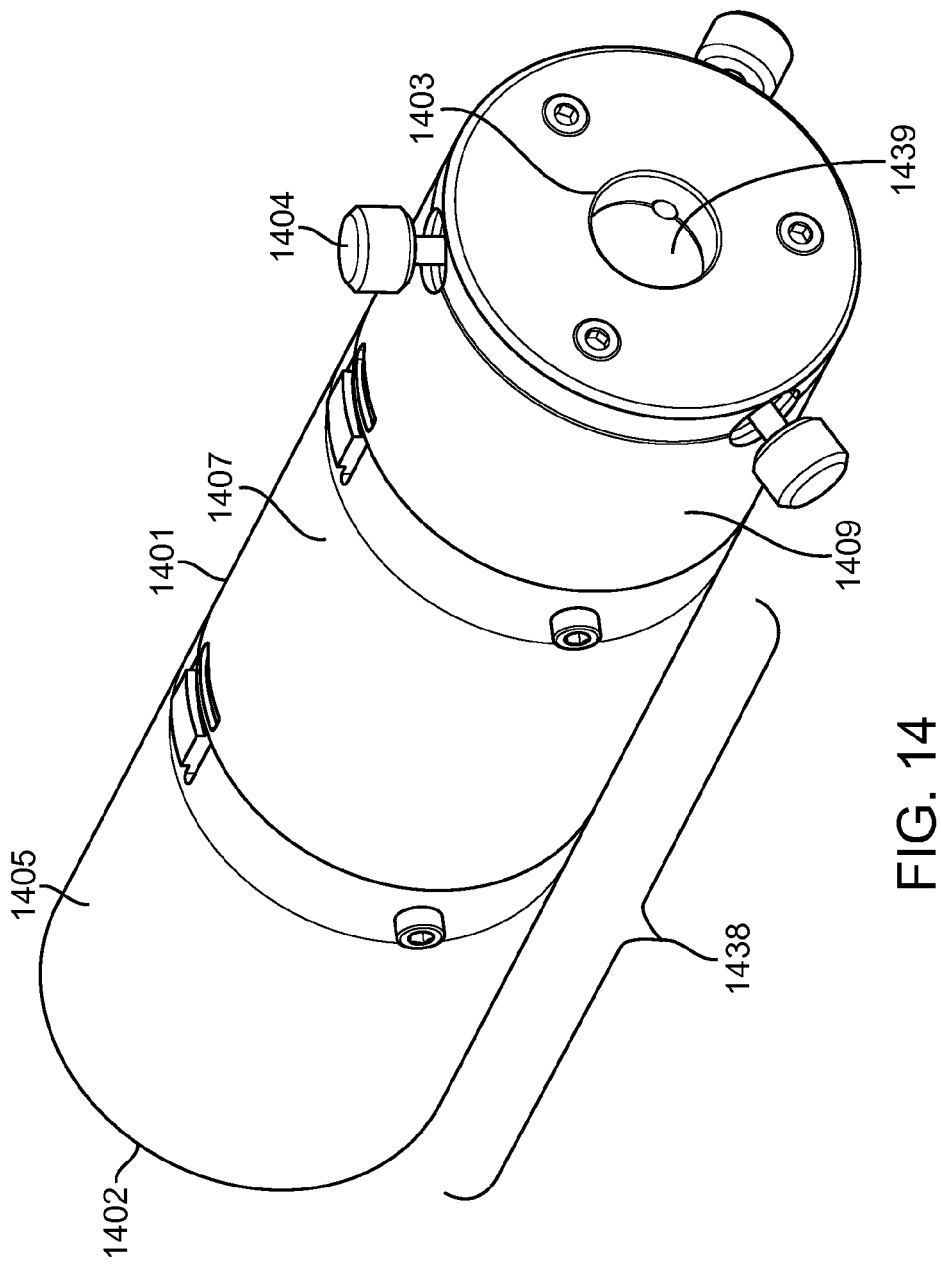
FIG. 14 is a perspective view of an exemplary loading system for the loading of a prosthetic valve with commissures into a delivery system.

FIG. 14 illustrates the loading device 1401 having a body 1438 which includes three interlocking stages or housings including a first housing 1405 (also referred to herein as the A stage or A housing), second housing 1407 (also referred to herein as the B stage or B housing), and third housing 1409 (also referred to herein as the C stage or C housing). The loading device 1401 allows a prosthesis such as a prosthetic valve to be inserted into one end of the loading device and as the prosthesis is passed therethrough, its overall diameter is reduced and selected regions of the prosthesis are further compressed radially inward when the loading device is actuated. This allows engagement of the prosthesis with the delivery system prior to delivery.

An internal channel 1439 begins at the first housing 1405 with an inlet orifice 1402 and terminates at the third housing 1409 at an outlet orifice 1403. Three hand operated and spring loaded actuators 1404 are located in the third housing 1409 and are used to depress certain portions of a prosthesis such as a prosthetic heart valve in order to load the valve onto a delivery system, the details of which are described in greater detail below.

Figure 15:
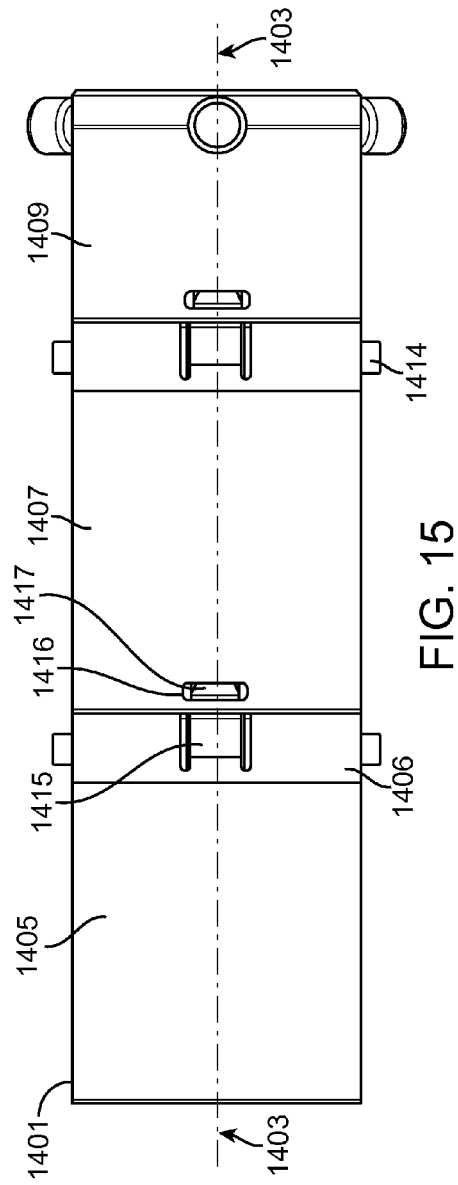
FIG. 15 is a side view of the loading system in FIG. 14.

As can be seen in FIG. 15, A stage 1405 includes a fitment ring 1406 which provides a number of cantilevered tabs 1415 that are used to mate with a locking window 1416 of the subsequent stage by virtue of a snap fit 1417. Each fitment ring 1406 is fastened to a respective stage with threaded fasteners 1414. By depressing the cantilevered tabs 1415, the snap fit 1417 is released from the locking window 1416 and the respective stages (1405, 1407, or 1409) may be separated so that each stage of the device can be manipulated individually.

Figure 16:
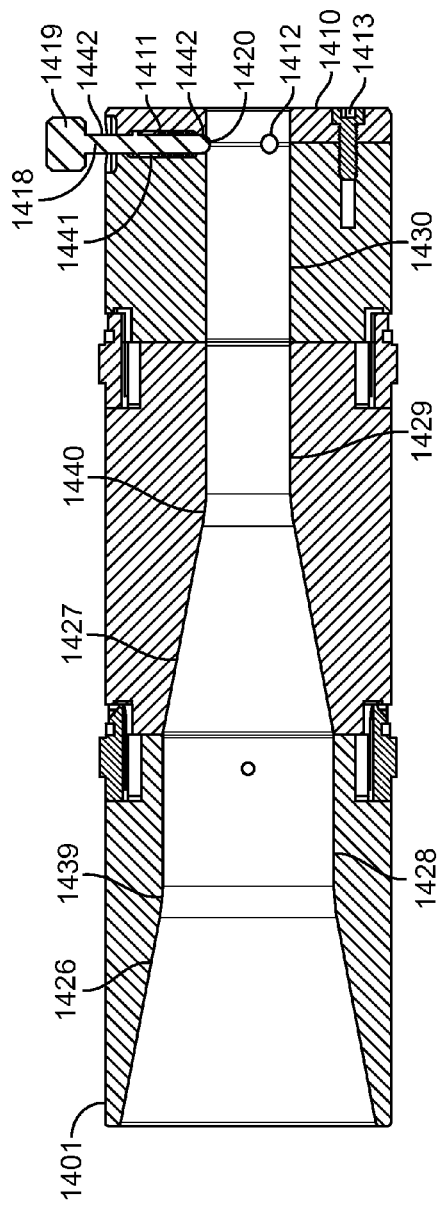
FIG. 16 cross-sectional view of the loading system in FIG. 14.

FIG. 16 shows a cross-sectional view of the loading system 1401 shown in FIG. 15. In order to begin compression of a prosthetic heart valve, the A stage 1405 first has an internally tapered section 1426 which by way of a filleted transition zone 1439 is coupled with a flat section 1428 of constant diameter. Passing through the A stage 1405 has the effect of reducing a prosthetic heart valve diameter from a first larger input value to a second smaller output value, and also helps to shape-set the frame or scaffold portion of the valve into having a circular cross section. The B stage 1407 first has an internally tapered section 1427 which by way of a filleted transition zone 1440 is coupled with a flat section 1429 of constant diameter. Passing through the B stage 1407 has the effect of again reducing a prosthetic heart valve diameter from a first larger input value (the output diameter of the A stage 1405) to a second smaller and final output value.

The internal mechanical components of the loading system 1401 are displayed in cross-sectional view in FIG. 15. As a valve is pushed from the B stage 1407 to the C stage 1409, it retains the output diameter that was set in the B stage 1407. In order to deflect certain portions of the heart valve such as commissures, anchors or otherwise necessary locating features, spring loaded actuators 1404 must be depressed, the act of which transfers linear displacement to the locating features of the prosthetic valve. Spring loaded actuators 1404 may be arranged in variably different circumferential configurations, for example three of such actuators 1404 could be equally spaced by 120° in order to deflect three separate locating features of a heart valve prosthesis. Let this design by no means be limited to three of such actuators, or any specific positioning scheme, as the design can be modified to incorporate any reasonable number and position of such actuators operating on specific portions of stents. By travelling through a constant diameter channel 1430 in the C stage 1409, a prosthetic heart valve can be brought into contact with the tips 1420 of the spring loaded actuators 1404. The spring loaded actuator 1404 is comprised of a button 1419 which can be depressed, a shaft 1418 on which a spring 1411 is housed, a shoulder 1421 against which the spring 1411 abuts to provide return force, a cylindrical pocket 1441 in which the spring 1411 has room to compress, and bearing surfaces 1442 which allow the shaft 1418 to translate freely between an uncompressed and a compressed state, and a tip 1420 that protrudes out of a hole 1412 and comes into contact with a heart valve to permit compression. As seen in FIG. 16, a capping plate 1410 is fastened to the C stage 1409 by threaded fasteners 1413. The capping plate 1410 acts with the C stage 1409 to house the springs 1411 and spring loaded actuators 1404.

Figure 17:
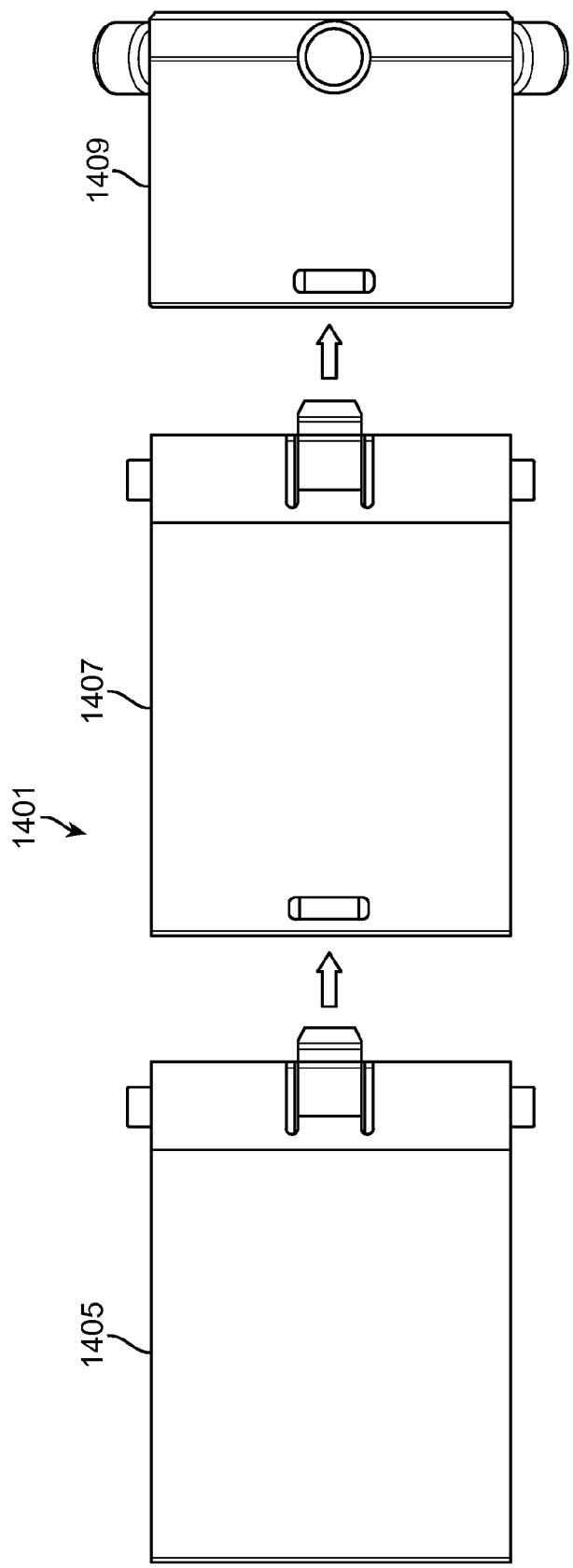
FIG. 17 is a partially exploded side view of the loading system in FIG. 14.

FIG. 17 illustrates the manner through which the A stage 1405, the B stage 1407 and the C stage 1409 are combined, and details the locations of relevant attachment mechanisms as discussed previously.

Figure 18B:
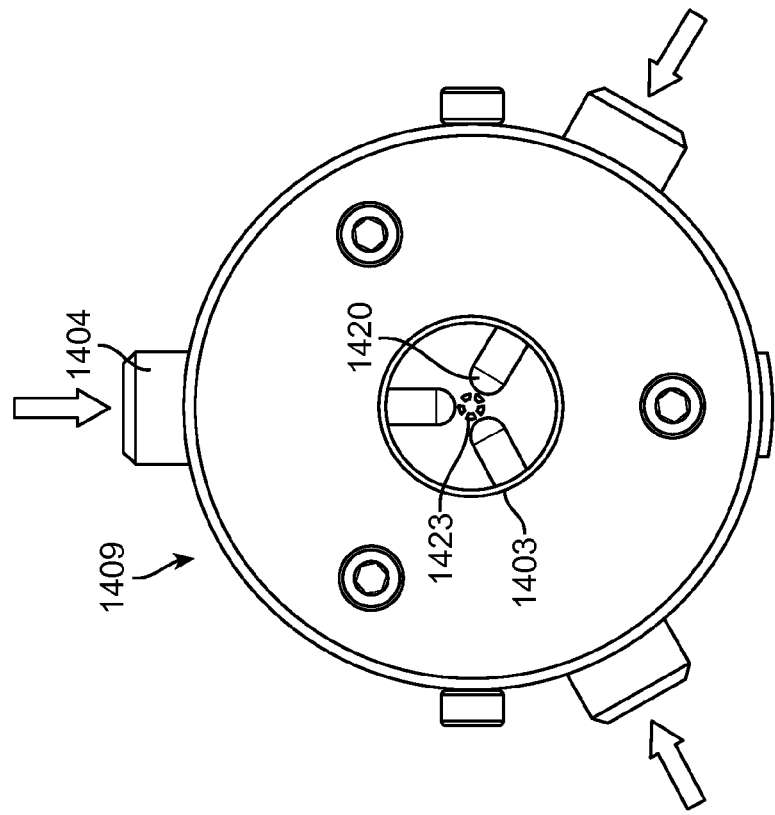
FIG. 18B is and end view of the loading system in FIG. 14 in an actuated configuration.
Figure 18A:
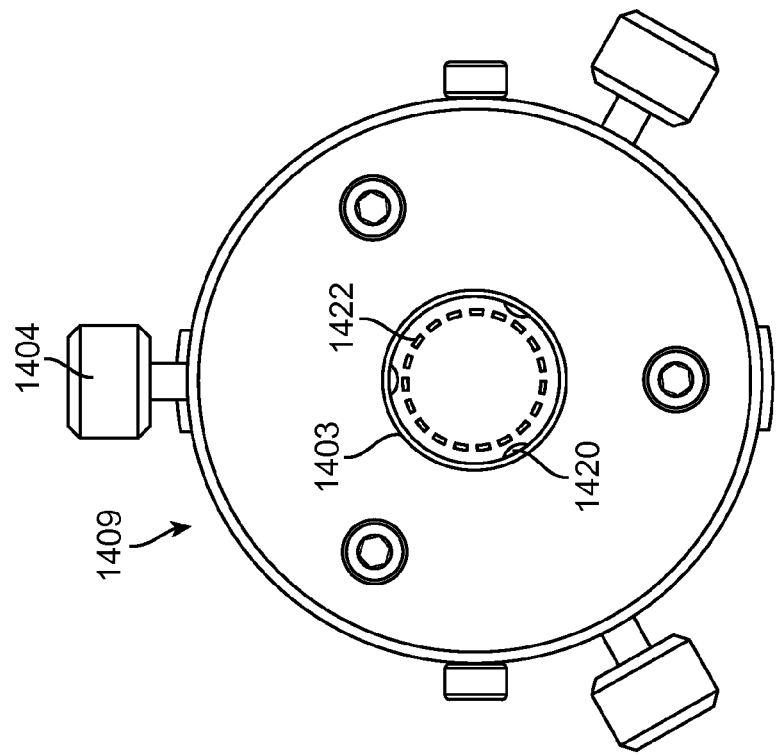
FIG. 18A is an end view of the loading system in FIG. 14 in an unactuated configuration.

As seen in FIG. 18A, the end view of the C stage 1409 has an outlet orifice 1403. An uncompressed diametral circle 1422, representing the initial large diameter at which the tips 1420 of the spring loaded actuators 1404 are normally located is also illustrated. It is then shown in FIG. 18B that upon actuation, the tips 1420 of the spring loaded actuators 1404 translate and conform to a smaller, compressed diametral circle 1423. This is the mechanism through which selective prosthetic valve deflection is achieved in order to mate portions of the prosthetic valve with the delivery system.

One of skill in the art will appreciate that the loading device is not limited to three separate housings. Alternative embodiments of the device may include a single housing that incorporates some or all of the features of the three individual housings. Single housing embodiments are illustrated in FIGS. 27-33 and described below. An exemplary embodiment of a single housing loading device is described in greater detail below. Other alternative embodiments may include either the A or B housing and the C housing, and this configuration may be as two couplable housings, or a single integrated housing. In still other embodiments, the entire diameter reduction may be accomplished with a single tapered channel in a single housing and the selective deflection may be in that same housing or in a separate housing. One of skill in the art will appreciate that any combination or permutation of the three housings and their corresponding features may be used in a loading device to load a prosthesis onto a delivery system.

Figure 19:
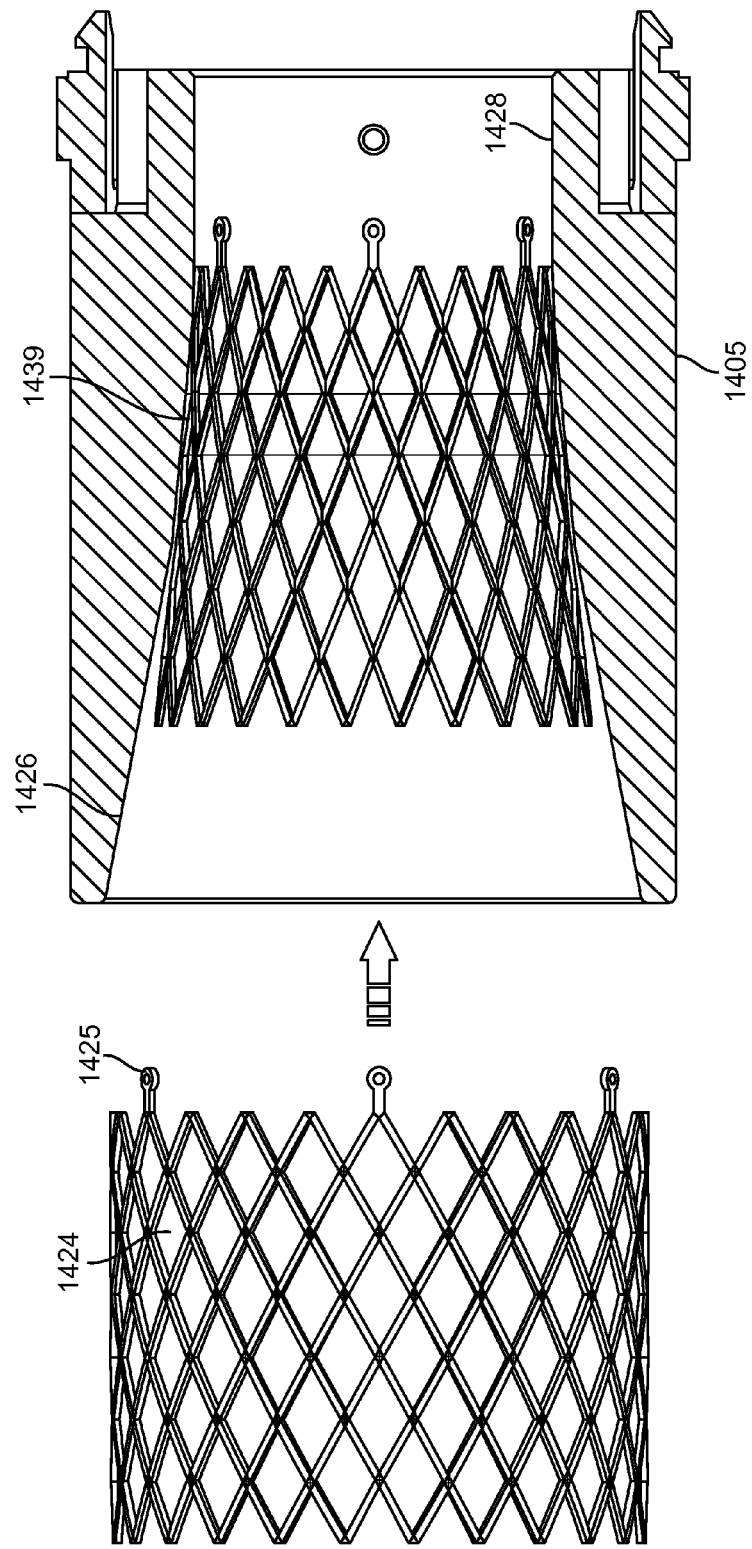
FIG. 19 is a partial cross-sectional view of a prosthesis with commissures being inserted into the first stage of the loading system of FIG. 14.

FIGS. 19-26B illustrate an exemplary method of using the loading device described above for loading a prosthetic valve such as those described herein onto a delivery system such as those described herein. FIG. 19 illustrates the initial interaction between the A stage 1405 and a generic prosthetic heart valve 1424. In this example, the generic heart valve 1424 includes three anchoring tabs 1425 which are required for location and attachment of this valve model to a delivery system. These three anchoring tabs 1425 may be equivalent to the commissure posts or struts previously described above with respect to the disclosed prosthetic mitral valve. As the generic prosthetic heart valve 1424 is manually pushed through the A stage 1405, the valve slides down an internally tapered section 1426, past a filleted transition zone 1439, and into a flat section 1428 of constant diameter. In order to safely reduce the diameter of a heart valve prosthesis that is at least partially manufactured from alloys such as Nitinol it is first necessary to cool the prosthesis in chilled saline, in order to bring the device below a temperature known as the austenitic finish temperature, which is specific to each alloy and dependant upon manufacturing processes. This is the temperature at which the crystalline structure of Nitinol becomes arranged in a manner that allows for plastic deformation, with little risk of permanent damage due to strain. When the generic prosthetic heart valve 1424 is positioned in the flat section 1428 and manually adjusted to acquire a circular shape, the A stage 1405 is ready to be attached to the B stage 1407, and this step of the procedure will be detailed below.

Figure 20:
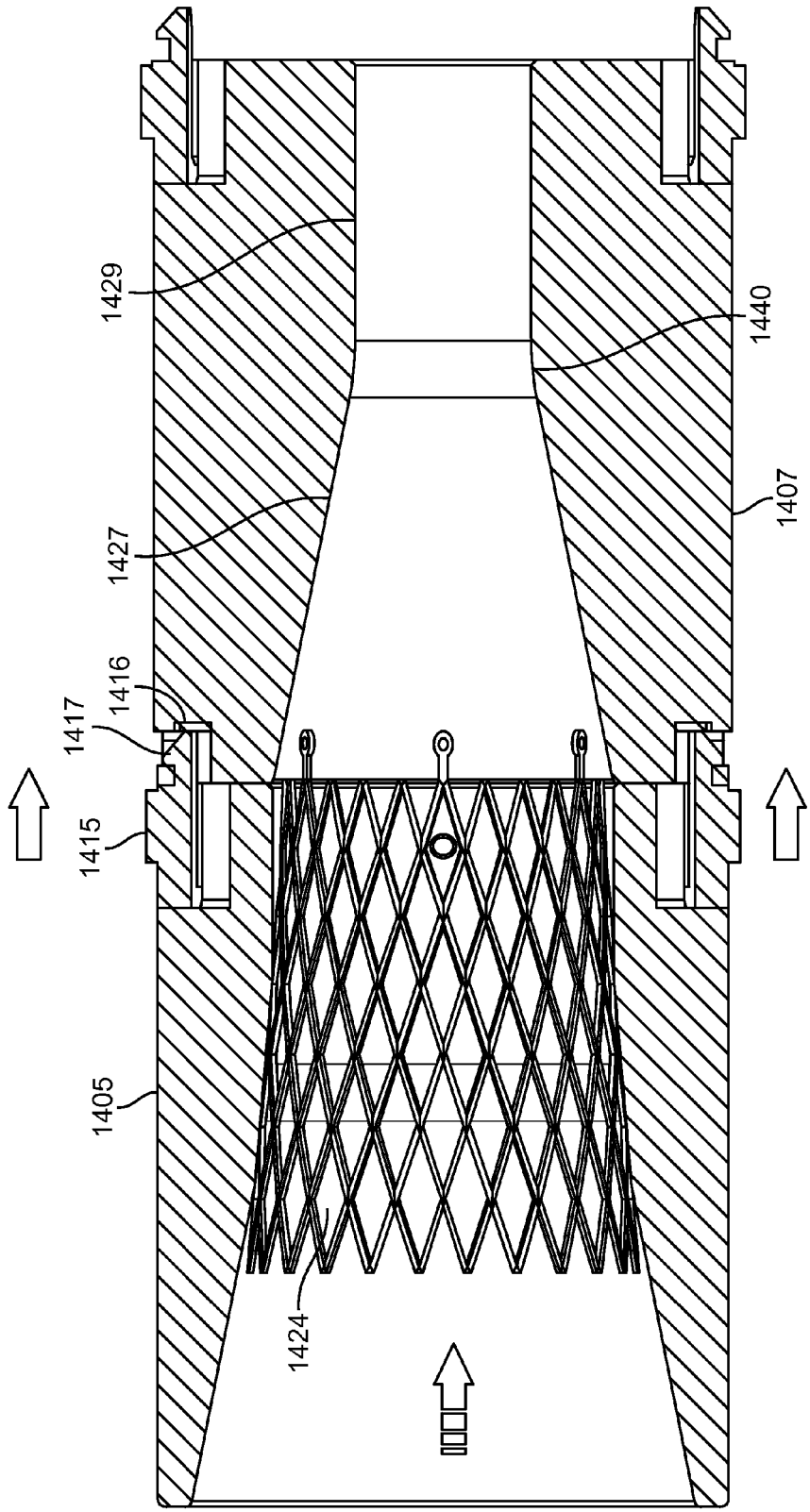
FIG. 20 is a partial cross-sectional view the prosthesis in FIG. 19 travelling from the first to the second stage of the loading system of FIG. 14.
Figure 21:
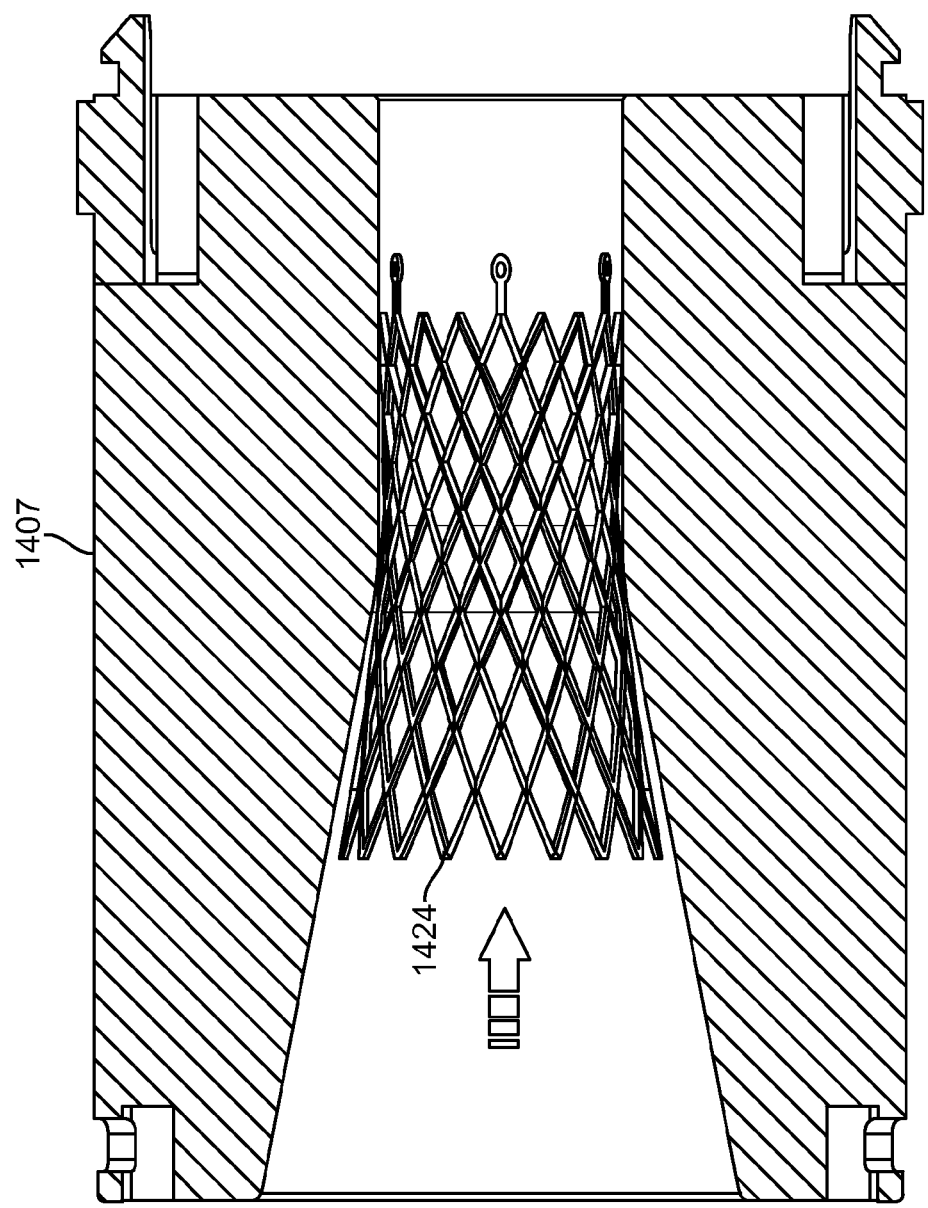
FIG. 21 is a partial cross-sectional view of the prosthesis in FIG. 19 travelling through the second stage of the loading system of FIG. 14.

As shown in FIG. 20, the A stage 1045 is latched onto the B stage 1407 by way of pressing cantilevered tabs 1415 on the A stage 1405 that end in snap fits 1417 into respective locking windows 1416 that reside on the B stage 1407. After latching the A stage 1405 onto the B stage 1407, the generic prosthetic heart valve 1424 can be advanced across the junction and into an internally tapered section 1427, past a filleted transition zone 1440 and finally into a flat section 1429 of constant and final diameter. This step of the procedure can be more readily appreciated if viewed in FIG. 21, as it becomes necessary to detach the A stage 1405 from the B stage 1407 as the generic prosthetic heart valve 1424 assumes its end location in the B stage 1407.

Figure 22:
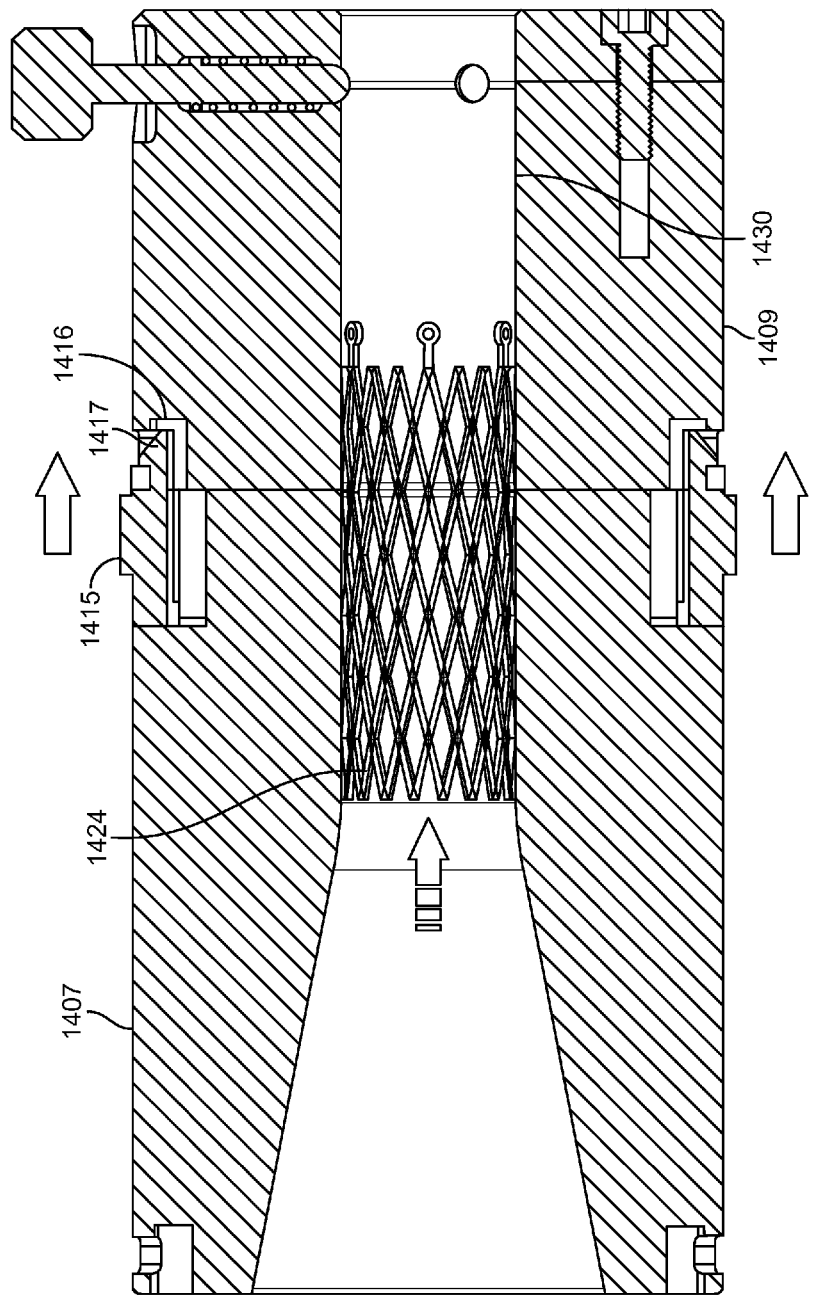
FIG. 22 is a partial cross-sectional view of the prosthesis in FIG. 19 travelling from the second to the third stage of the loading system in FIG. 14.

As shown in FIG. 22, the B stage 1407 is latched onto the C stage 1409 by way of pressing cantilevered tabs 1415 on the B stage 1407 that end in snap fits 1417 into respective locking windows 1416 that reside on the C stage 1409. After latching the B stage 1407 onto the C stage 1409, the generic prosthetic heart valve 1424 can be advanced across the junction and into a flat section 1430 of constant and final diameter. The diameter of the flat section 1430 is designed to optimally compress the valve 1424 to the smallest diameter that would still allow passage of a respective delivery system or components thereof, and still allow access to the relevant stent features required for valve loading and anchoring to the delivery system.

Figure 23:
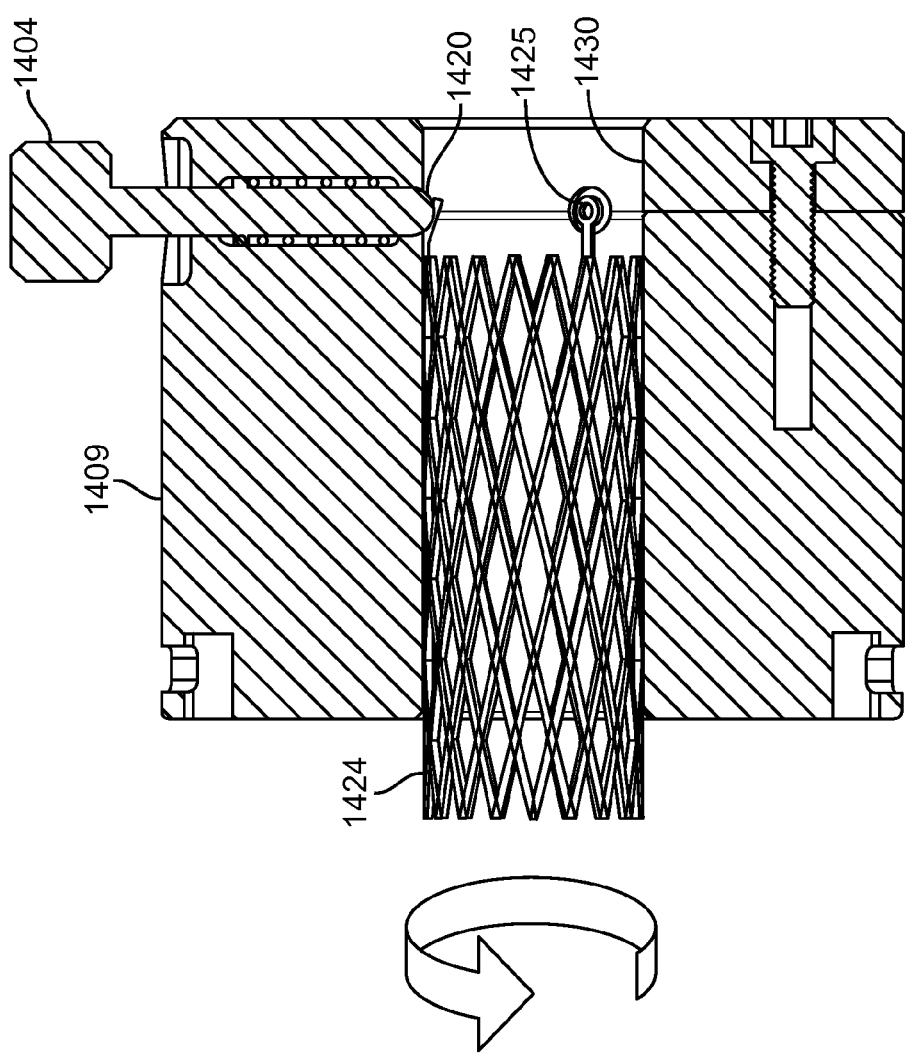
FIG. 23 is a partial cross-sectional view of the prosthesis in FIG. 19 positioned within the third stage of the loading system of FIG. 14.

The final compressed location of a generic prosthetic heart valve 1424 within the C stage 1409 can be seen in FIG. 23. Before accurate anchoring tab 1425 deflection can be performed, it may first be necessary to rotate the valve 1424 within the flat section 1430 of constant diameter so as to align all anchoring tabs 1425 with the tips 1420 of respective spring loaded actuators 1404. This practice is illustrated in FIG. 23. After performing anchoring tab 1425 alignment, accurate spring loaded actuator 1404 operation becomes possible.

Figure 24:
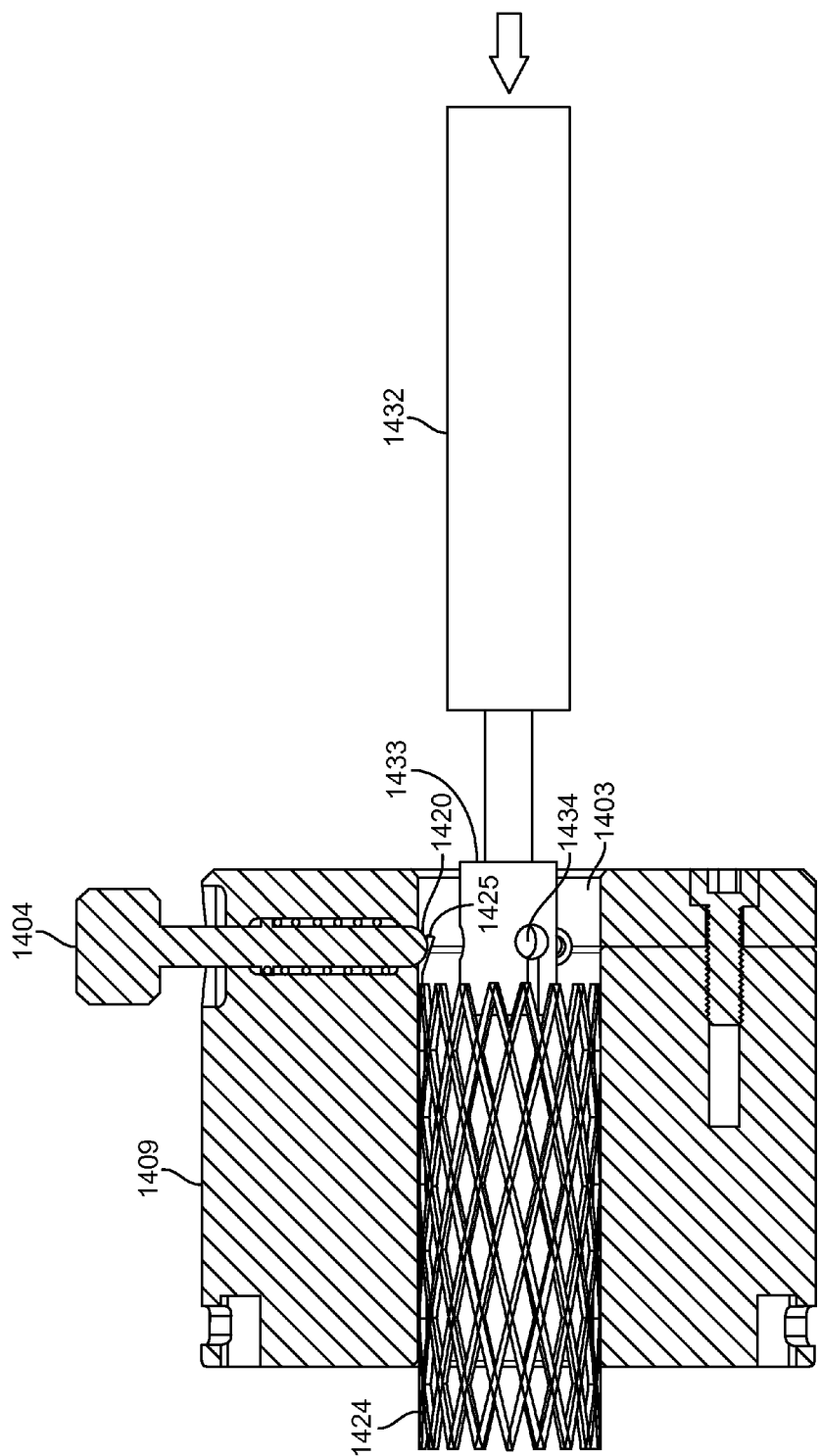
FIG. 24 is a partial cross-sectional view of the prosthesis in FIG. 19 positioned in the third stage of the loading system of FIG. 14 and with a delivery system also engaged with the loading system.

As can be seen in FIG. 24, a generic delivery system 1432 can be introduced to the outlet orifice 1403 of the C stage 1409, and retaining pockets (also referred to herein as receptacles or slots) 1434 located in an anchoring hub 1433 can be brought into alignment with the anchoring tabs 1425 of a generic prosthetic heart valve 1424.

Figure 25:
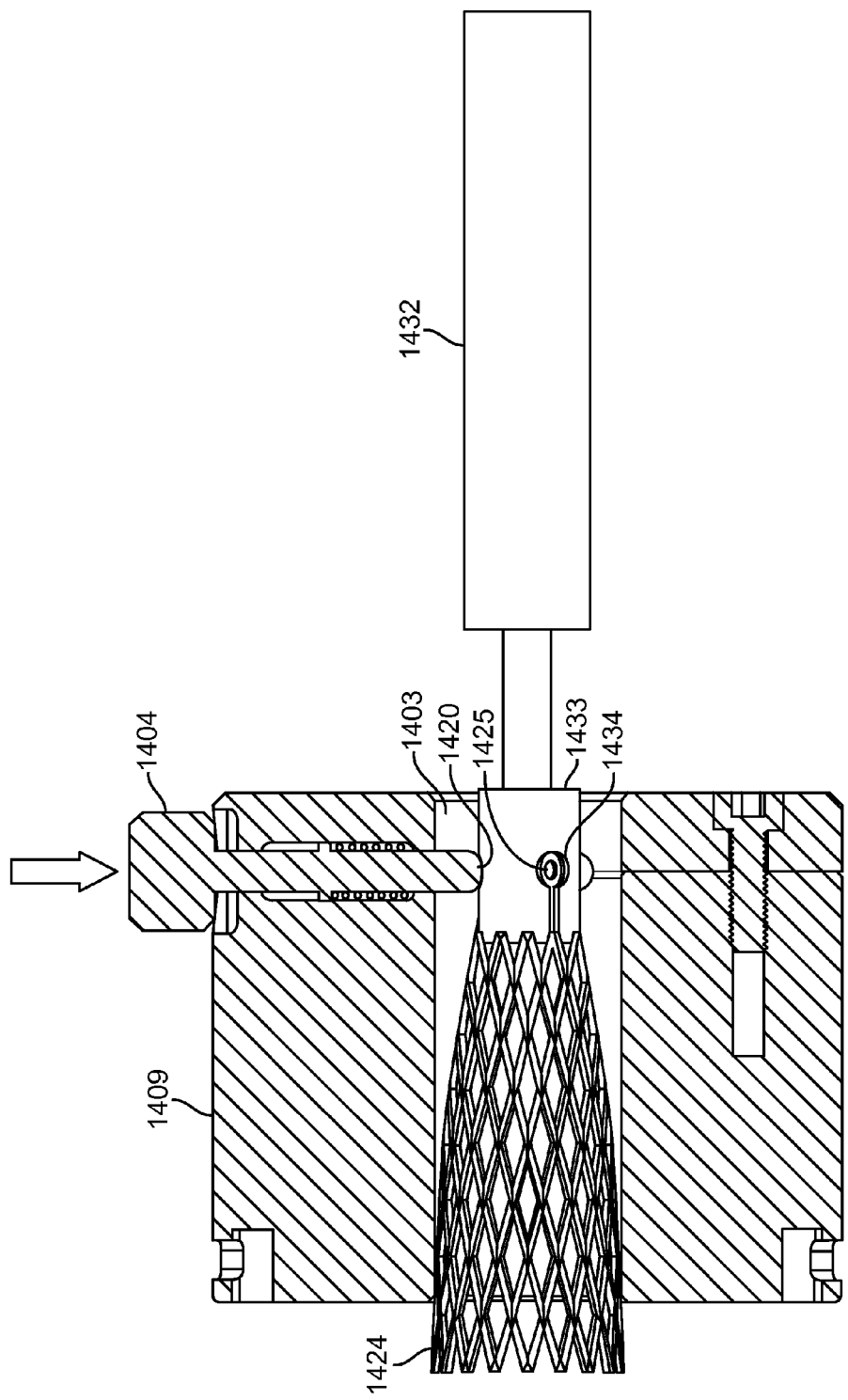
FIG. 25 is a partial cross-sectional view of the prosthesis in FIG. 19 after actuation of the loading system of FIG. 14.

FIG. 25 illustrates the mechanism by which the tips 1420 of the spring loaded actuators 1404 are pressed into the anchoring tabs 1425 of a generic prosthetic heart valve 1424, so as to deflect them by bending, and force the anchoring tabs 1425 into respective retaining pockets 1434 located in the anchoring hub 1433 of a generic delivery system 1432.

Figure 26B:
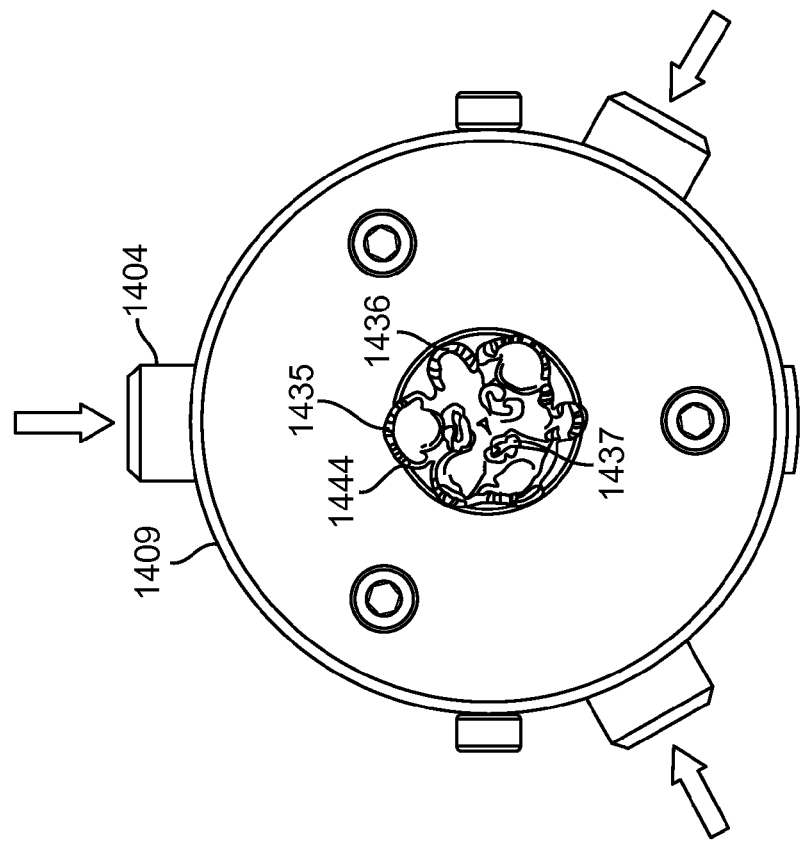
FIG. 26B is an end view of the loading system in FIG. 14 with a prosthesis in a collapsed and deflected configuration.
Figure 26A:
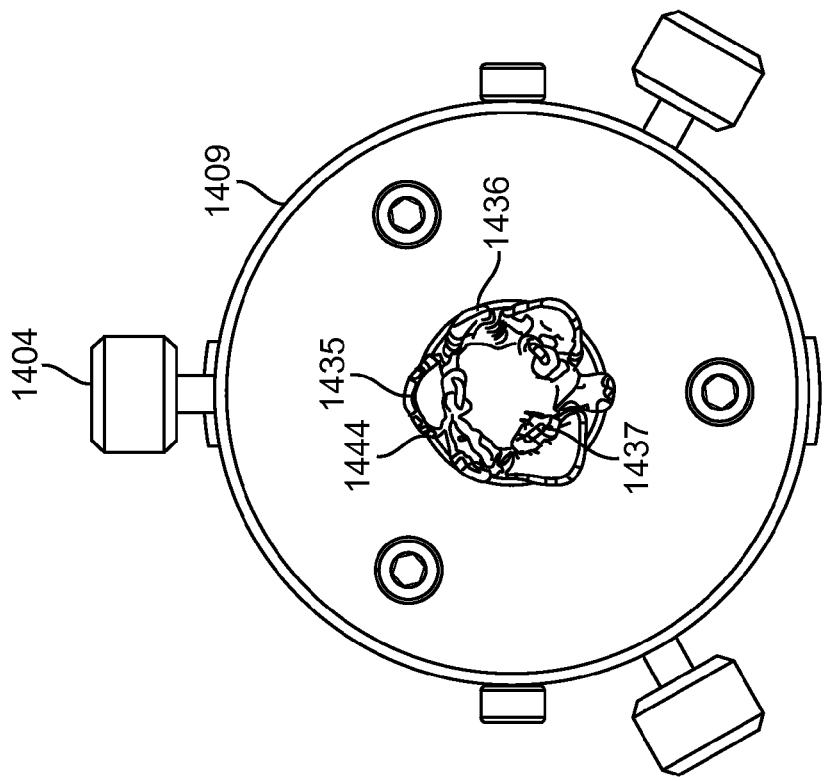
FIG. 26A is an end view of the loading system in FIG. 14 showing a prosthesis in a collapsed but undeflected configuration.

FIG. 26A shows an end view of the C stage 1409, with a prosthetic heart valve 1444 such as those previously described above, compressed and in place prior to final deflection. Relevant features of the prosthetic heart valve 1444 include the ventricular skirt 1435, trigonal tabs 1436, and commissure anchors (also referred to as commissure posts or struts) 1437, details of which can be found elsewhere in this specification.

FIG. 26B shows an end view of the C stage 1409, with a prosthetic heart valve 1444 compressed and in place after final deflection. Note that relevant features such as the ventricular skirt 1435, and trigonal tabs 1436 have not been displaced by any portion of the spring loaded actuators 1404, and that only the commissure anchors 1437 have been displaced to a final reduced diameter and made available to respective features on the respective delivery system, details of which are disclosed elsewhere in this specification. Once the commissure anchors 1437 have been deflected radially inward and positioned in the corresponding receptacles on the delivery catheter, an outer shaft or sheath may be slidably disposed thereover in order to capture the commissure anchors. Another outer shaft or sheath may then be slidably disposed over the remainder of the prosthetic valve to capture it and hold it in position during delivery. Release of the prosthetic valve is described below.

FIGS. 27-29B illustrate another exemplary embodiment of a loading system. While this embodiment is similar to the embodiment previously described, this embodiment has the advantage of providing support to both internal and external surfaces of the prosthesis during loading, and also the actuators are simultaneously actuated.

Figure 27:
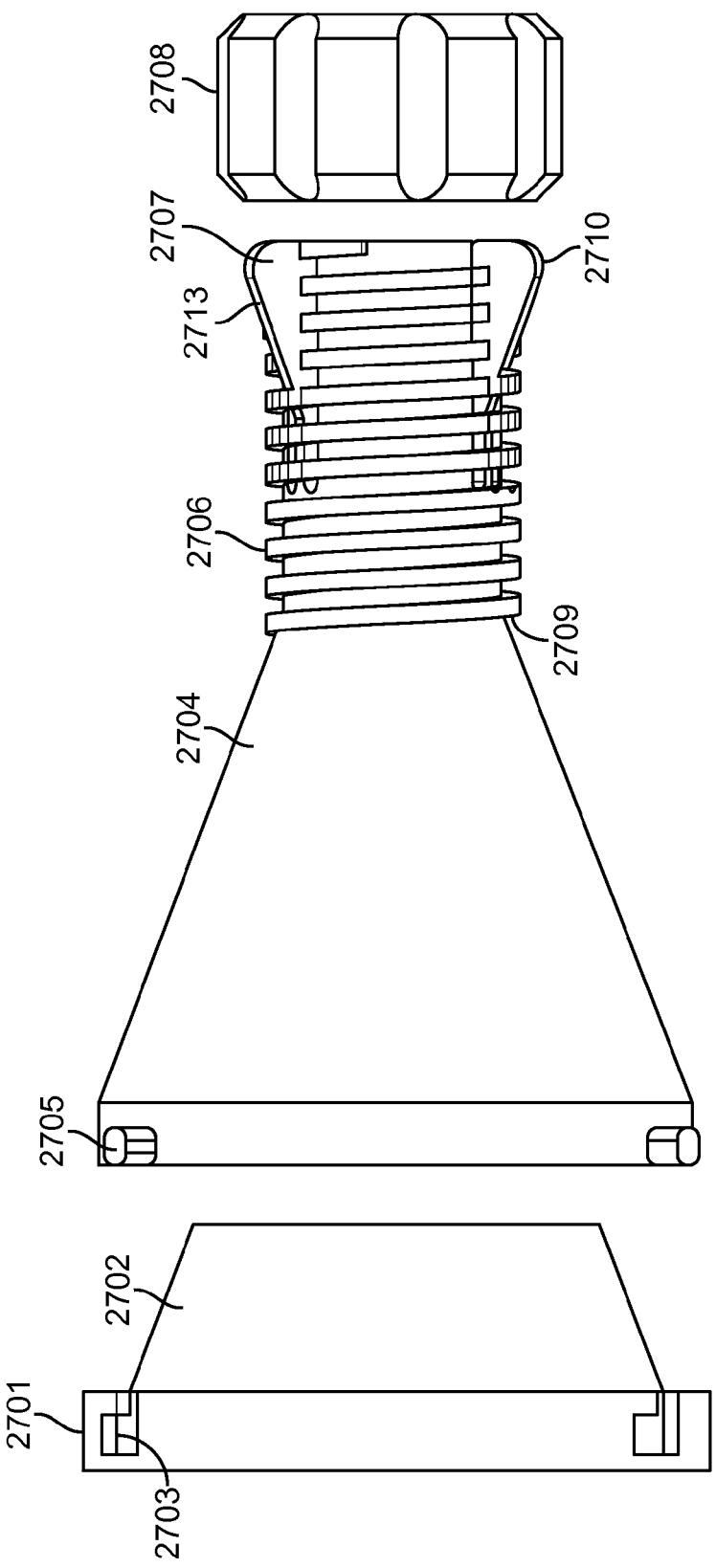
FIG. 27 illustrates another exemplary embodiment of a loading system.

As seen in FIG. 27, a variation of the valve loading system is detailed. An inner cone 2701 provides support for the internal surface of a valve or prosthesis to be loaded. The important features of inner cone 2701 include a conical inclined plane 2702, and twistable locking mechanism 2703 such as a bayonet lock. The conical inclined plane 2702 aids in seating a valve to be loaded, while the twistable locking mechanism 2703 allows the inner cone 2701 to be securely fastened to an outer cone 2704, through a twisting motion that will be further described below.

Three locking pegs 2705 on the circumference of the outer cone 2704 allow the base of the outer cone 2704 to be mated to the locking mechanism 2703 of the inner cone 2701. A threaded section 2706 of the outer cone 2704 begins at an initial end 2709 and terminates at a final end 2710, and is threaded in a manner that allows for mating to a displacement nut 2708 which has matching internal threads. As the displacement nut 2708 is screwed forward from initial end 2709 to final end 2710, the leading edge of the displacement nut 2708 forces a fin or other finger-like member 2707 to be pushed down due to the inclined plane that comprises the rib 2713 of the fin 2707, and the sliding motion of the displacement nut 2708 as it rides over the fin 2707. A plurality of fins 2707 may be spaced circumferentially about the outer cone 2708 at the final end 2710 in order to affect the desired mechanism. This embodiment preferably has three fins spaced generally 120 degrees apart.

Figure 28B:
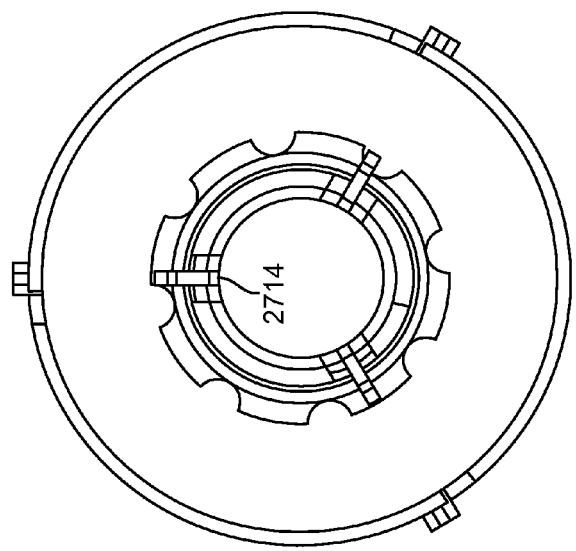
FIGS. 28A-28B illustrate the loading system of FIG. 27 prior to actuation.
Figure 28A:
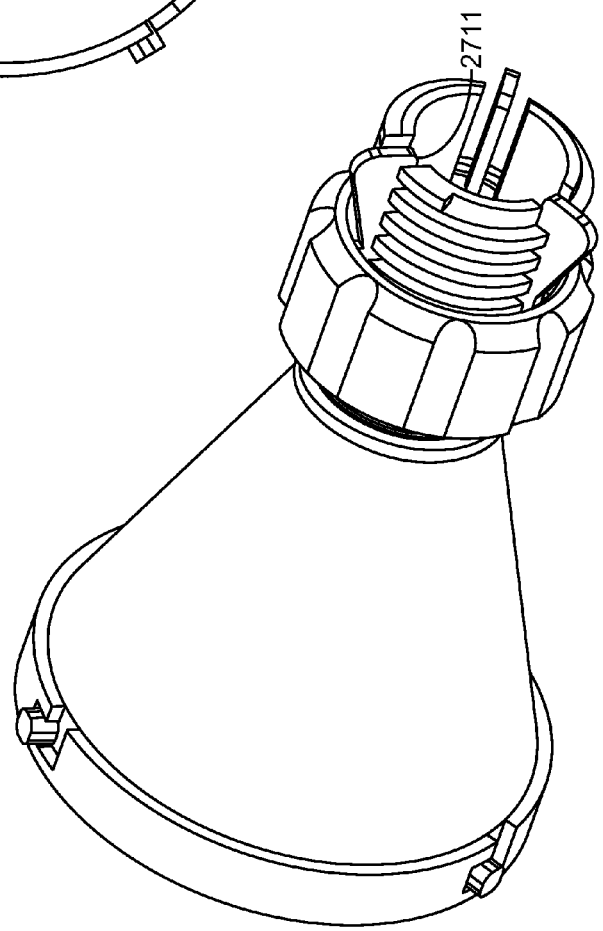

As seen in FIG. 28A and FIG. 28B, end views of the device provide further detail of the inherent mechanical relationships between relevant parts. Pad 2714 is seen in FIG. 28B resting in an un-deflected position 2711. As the displacement nut 2708 rides over the threaded section 2706, the position of pad 2714 moves radially inward to a deflected position 2712, as seen in FIG. 29A. A plurality of pads 2714 may be spaced circumferentially about the outer cone 2708 at the final end 2710 in order to affect the desired mechanism in conjunction with an equal plurality of fins 2707.

Figure 30:
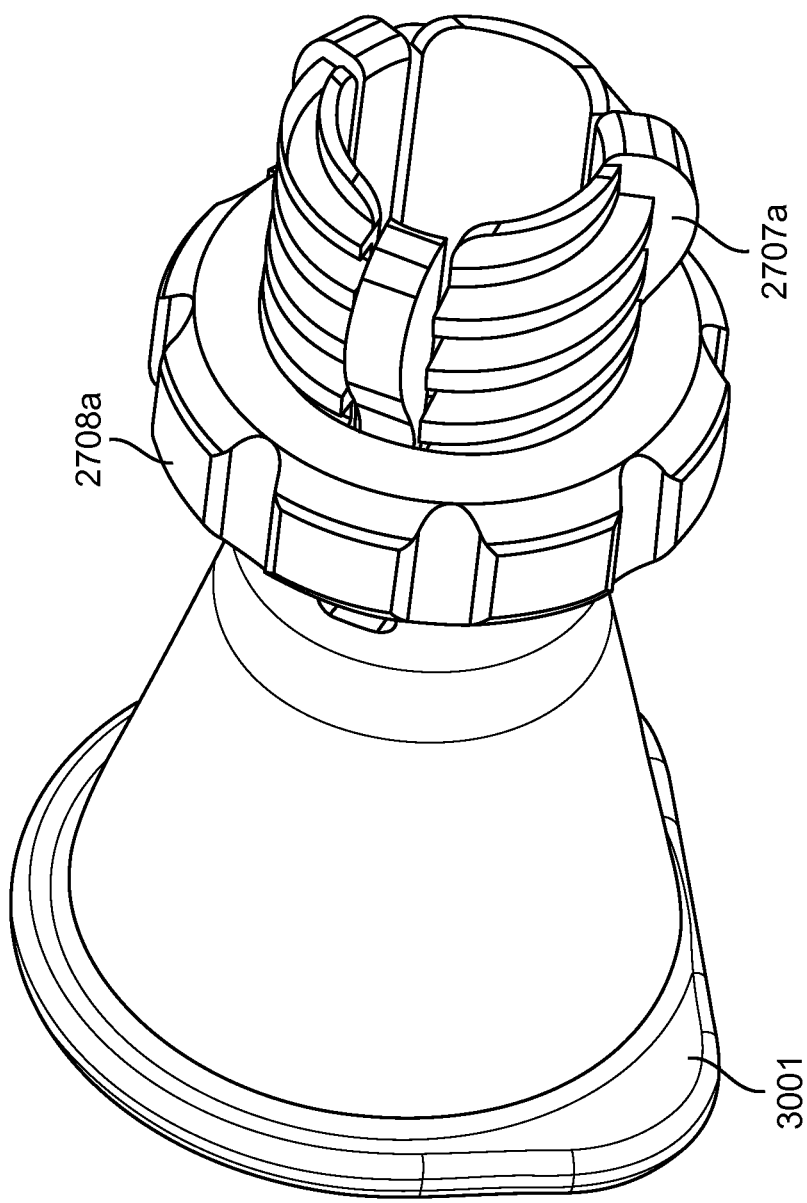
FIGS. 30-33 illustrate still another exemplary embodiment of a loading system.

FIGS. 30-33 illustrate another exemplary embodiment of a loading fixture. FIG. 30 is a perspective view of the loading system. The fingers 2707a are thicker than previous embodiments and also have a cammed profile instead of a ramped profile. Also, the displacement nut 2708a is thinner than previous embodiments. These features help the operator to smoothly actuate the displacement nut and radially collapse a portion of the prosthesis for loading onto a delivery system. Additionally, this embodiment includes a "D" shaped flange 3001 on the inlet side of the cone (this feature can also be seen in FIG. 33) which can be used for valve alignment purposes. Other alignment features will be illustrated in FIGS. 31-32.

Thus the operator will know that the flat portion of the "D" shaped flange is also the flat portion of the "D" shaped prosthesis.

Figure 31:
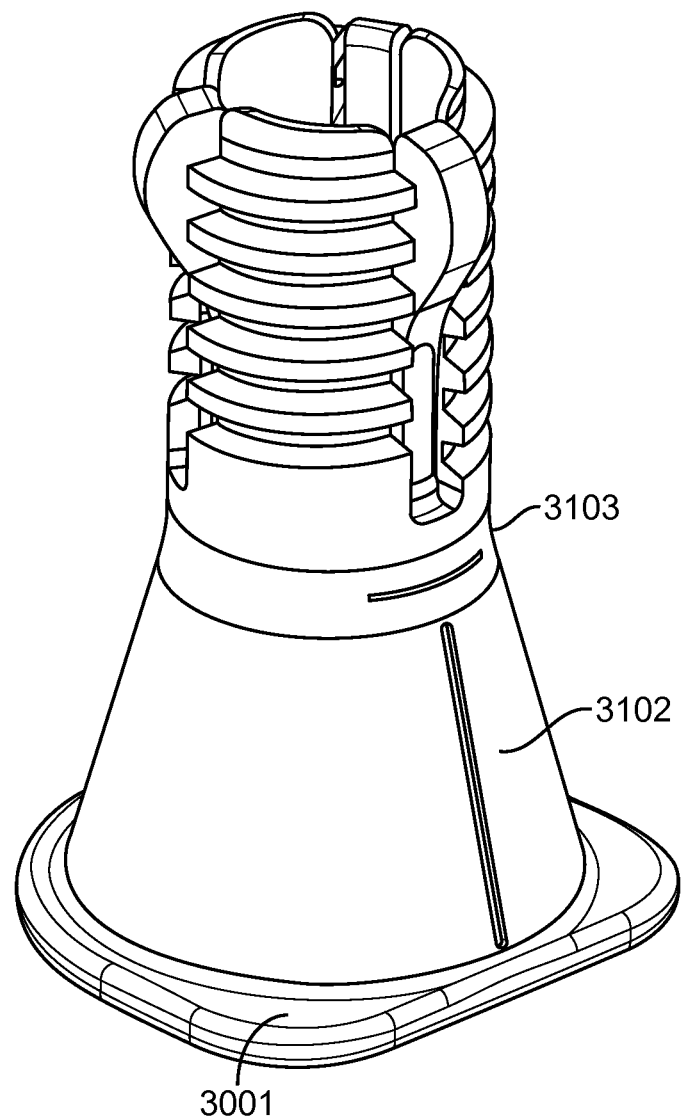

FIG. 31 is an isometric view of the loading cone with the displacement nut removed, illustrating optional features which may be used in any of the loading fixture embodiments. A vertical slot 3102 appearing on the tapered portion of the loading cone acts as a landmark for a suture (not illustrated) on the prosthetic valve to be aligned with. This allows the valve to be accurately located during loading. A horizontal slot 3103 appearing on the tapered transition portion of the loading cone acts as a landmark with which the atrial skirt region of the stent can be registered against, in order to accurately locate the valve prior to commissure capture. The loading cone may be formed of an optically clear polymer such as polycarbonate which allows the user to see valve features/landmarks throughout the loading process.

Figure 32:
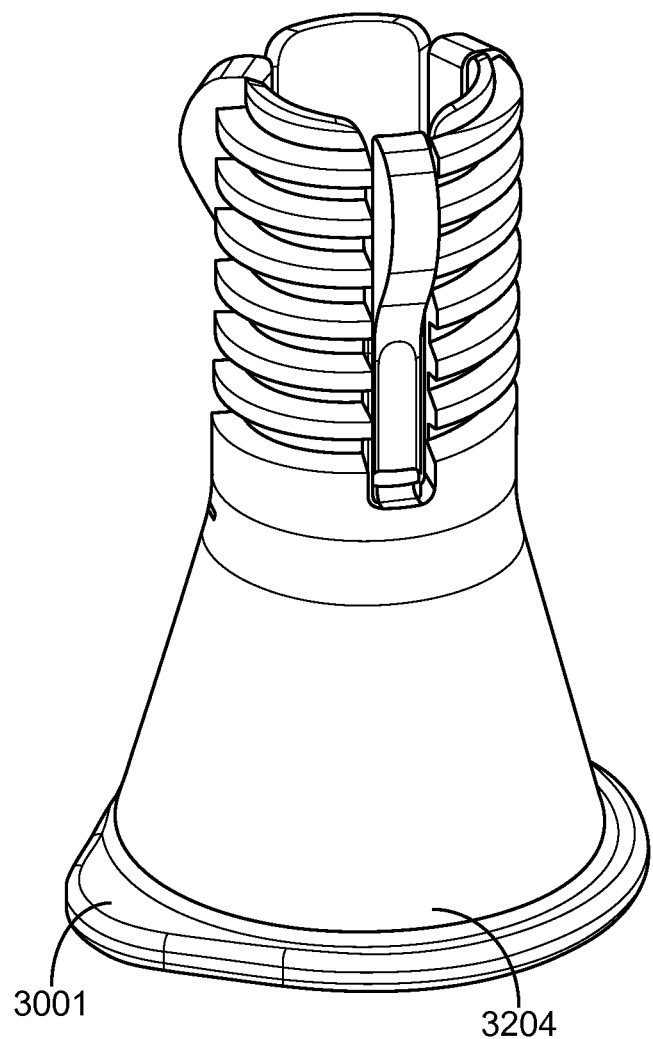

FIG. 32 is an isometric view of the loading cone. An optional size designation 3004 has been stamped on the tapered section of the cone adjacent to the D-shaped flange 3001. Indicia allow a user to easily identify and select the appropriate loading fixture.

Figure 33:
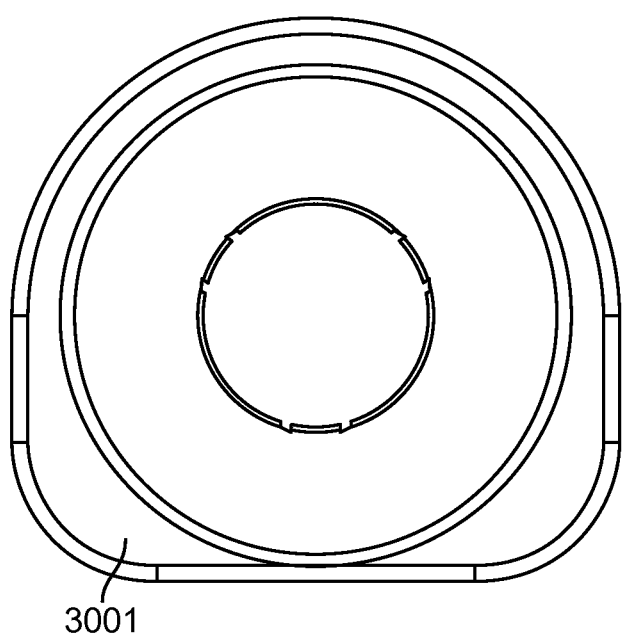

FIG. 33 is an end view of the loading cone. The D-shaped flange 3001 can clearly be seen in this view. When loading a valve into the loading cone, an operator may orient the flat side of the valve with the flat portion of the D-shaped flange prior to insertion.

The embodiment of FIGS. 30-33 provides a single stage for collapsing a prosthetic valve and therefore is easier than a multiple stage loading fixture. The prosthetic valve may be chilled in cold saline during loading as previously discussed above. Because this embodiment is smaller and has fewer parts than other embodiments, it is lighter and easier to use, and also manufacturing costs are reduced. It may be actuated with a single hand while other embodiments may require more than one hand.

Delivery Method. A number of methods may be used to deliver a prosthetic cardiac valve to the heart. Exemplary methods of delivering a prosthetic mitral valve may include a transluminal delivery route which may also be a transseptal technique which crosses the septum between the right and left sides of the heart, or in more preferred embodiments, a transapical route may be used such as illustrated in FIGS. 12A-12L. The delivery device previously described above may be used to deliver any of the embodiments of prosthetic valves described herein, or other delivery devices and other prosthetic valves may also be used, such as those disclosed in U.S. patent application Ser. No. 13/096,572, previously incorporated herein by reference. However, in this preferred exemplary embodiment, the prosthetic cardiac valve of FIG. 6 is used so that the anterior tabs deploy first, followed by the posterior tab, and then the ventricular skirt.

Figure 12A:
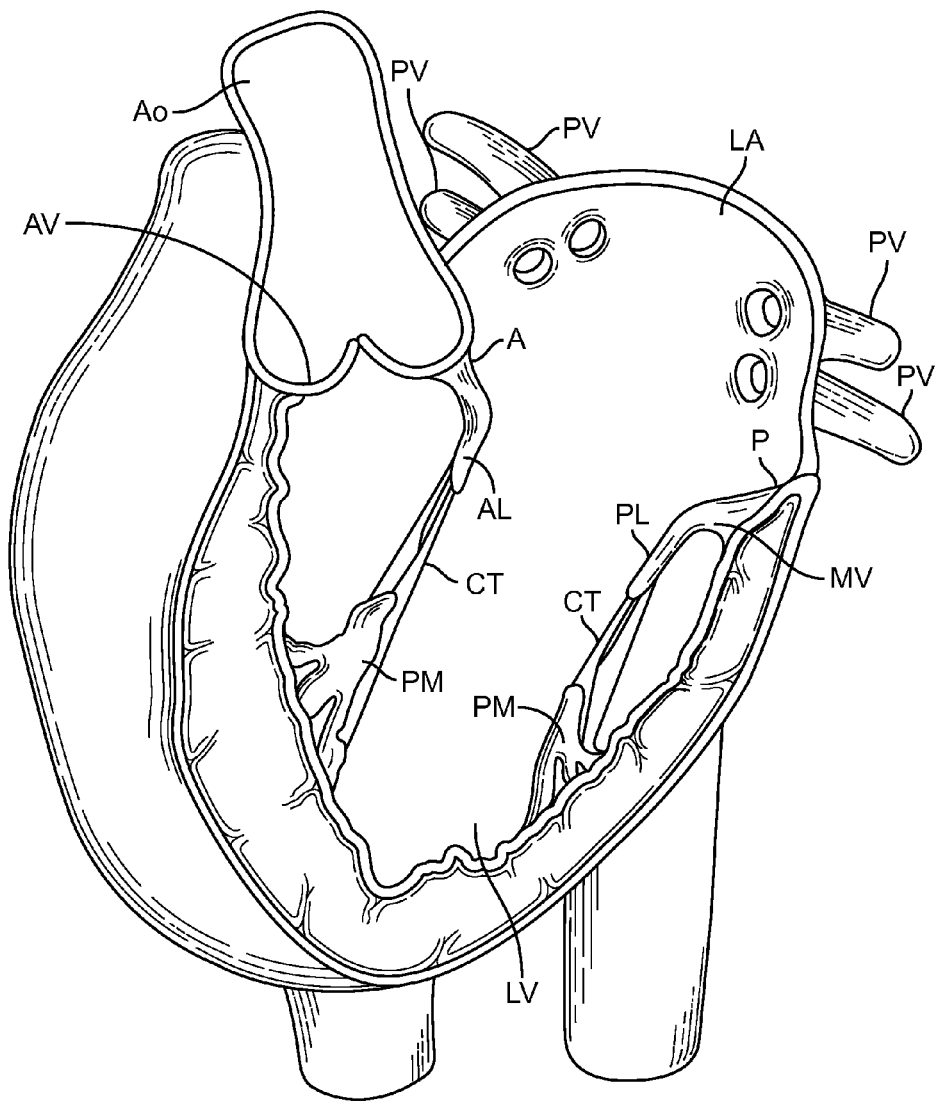
FIGS. 12A-12L illustrate an exemplary method of implanting a prosthetic cardiac valve.

FIG. 12A illustrates the basic anatomy of the left side of a patient's heart including the left artrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta Ao with the aortic valve AV preventing regurgitation.

Figure 12B:
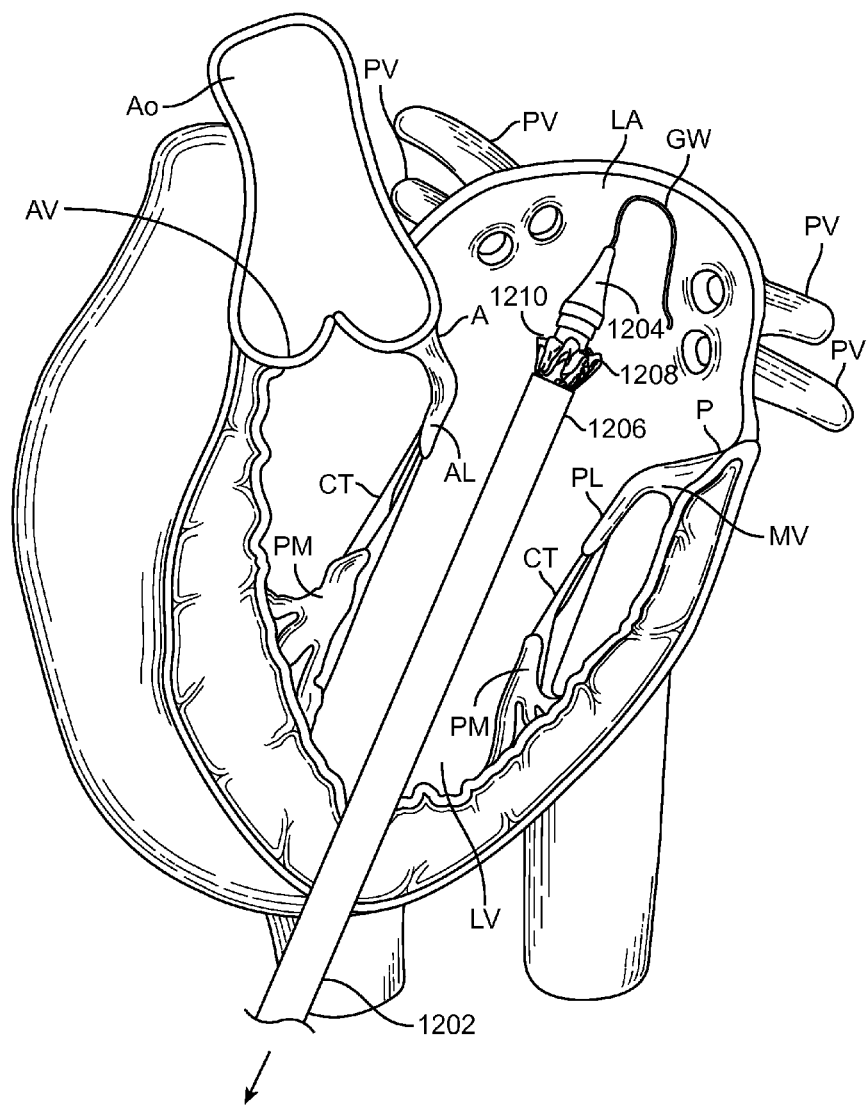
Figure 12C:
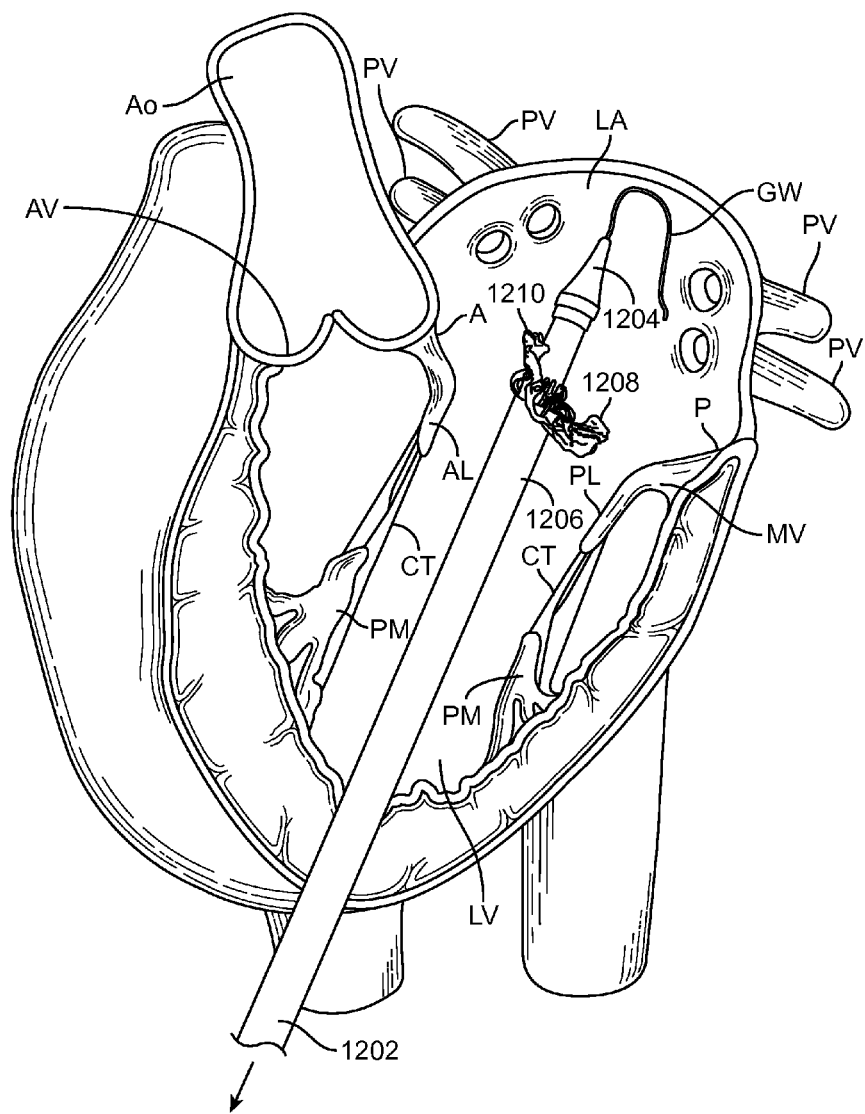
Figure 12D:
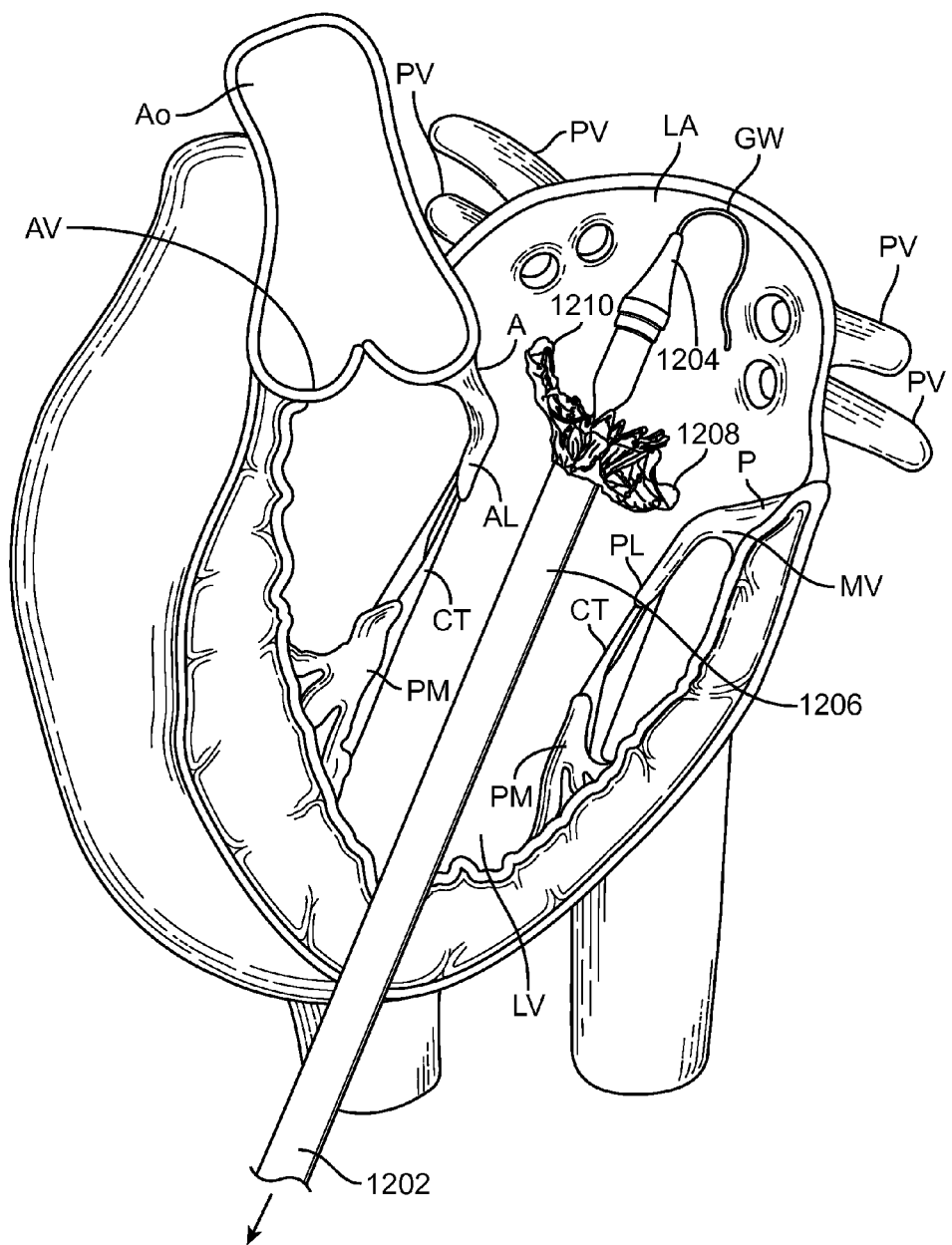

FIG. 12B illustrates transapical delivery of a delivery system 1202 through the apex of the heart into the left atrium LA. The delivery system 1202 may be advanced over a guidewire GW into the left atrium, and a tissue penetrating tip 1204 helps the delivery system pass through the apex of the heart by dilating the tissue and forming a larger channel for the remainder of the delivery system to pass through. The delivery catheter carries prosthetic cardiac valve 1208. Once the distal portion of the delivery system has been advanced into the left atrium, the outer sheath 1206 may be retracted proximally (e.g. toward the operator) thereby removing the constraint from the atrial portion of the prosthetic valve 1208. This allows the atrial skirt 1210 to self-expand radially outward. In FIG. 12C, as the outer sheath is further retracted, the atrial skirt continues to self-expand and peek out, until it fully deploys as seen in FIG. 12D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it unwanted movement downstream into the left ventricle.

Figure 12E:
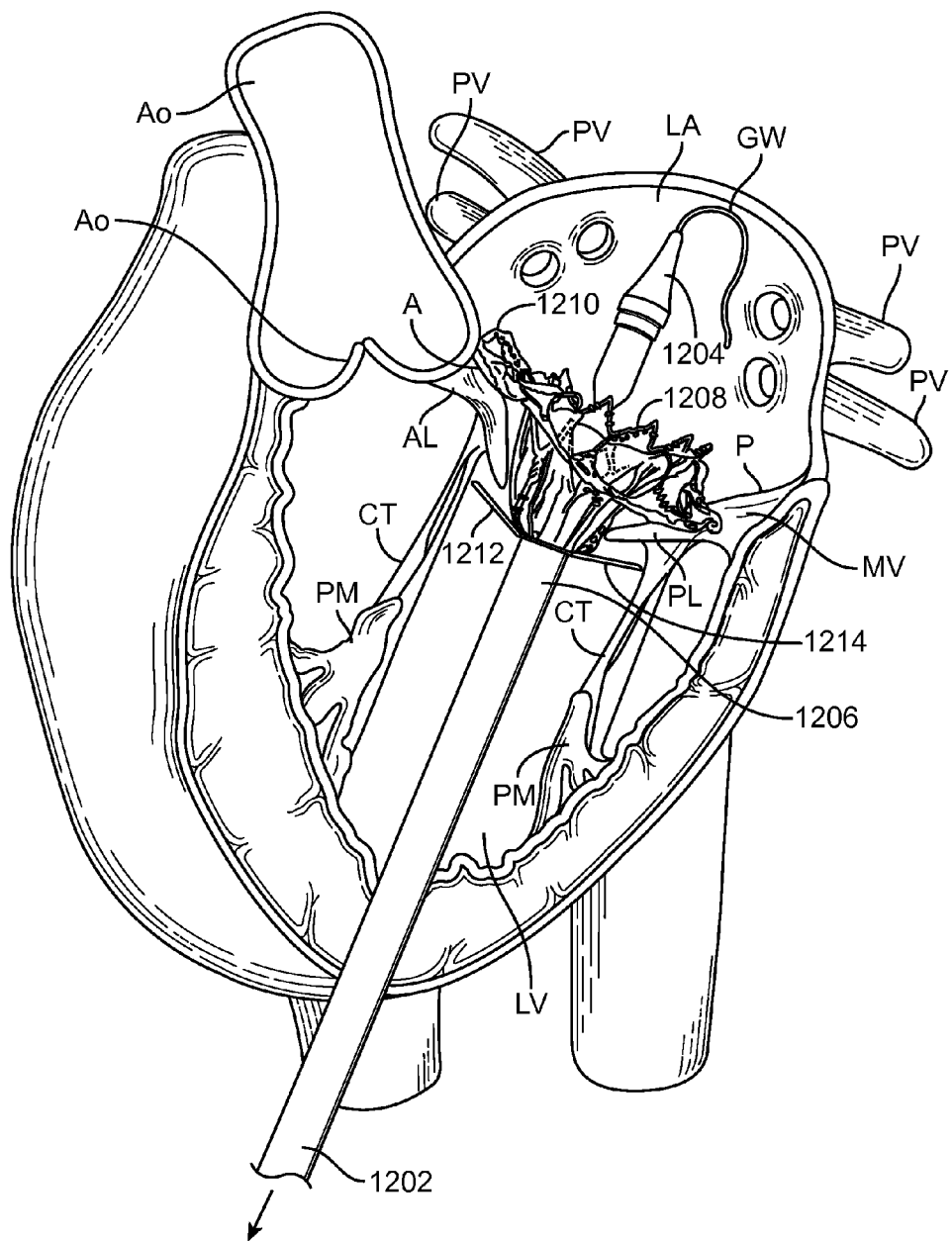
Figure 12F:
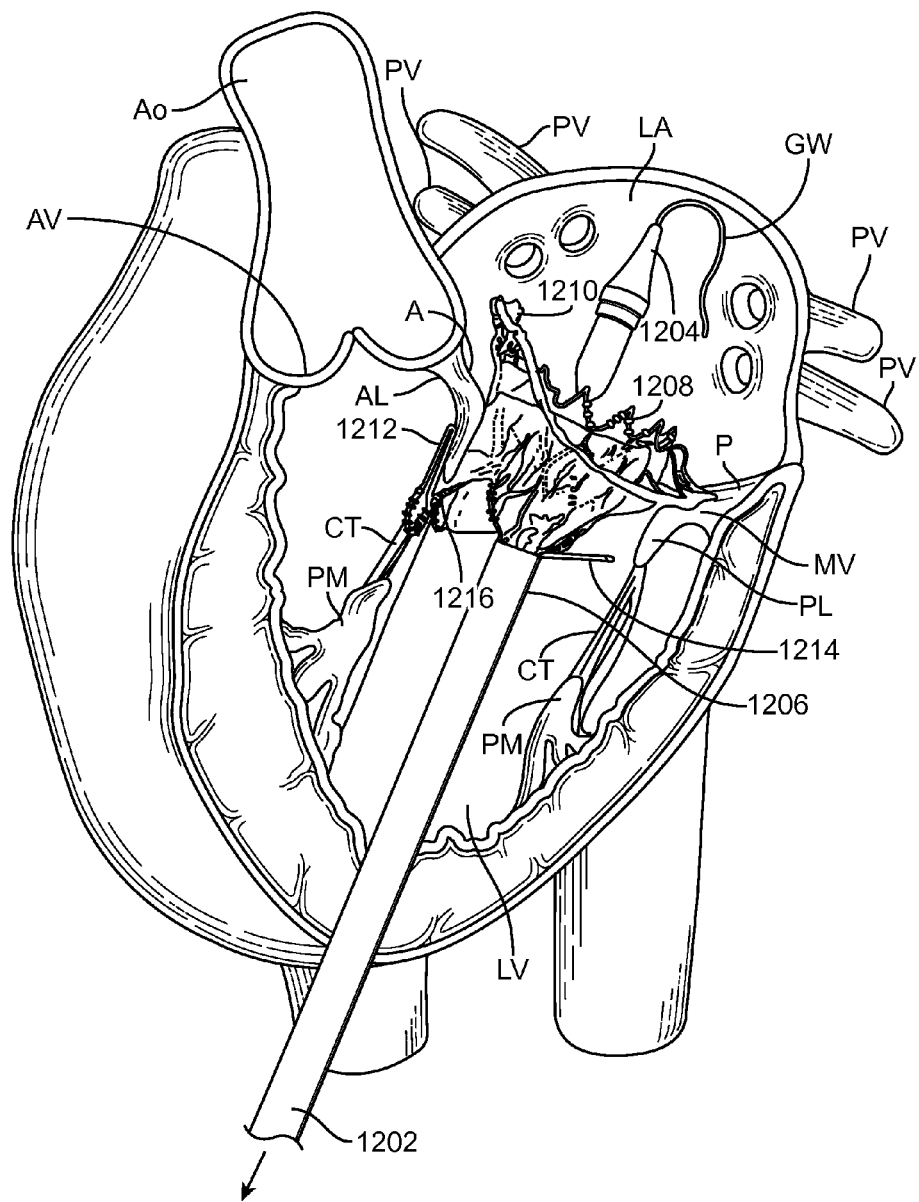

As the outer sheath 1206 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 12E, retraction of sheath 1206 eventually allows both the anterior 1212 and posterior 1214 tabs to partially self-expand outward preferably without engaging the anterior or posterior leaflets or the chordae tendineae. In this embodiment, further retraction of the outer sheath 1206 then allows both the anterior tabs 1212 (only one visible in this view) to complete their self-expansion so that the anterior leaflet is captured between an inner surface of each of the anterior tabs and an outer surface of the ventricular skirt 1216, as illustrated in FIG. 12F. The posterior tab 1214 remains partially open, but has not completed its expansion yet. Additionally, the tips of the anterior tabs also anchor into the left and right fibrous trigones of the mitral valve, as will be illustrated in greater detail below.

Figure 12G:
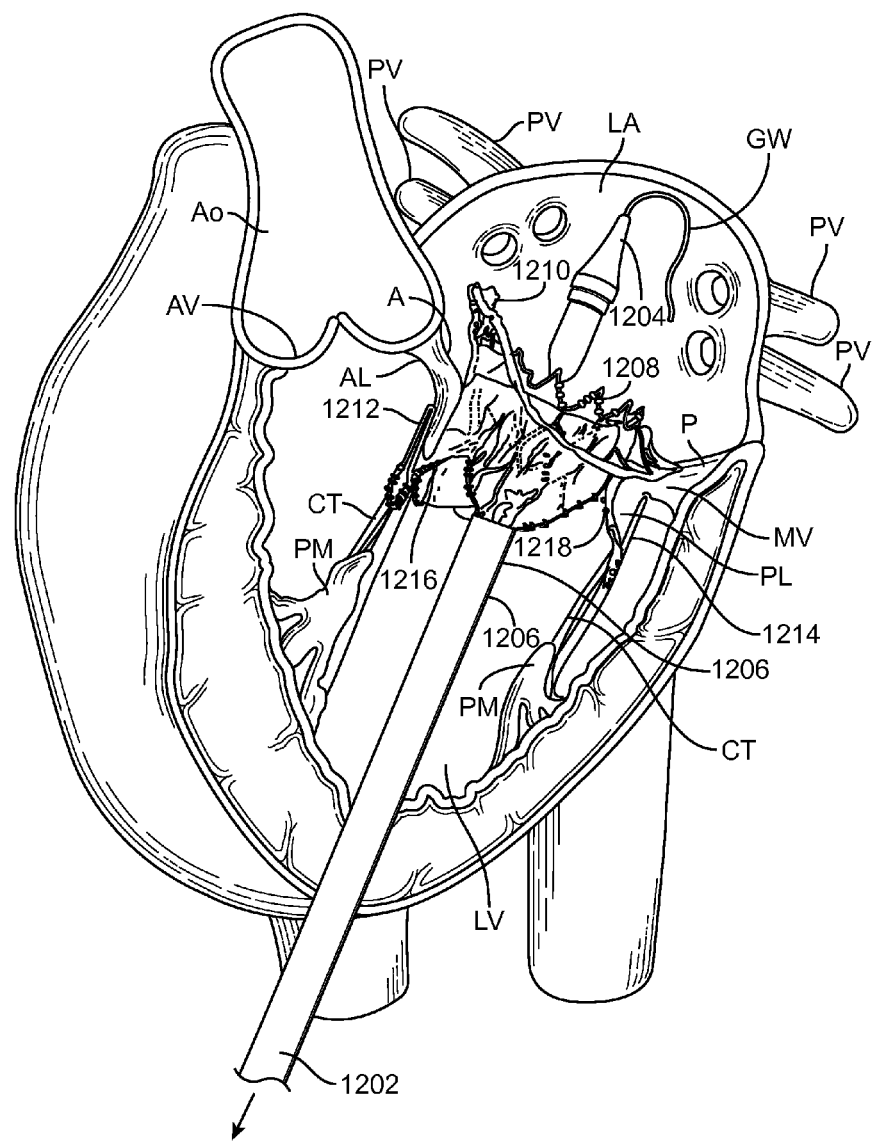
Figure 12H:
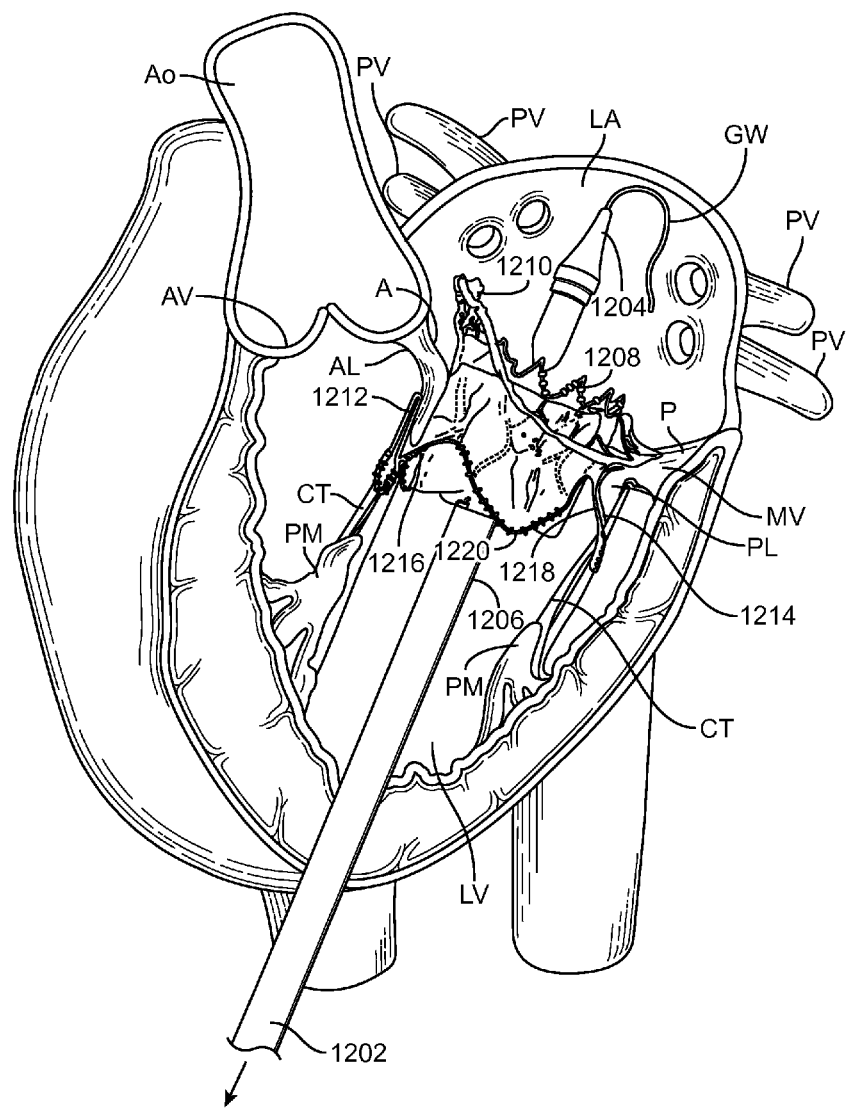

In FIG. 12G, further retraction of the outer sheath 1206 then releases the constraints from the posterior tab 1214 allowing it to complete its self-expansion, thereby capturing the posterior leaflet PL between an inner surface of the posterior tab 1214 and an outer surface of the ventricular skirt 1218. In FIG. 12H, the sheath is retracted further releasing the ventricular skirt 1220 and allowing the ventricular skirt 1220 to radially expand outward, further capturing the anterior and posterior leaflets between the outer surface of the ventricular skirt and their respective anterior or posterior tabs. Expansion of the ventricular skirt also pushes the anterior and posterior leaflets outward, thereby ensuring that the native leaflets do not interfere with any portion of the prosthetic valve or the prosthetic valve leaflets. The prosthetic valve is now anchored in position above the mitral valve, along the annulus, to the valve leaflets, and below the mitral valve, thereby securing it in position.

Figure 12I:
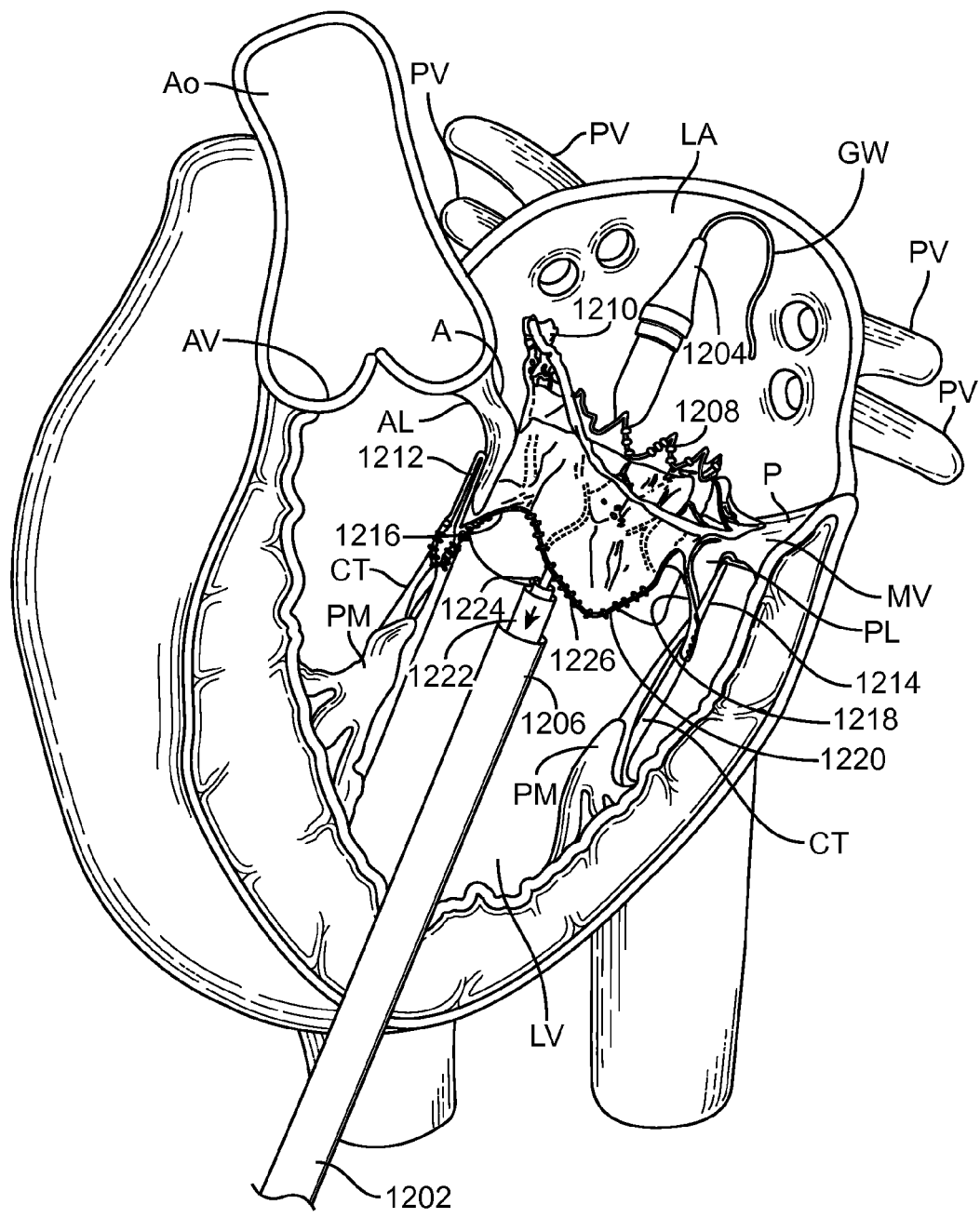
Figure 12J:
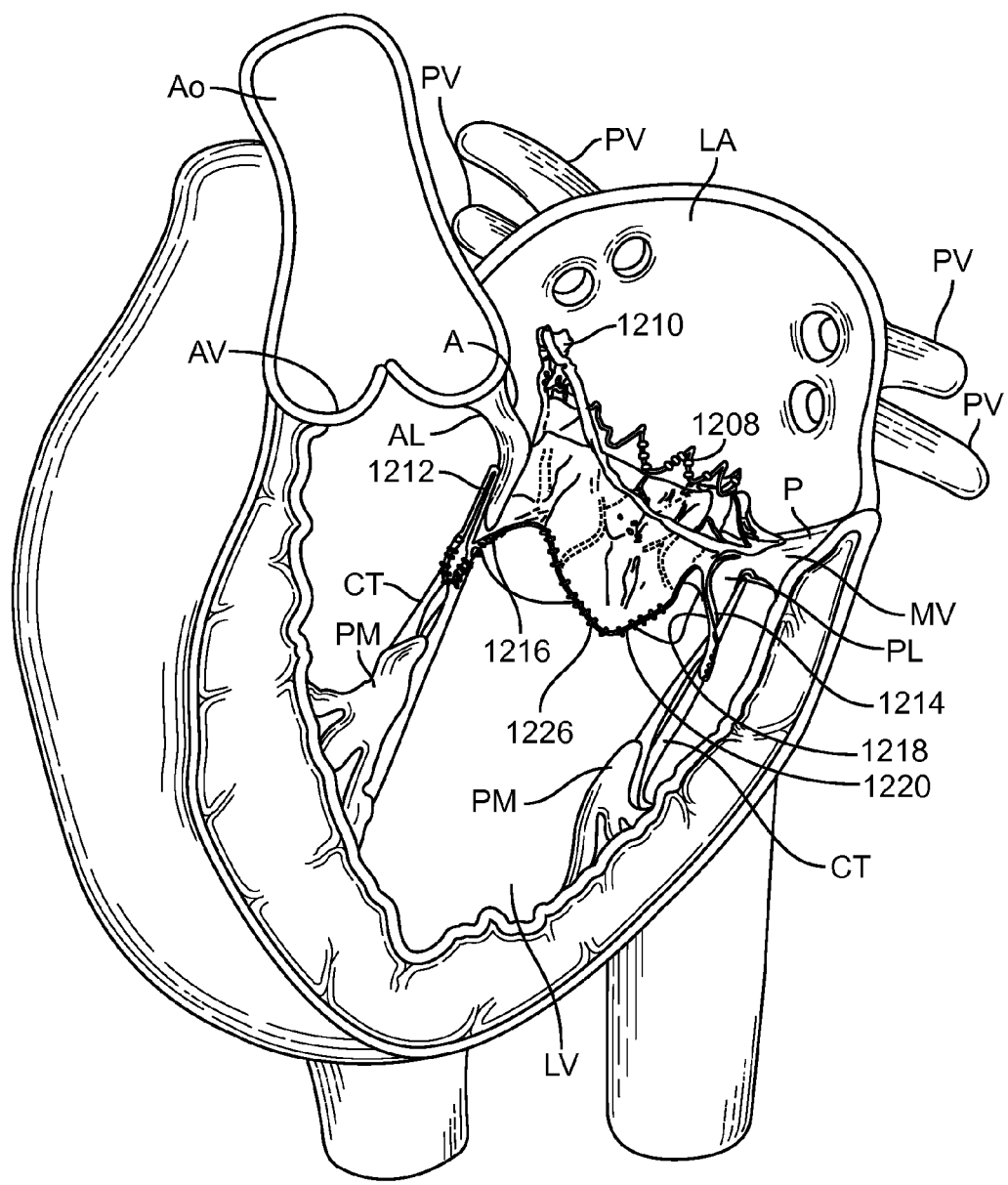

Further actuation of the delivery device now retracts the outer sheath 1206 and the bell catheter shaft 1222 so as to remove the constraint from the hub catheter 1224, as illustrated in FIG. 12I. This permits the prosthetic valve commissures 1226 to be released from the hub catheter, thus the commissures expand to their biased configuration. The delivery system 1202 and guidewire GW are then removed, leaving the prosthetic valve 1208 in position where it takes over for the native mitral valve, as seen in FIG. 12J.

Figure 12K:
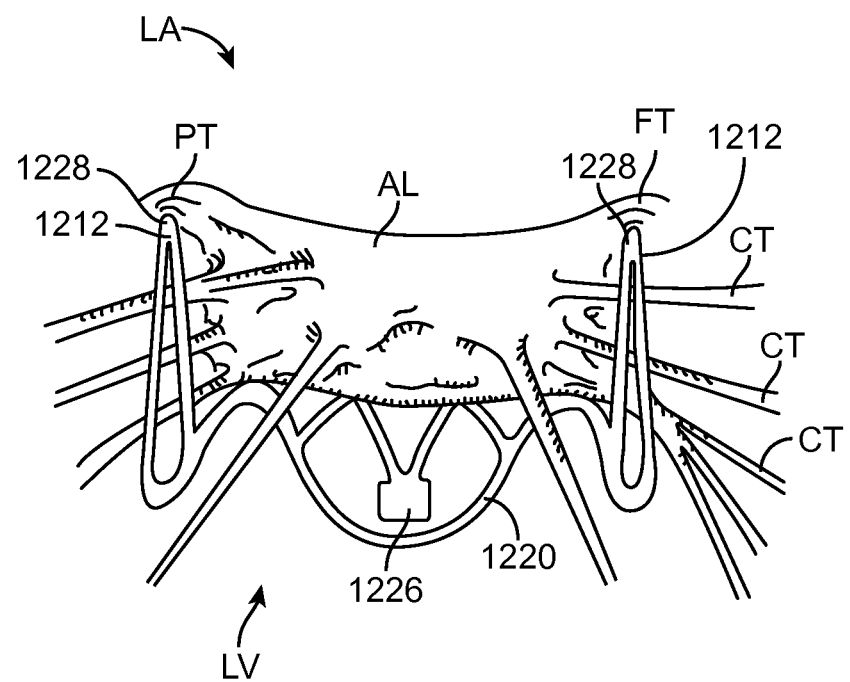
Figure 12L:
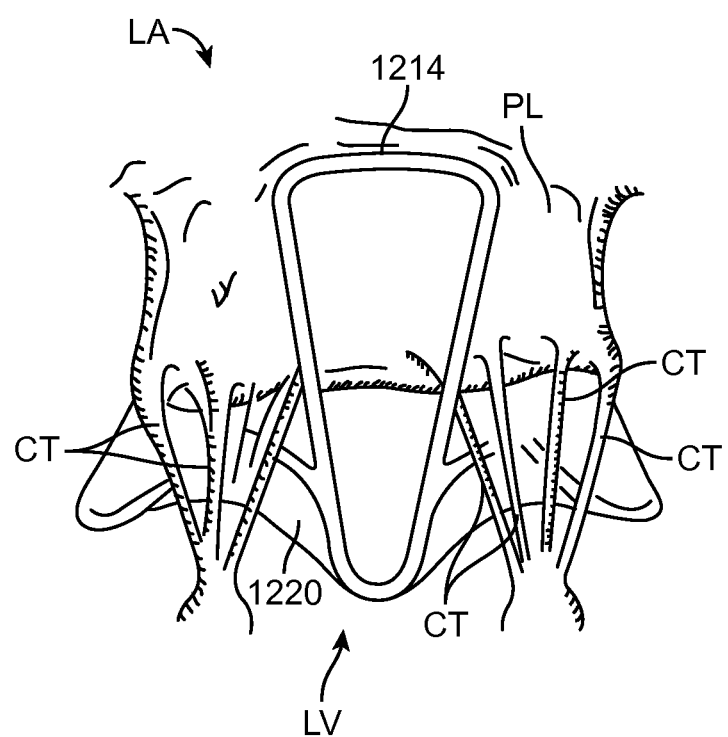

FIGS. 12K and 12L highlight engagement of the anterior and posterior tabs with the respective anterior and posterior leaflets. In FIG. 12K, after anterior tabs 1212 have been fully expanded, they capture the anterior leaflet AL and adjacent chordae tendineae between an inside surface of the anterior tab and an outer surface of the ventricular skirt 1220. Moreover, the tips 1228 of the anterior tabs 1212 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 12L illustrates engagement of the posterior tab 1214 with the posterior leaflet PL which is captured between an inner surface of the posterior tab and an outer surface of the ventricular skirt 1220. Additionally, adjacent chordae tendineae are also captured between the posterior tab and ventricular skirt.

FIGS. 13A-13L illustrate another exemplary embodiment of a delivery method. This embodiment is similar to that previously described, with the major difference being the order in which the prosthetic cardiac valve self-expands into engagement with the mitral valve. Any delivery device or any prosthetic cardiac valve disclosed herein may be used, however in preferred embodiments, the embodiment of FIG. 7 is used. Varying the order may allow better positioning of the implant, easier capturing of the valve leaflets, and better anchoring of the implant. This exemplary method also preferably uses a transapical route, although transseptal may also be used.

Figure 13A:
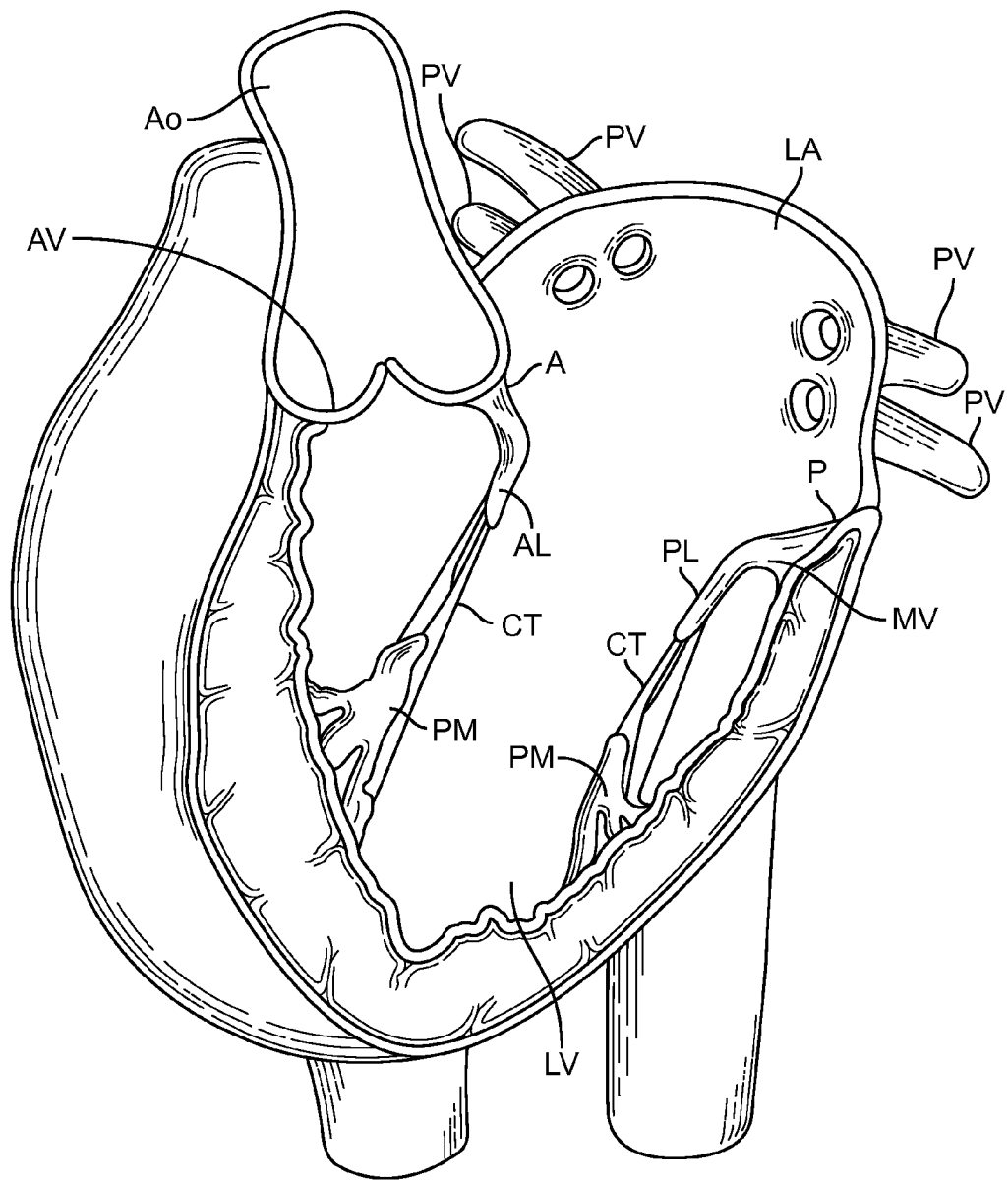
FIGS. 13A-13L illustrate another exemplary method of implanting a prosthetic cardiac valve.

FIG. 13A illustrates the basic anatomy of the left side of a patient's heart including the left artrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with pappillary muscles PM. The blood is then pumped out of the left ventricle into the aorta AO with the aortic valve AV preventing regurgitation.

Figure 13B:
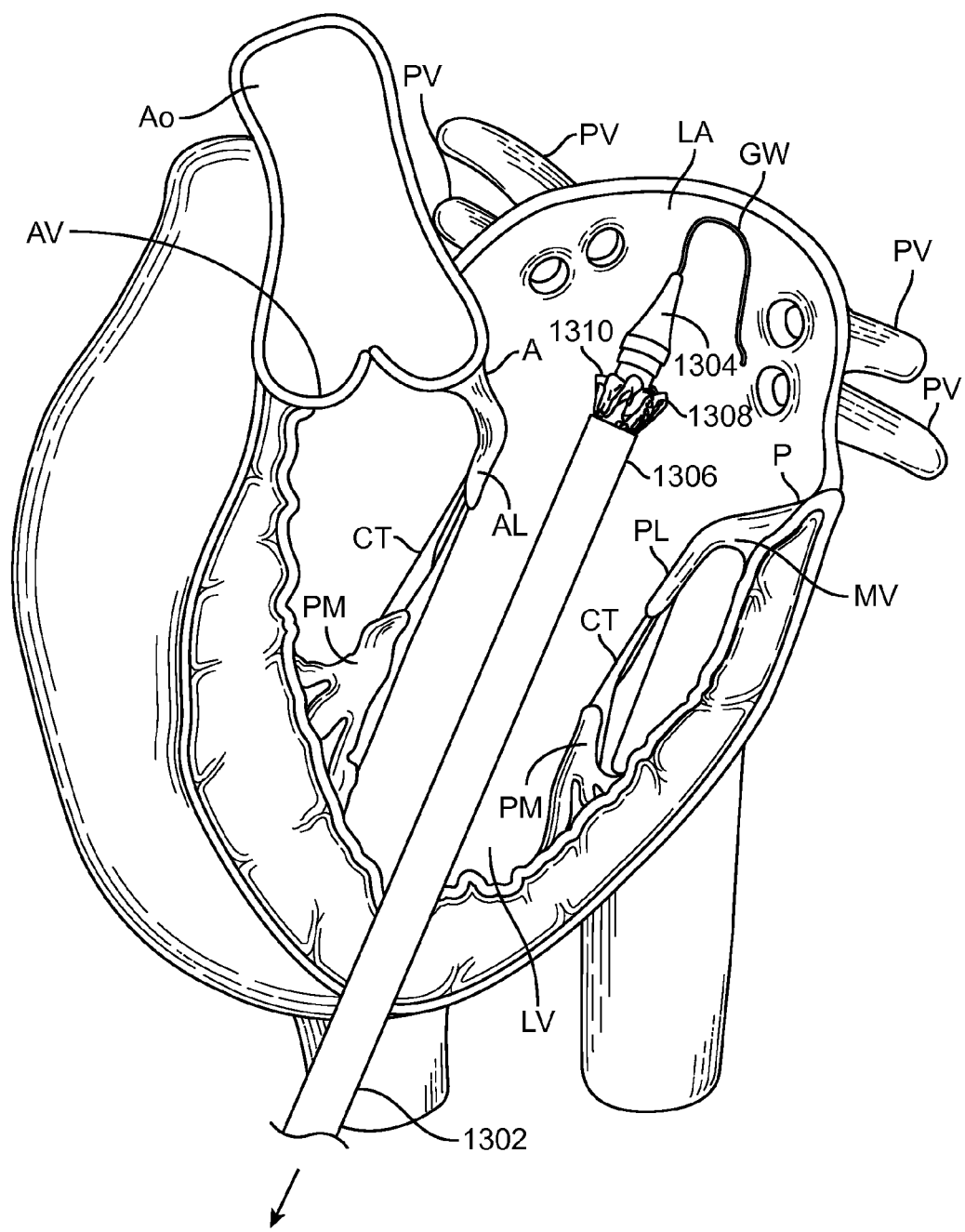
Figure 13C:
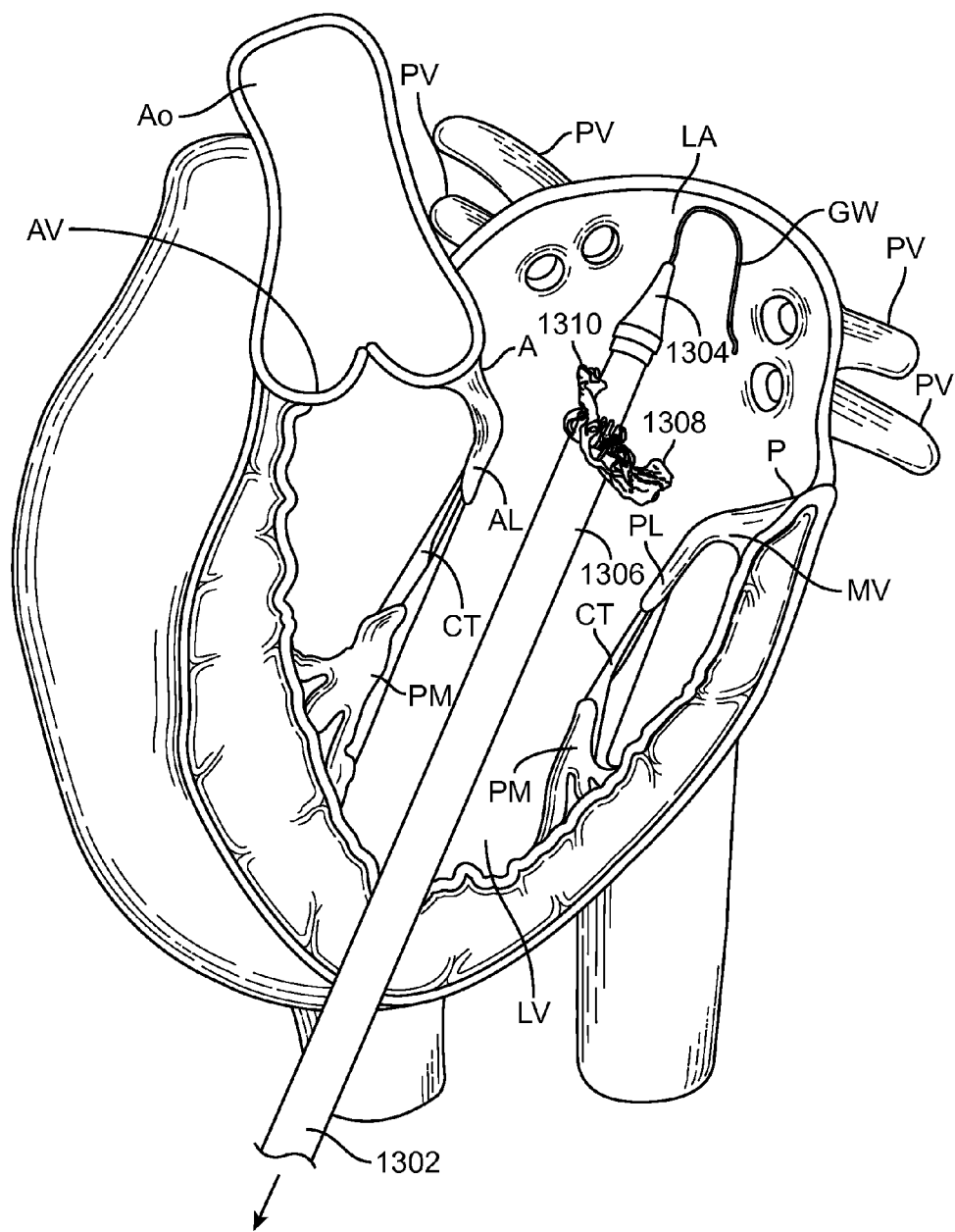
Figure 13D:
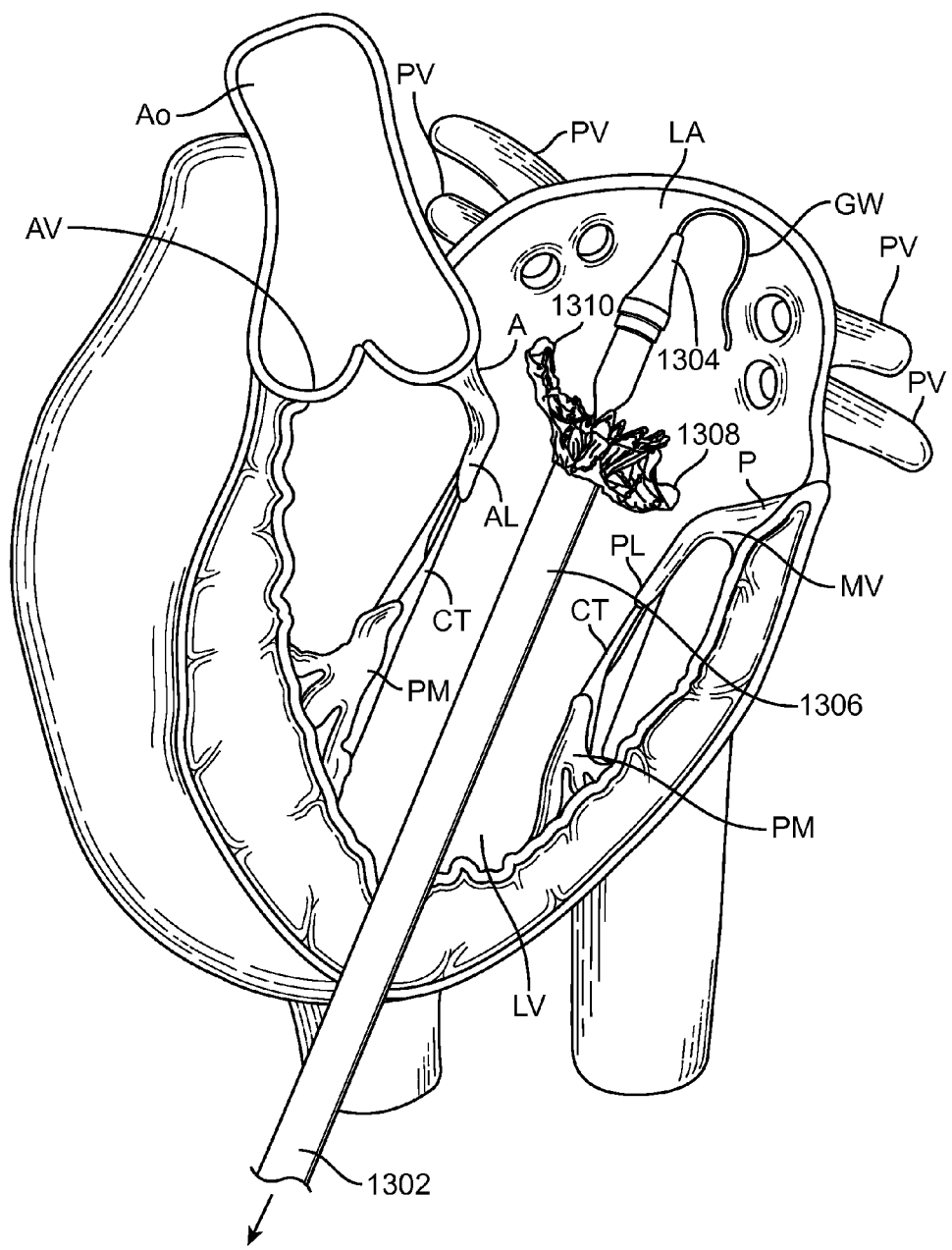

FIG. 13B illustrates transapical delivery of a delivery system 1302 through the apex of the heart into the left atrium LA. The delivery system 1302 may be advanced over a guidewire GW into the left atrium, and a tissue penetrating tip 1304 helps the delivery system pass through the apex of the heart by dilating the tissue and forming a larger channel for the remainder of the delivery system to pass through. The delivery catheter carries prosthetic cardiac valve 1308. Once the distal portion of the delivery system has been advanced into the left atrium, the outer sheath 1306 may be retracted proximally (e.g. toward the operator) thereby removing the constraint from the atrial portion of the prosthetic valve 1308. This allows the atrial skirt 1310 to self-expand radially outward. In FIG. 13C, as the outer sheath is further retracted, the atrial skirt continues to self-expand and peek out, until it fully deploys as seen in FIG. 13D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle.

Figure 13E:
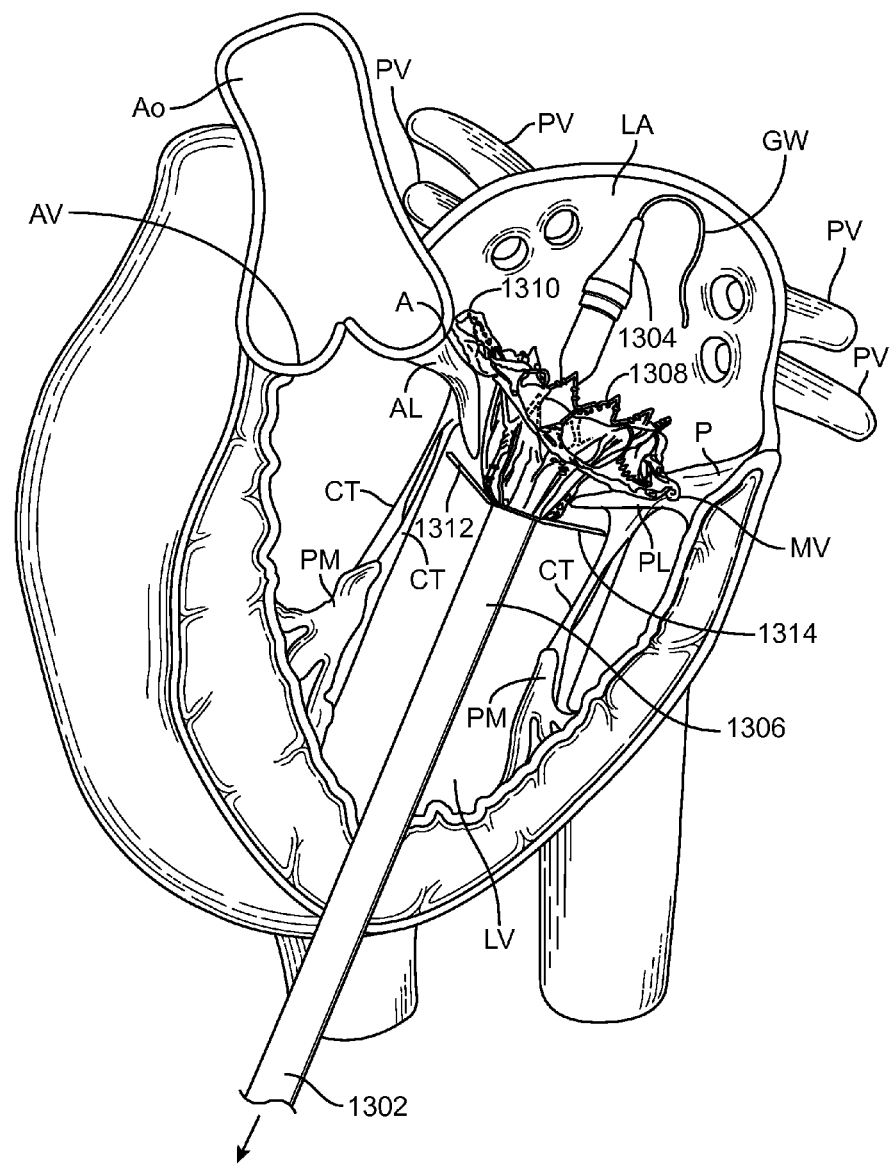
Figure 13F:
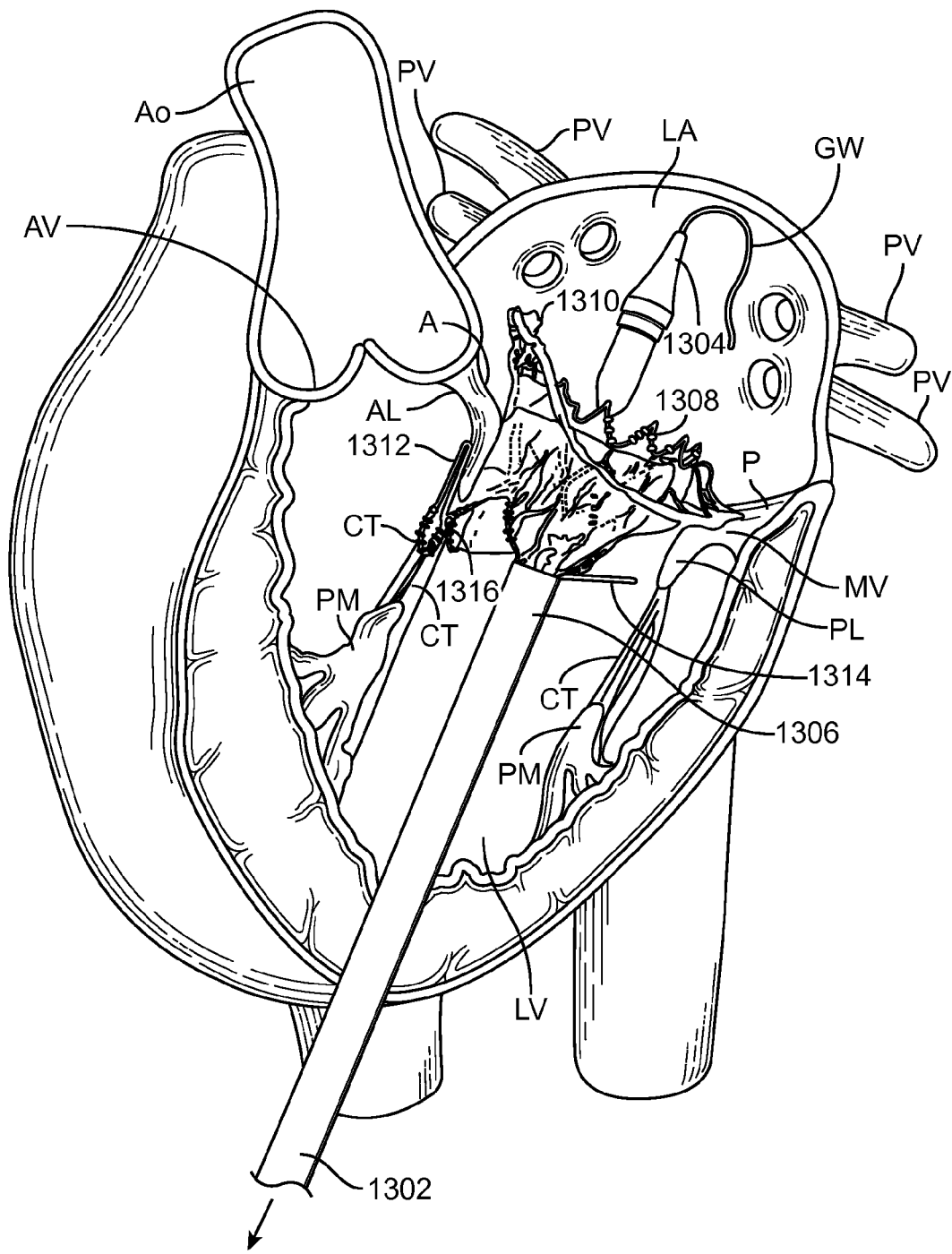

As the outer sheath 1306 continues to be proximally retracted, the annular region of the prosthetic cardiac valve self-expands next into engagement with the valve annulus. The annular region also preferably has the D-shaped geometry, although it may also be cylindrical or have other geometries to match the native anatomy. In FIG. 13E, retraction of sheath 1306 eventually allows both the anterior 1312 and posterior 1314 tabs to partially self-expand outward preferably without engaging the anterior or posterior leaflets or the chordae tendineae. In this embodiment, further retraction of the outer sheath 1306 then allows both the anterior tabs 1312 (only one visible in this view) to complete their self-expansion so that the anterior leaflet is captured between an inner surface of each of the anterior tabs and an outer surface of the ventricular skirt 1316, as illustrated in FIG. 13F. The posterior tab 1214 remains partially open, but has not completed its expansion yet. Additionally, the tips of the anterior tabs also anchor into the left and right fibrous trigones of the mitral valve, as will be illustrated in greater detail below.

Figure 13G:
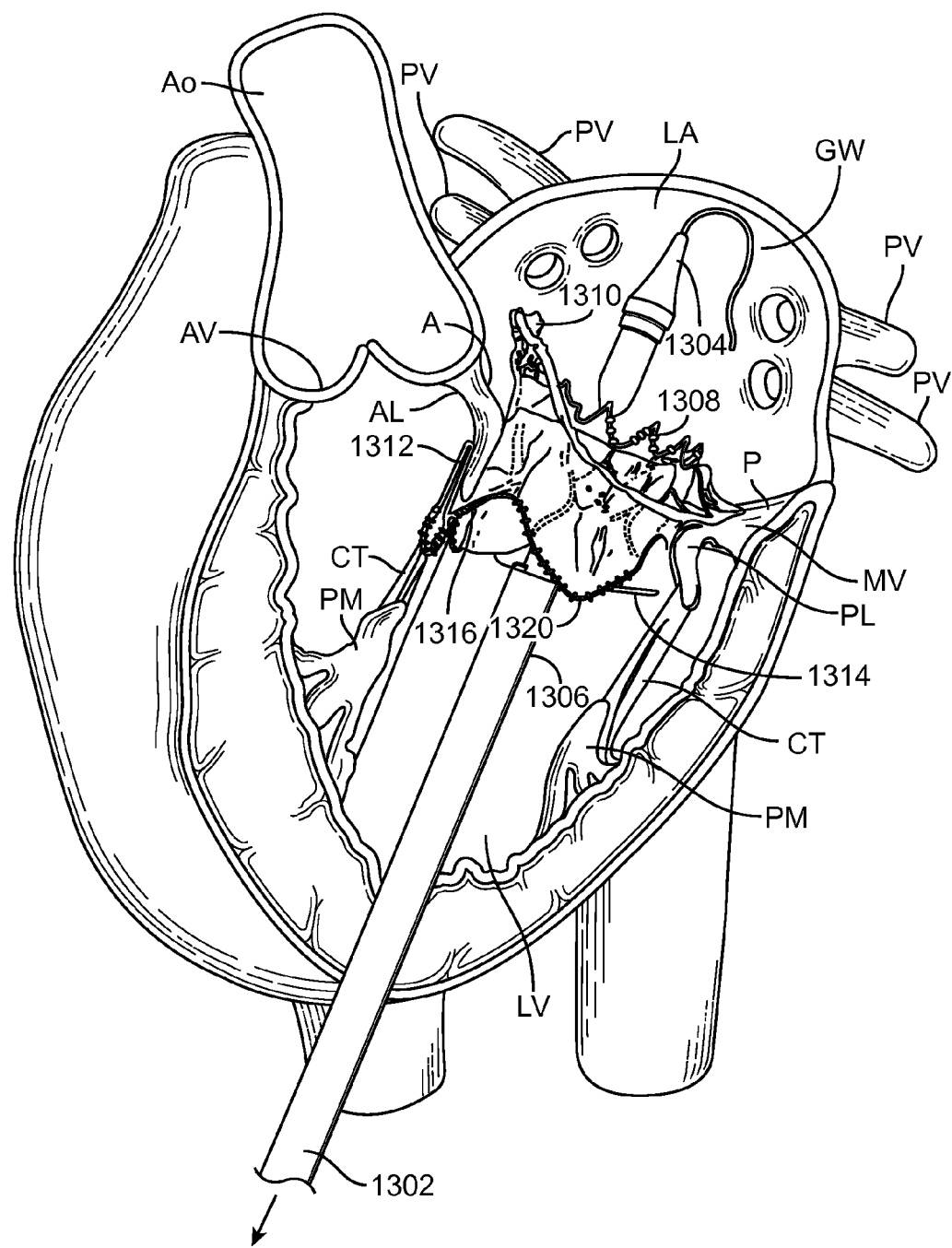
Figure 13H:
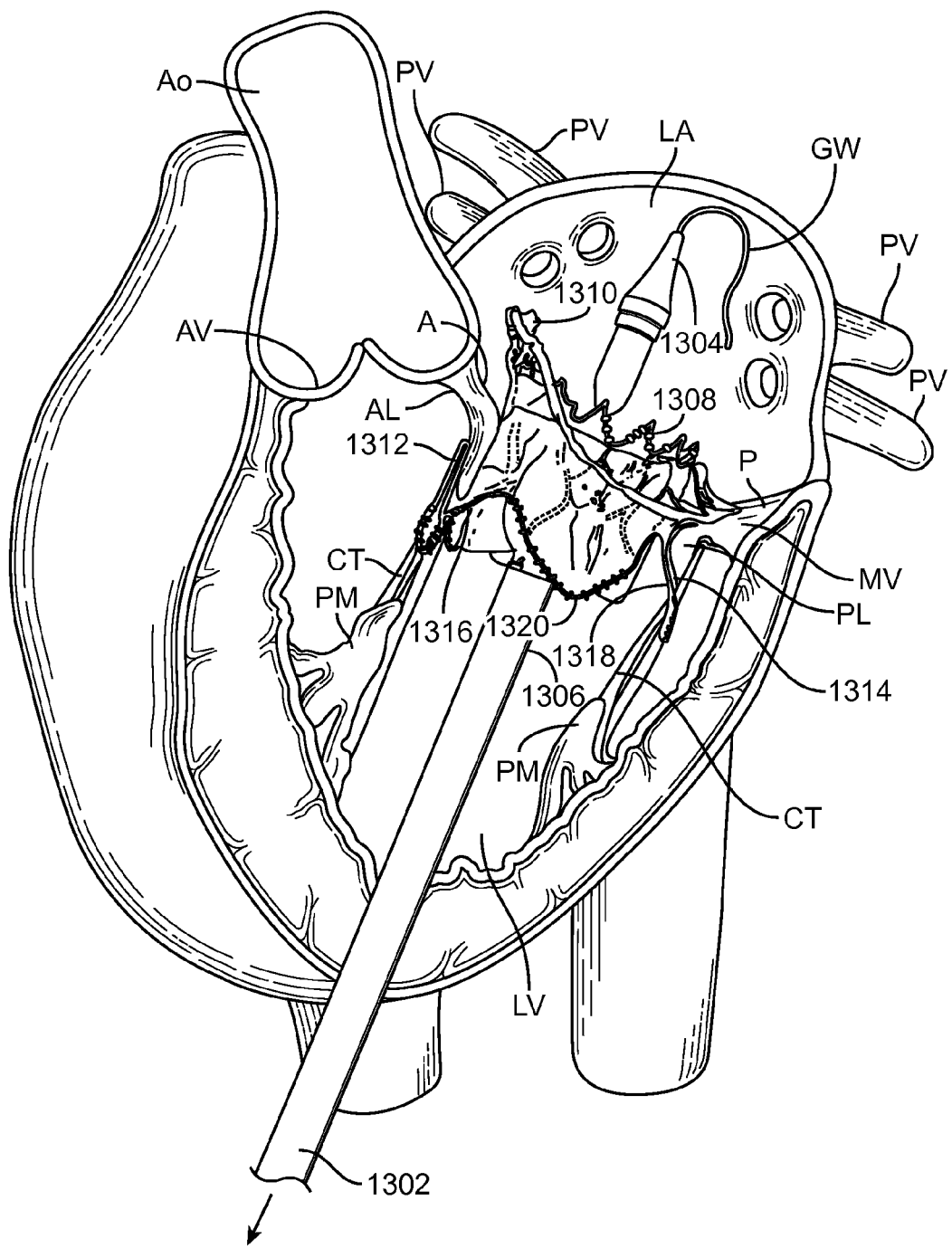

In FIG. 13G, further retraction of the outer sheath 1306 then releases the constraint from the ventricular skirt 1320 allowing the ventricular skirt to radially expand. This then further captures the anterior lealflets AL between the anterior tab 1312 and the ventricular skirt 1316. Expansion of the ventricular skirt also pushes the anterior and posterior leaflets outward, thereby ensuring that the native leaflets do not interfere with any portion of the prosthetic valve or the prosthetic valve leaflets. Further retraction of sheath 1306 as illustrated in FIG. 13H releases the constraint from the posterior tab 1314 allowing it to complete its self-expansion, thereby capturing the posterior leaflet PL between an inner surface of the posterior tab 1314 and an outer surface of the ventricular skirt 1318. The prosthetic valve is now anchored in position above the mitral valve, along the annulus, to the valve leaflets, and below the mitral valve, thereby securing it in position.

Figure 13I:
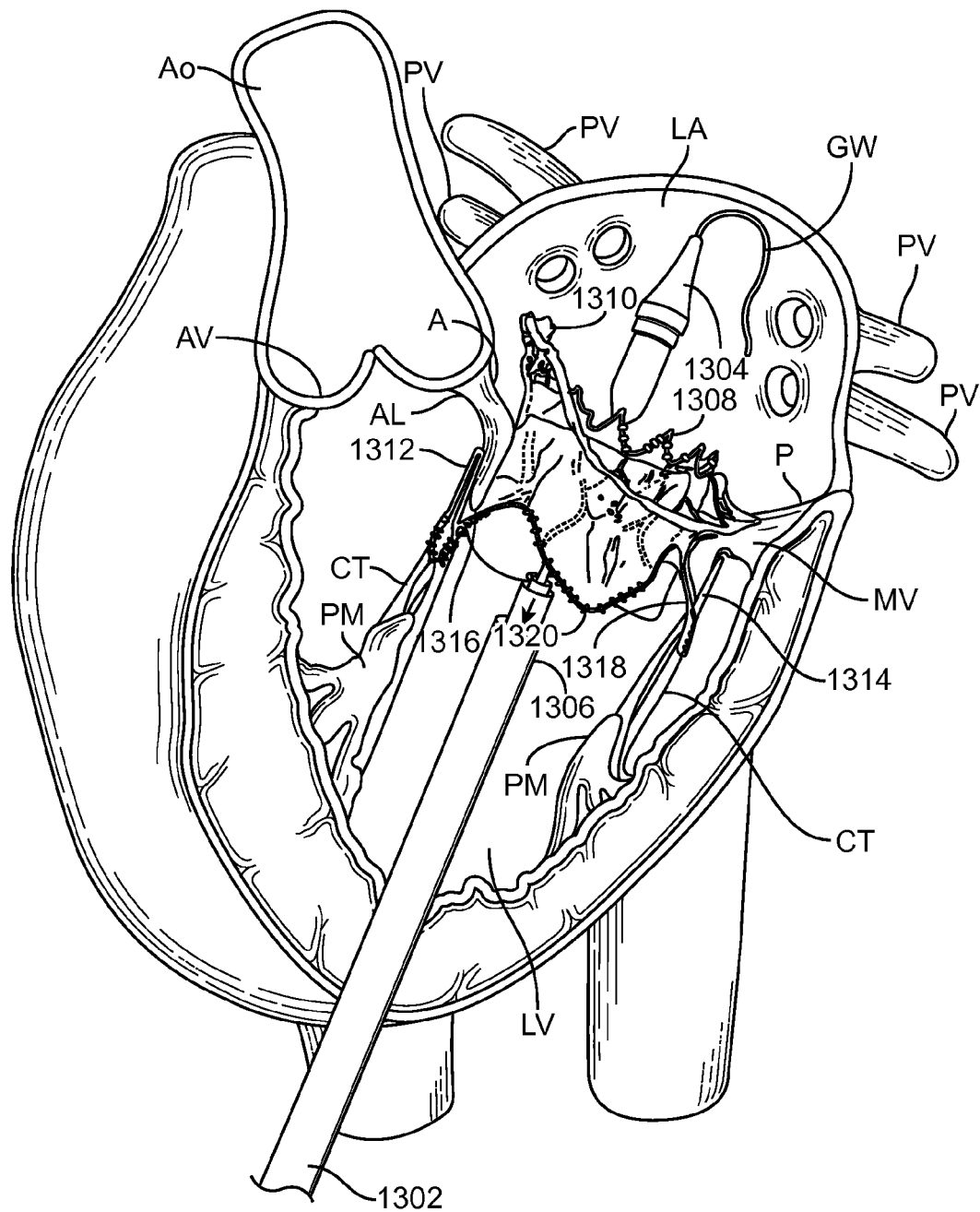
Figure 13J:
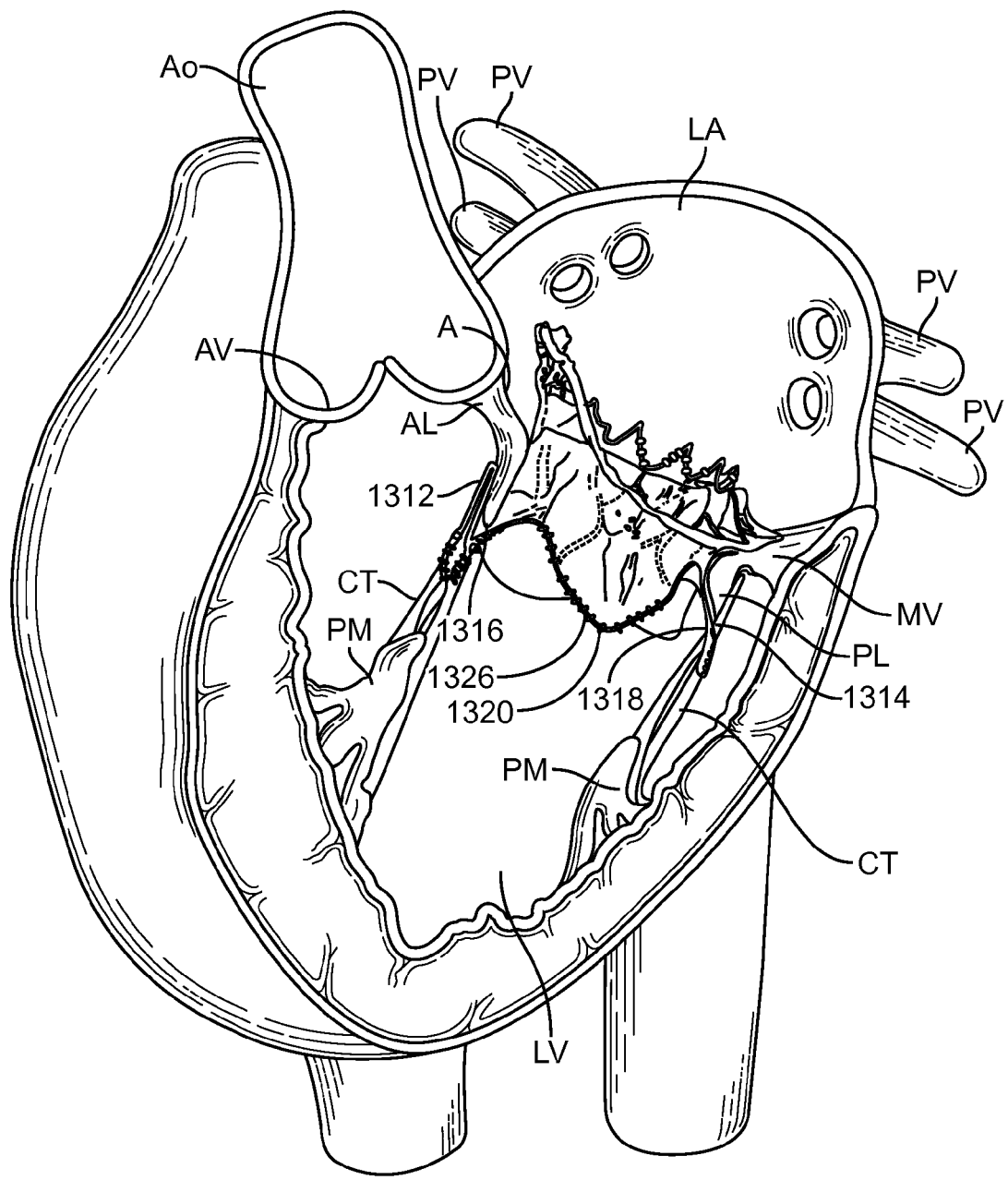

Further actuation of the delivery device now retracts the outer sheath 1306 and the bell catheter shaft 1322 so as to remove the constraint from the hub catheter 1324, as illustrated in FIG. 13I. This permits the prosthetic valve commissures 1326 to be released from the hub catheter, thus the commissures expand to their biased configuration. The delivery system 1302 and guidewire GW are then removed, leaving the prosthetic valve 1308 in position where it takes over for the native mitral valve, as seen in FIG. 13J.

Figure 13K:
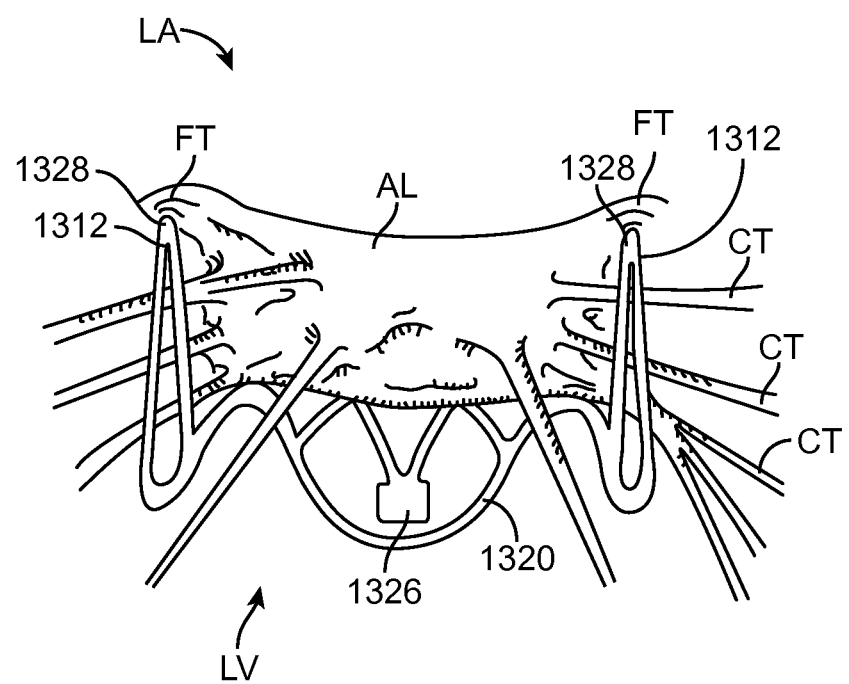
Figure 13L:
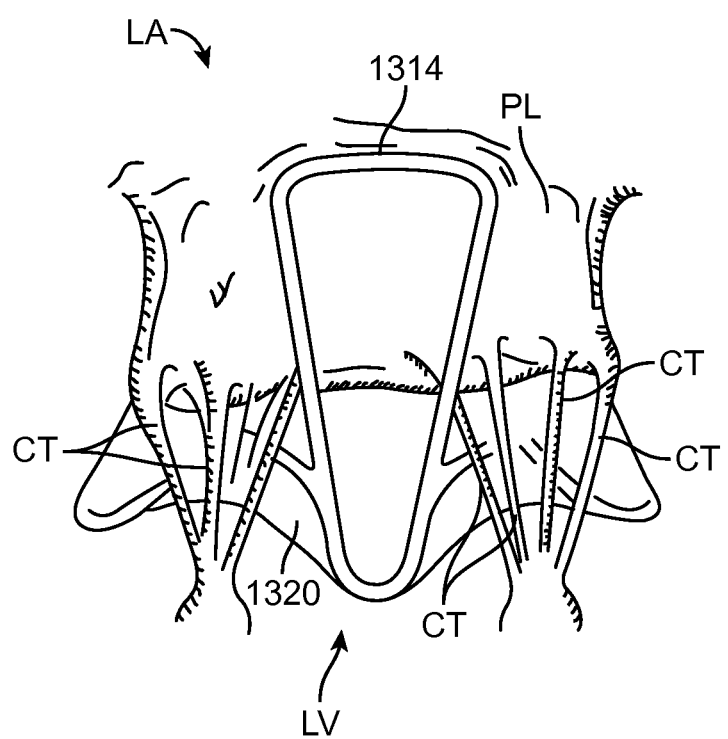

FIGS. 13K and 13L highlight engagement of the anterior and posterior tabs with the respective anterior and posterior leaflet. In FIG. 13K, after anterior tabs 1312 have been fully expanded, they capture the anterior leaflet AL and adjacent chordae tendineae between an inside surface of the anterior tab and an outer surface of the ventricular skirt 1320. Moreover, the tips 1328 of the anterior tabs 1312 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 13L illustrates engagement of the posterior tab 1314 with the posterior leaflet PL which is captured between an inner surface of the posterior tab and an outer surface of the ventricular skirt 1320. Additionally, adjacent chordae tendineae are also captured between the posterior tab and ventricular skirt.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for loading a prosthesis onto a delivery system, said method comprising:
   providing a housing, the housing comprising one or more actuators that move radially inward or radially outward;
   providing a prosthetic valve having a plurality of commissure posts coupled thereto, wherein the prosthetic valve comprises an unbiased diameter;
   passing the prosthetic valve through the housing thereby reducing a diameter at a first end of the prosthetic valve to a first diameter;
   actuating the one or more actuators thereby moving the plurality of commissure posts at the first end radially inward to a diameter smaller than the first diameter; and
   coupling the plurality of commissure posts in the smaller diameter configuration to a delivery device.

2. The method of claim 1, wherein passing the prosthesis through the housing comprises passing the prosthetic valve through a constant diameter portion of a central channel in the first housing.

3. The method of claim 1, wherein actuating the one or more actuators comprises depressing one or more pins or fingers radially inward to engage the plurality of commissure posts, the plurality of commissure moving radially inward into the diameter smaller than the first diameter, the one or more pins or fingers passing through a wall of the housing.

4. The method of claim 3, wherein depressing comprises simultaneously depressing the one or more pins or fingers.

5. The method of claim 1, wherein reducing the diameter of the prosthetic valve at the first end comprises passing the prosthetic valve through a tapered central channel in the housing.

6. The method of claim 5, wherein passing the prosthetic valve through the tapered central channel comprises pushing or pulling the prosthetic valve therethrough.

7. The method of claim 5, wherein passing the prosthetic valve through the tapered central channel comprises shaping the prosthetic valve to have a circular cross-section.

8. The method of claim 1, further comprising further reducing diameter of the prosthetic valve at the first end from the first diameter to a second diameter less than the first diameter.

9. The method of claim 8, wherein reducing diameter of the prosthetic valve at the first end from the first diameter to the second diameter comprises passing the prosthetic valve through a second tapered central channel in the housing.

10. The method of claim 9, wherein passing the prosthetic valve through the second tapered central channel comprises pushing or pulling the prosthetic valve therethrough.

11. The method of claim 1, wherein the delivery device comprises an inner shaft and an outer shaft slidably disposed thereover, and wherein coupling the plurality of commissure posts in the smaller diameter configuration comprises disposing the plurality of commissure posts between the inner shaft and outer shafts.

12. The method of claim 1, wherein coupling the plurality of commissure posts comprises releasably engaging the commissure posts with the delivery device.

13. The method of claim 1, wherein the prosthetic valve is fabricated from a nickel titanium alloy, and the method further comprises cooling the prosthetic valve to a temperature less than or equal to the austenitic finish temperature of the prosthetic valve.

14. The method of claim 13, wherein cooling the prosthetic valve comprises cooling the prosthetic valve in chilled saline.

15. The method of claim 8, wherein the diameter of the prosthetic valve is reduced to the first diameter in a first housing, and wherein the diameter of the prosthetic valve is reduced from the first diameter to the second diameter in a second housing, and wherein the method further comprises coupling the first housing with the second housing.

16. The method of claim 15, further comprising uncoupling the first housing from the second housing after the diameter has been reduced to the first diameter.

17. The method of claim 1, further comprising supporting an inner surface of the prosthesis with a support element.

* * * * *